United States Patent
Li et al.

(10) Patent No.: US 11,371,070 B2
(45) Date of Patent: Jun. 28, 2022

(54) ANTIOXIDANT PROTEIN HYDROLYSATES AND PEPTIDES FROM CEREAL GRAIN CROPS

(71) Applicant: Kansas State University Research Foundation, Manhattan, KS (US)

(72) Inventors: Yonghui Li, Manhattan, KS (US); Shiwei Xu, Manhattan, KS (US); Ruijia Hu, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 104 days.

(21) Appl. No.: 16/670,602

(22) Filed: Oct. 31, 2019

(65) Prior Publication Data

US 2020/0140913 A1 May 7, 2020

Related U.S. Application Data

(60) Provisional application No. 62/754,377, filed on Nov. 1, 2018.

(51) Int. Cl.
*C12P 21/06* (2006.01)
*A23L 33/18* (2016.01)
*A23L 7/104* (2016.01)

(52) U.S. Cl.
CPC .............. *C12P 21/06* (2013.01); *A23L 7/107* (2016.08); *A23L 33/18* (2016.08); *A23V 2002/00* (2013.01)

(58) Field of Classification Search
CPC ........... C12P 21/06; A23L 33/18; A23L 7/107
USPC ........................................................ 426/18
See application file for complete search history.

(56) References Cited

PUBLICATIONS

Agrawal, H. et al. Food Sci. Technol. 84: 608-616 (Year: 2017).*
Elias, et al., "Antioxidant activity of proteins and peptides", Grit Rev Food Sci Nutr. May 2008;48(5):430-41 (abstract attached).
Sarmadi, et al., "Antioxidative peptides from food proteins: A review", Peptides vol. 31, Issue 10, Oct. 2010, pp. 1949-1956 (abstract attached).
Brewer, "Natural Antioxidants: Sources, Compounds, Mechanisms of Action, and Potential Applications", Comprehensive Reviews in Food Science and Food Safety, 2011, 10, 4, pp. 221-247.
Sila, et al., "Antioxidant peptides from marine by-products: Isolation, identification and application in food systems. A review", Journal of Functional Foods, vol. 21, Mar. 2016, pp. 10-26 (abstract attached).

* cited by examiner

*Primary Examiner* — Hamid R Badr
(74) *Attorney, Agent, or Firm* — Hovey Williams LLP

(57) ABSTRACT

Described herein are antioxidant peptides and methods of producing the same. The antioxidant peptides are produced from cereal grain protein sources, which provide a number of advantages over more expensive antioxidant sources and synthetically-produced antioxidants. The antioxidant peptides are produced by reacting the cereal grain material with an enzyme capable of hydrolyzing proteins within the material, thereby forming hydrolysate peptides. The hydrolysate peptides are then selectively recovered to form an antioxidant peptide product. The antioxidant peptide product is useful in a number of applications, particularly as an ingredient in a food product to provide antioxidant properties to the food product.

19 Claims, 53 Drawing Sheets

Specification includes a Sequence Listing.

```
                        SEQUENCE LISTING

<160> NUMBER OF SEQ ID NOS: 48

<210> SEQ ID NO 1
<211> LENGTH: 4
<212> TYPE: PRT
<213> ORGANISM: Sorghum bicolor

<400> SEQUENCE: 1

Met Asp Met Gln
1

<210> SEQ ID NO 2
<211> LENGTH: 4
<212> TYPE: PRT
<213> ORGANISM: Sorghum bicolor

<400> SEQUENCE: 2

Gln Gln Trp Gln
1

<210> SEQ ID NO 3
<211> LENGTH: 4
<212> TYPE: PRT
<213> ORGANISM: Sorghum bicolor

<400> SEQUENCE: 3

Gln Trp Gln Gln
1

<210> SEQ ID NO 4
<211> LENGTH: 4
<212> TYPE: PRT
<213> ORGANISM: Sorghum bicolor

<400> SEQUENCE: 4

Leu Arg Gln Gln
1

<210> SEQ ID NO 5
<211> LENGTH: 5
<212> TYPE: PRT
<213> ORGANISM: Sorghum bicolor

<400> SEQUENCE: 5

Gln Leu Gln Gly Val
1               5
```

<210> SEQ ID NO 6
<211> LENGTH: 4
<212> TYPE: PRT
<213> ORGANISM: Sorghum bicolor

<400> SEQUENCE: 6

Trp Gln Pro Asn
1

<210> SEQ ID NO 7
<211> LENGTH: 7
<212> TYPE: PRT
<213> ORGANISM: Sorghum bicolor

<400> SEQUENCE: 7

Gln Ala Met Cys Gly Val Val
1               5

<210> SEQ ID NO 8
<211> LENGTH: 7
<212> TYPE: PRT
<213> ORGANISM: Sorghum bicolor

<400> SEQUENCE: 8

Ala Met Cys Gly Val Val Gln
1               5

<210> SEQ ID NO 9
<211> LENGTH: 7
<212> TYPE: PRT
<213> ORGANISM: Sorghum bicolor

<400> SEQUENCE: 9

Ser Ala Ser Ala Leu Gln Met
1               5

<210> SEQ ID NO 10
<211> LENGTH: 9
<212> TYPE: PRT
<213> ORGANISM: Sorghum bicolor

<400> SEQUENCE: 10

Pro Ala Ala Gln Ala Leu Thr Pro Leu
1               5

<210> SEQ ID NO 11
<211> LENGTH: 9
<212> TYPE: PRT
<213> ORGANISM: Sorghum bicolor

<400> SEQUENCE: 11

Leu Pro Ala Ala Gln Ala Leu Thr Pro
1               5

<210> SEQ ID NO 12
<211> LENGTH: 8
<212> TYPE: PRT
<213> ORGANISM: Sorghum bicolor

<400> SEQUENCE: 12

Leu Pro Ser Tyr Cys Thr Thr Pro
1               5

<210> SEQ ID NO 13

```
<210> SEQ ID NO 13
<211> LENGTH: 8
<212> TYPE: PRT
<213> ORGANISM: Sorghum bicolor

<400> SEQUENCE: 13

Ser Ala Ala Ile Pro Pro Tyr Tyr
1               5

<210> SEQ ID NO 14
<211> LENGTH: 8
<212> TYPE: PRT
<213> ORGANISM: Sorghum bicolor

<400> SEQUENCE: 14

Cys Gly Leu Tyr Gln Leu Pro Ser
1               5

<210> SEQ ID NO 15
<211> LENGTH: 7
<212> TYPE: PRT
<213> ORGANISM: Sorghum bicolor

<400> SEQUENCE: 15

Tyr Ala Leu Arg Glu Gln Thr
1               5

<210> SEQ ID NO 16
<211> LENGTH: 6
<212> TYPE: PRT
<213> ORGANISM: Sorghum bicolor

<400> SEQUENCE: 16

Val Ala Gln Asn Met Pro
1               5

<210> SEQ ID NO 17
<211> LENGTH: 6
<212> TYPE: PRT
<213> ORGANISM: Sorghum bicolor

<400> SEQUENCE: 17

Val Gln Ser Val Val Gln
1               5

<210> SEQ ID NO 18
<211> LENGTH: 6
<212> TYPE: PRT
<213> ORGANISM: Sorghum bicolor

<400> SEQUENCE: 18

Gln Pro Gln Cys Ser Pro
1               5

<210> SEQ ID NO 19
<211> LENGTH: 8
<212> TYPE: PRT
<213> ORGANISM: Sorghum bicolor

<400> SEQUENCE: 19

Met Arg Met Met Asp Met Gln Ser
1               5

<210> SEQ ID NO 20
<211> LENGTH: 10
<212> TYPE: PRT
```

<213> ORGANISM: Sorghum bicolor

<400> SEQUENCE: 20

Gly Gly Gly Leu Tyr Pro Cys Ala Glu Tyr
1               5                   10

<210> SEQ ID NO 21
<211> LENGTH: 10
<212> TYPE: PRT
<213> ORGANISM: Sorghum bicolor

<400> SEQUENCE: 21

Val Ala Gln Val Ala Gln Asn Met Pro Ala
1               5                   10

<210> SEQ ID NO 22
<211> LENGTH: 10
<212> TYPE: PRT
<213> ORGANISM: Sorghum bicolor

<400> SEQUENCE: 22

Ala Val Ala Gln Val Ala Gln Asn Met Pro
1               5                   10

<210> SEQ ID NO 23
<211> LENGTH: 11
<212> TYPE: PRT
<213> ORGANISM: Sorghum bicolor

<400> SEQUENCE: 23

Thr Pro Cys Ala Thr Ser Ala Ala Ile Pro Pro
1               5                   10

<210> SEQ ID NO 24
<211> LENGTH: 9
<212> TYPE: PRT
<213> ORGANISM: Sorghum bicolor

<400> SEQUENCE: 24

Phe Leu Tyr Pro Cys Ala Glu Tyr Leu
1               5

<210> SEQ ID NO 25
<211> LENGTH: 9
<212> TYPE: PRT
<213> ORGANISM: Sorghum bicolor

<400> SEQUENCE: 25

Val Gln Ser Val Val Gln Gln Leu Gln
1               5

<210> SEQ ID NO 26
<211> LENGTH: 10
<212> TYPE: PRT
<213> ORGANISM: Sorghum bicolor

<400> SEQUENCE: 26

Met Asp Met Gln Ser Arg Cys Gln Ala Met
1               5                   10

<210> SEQ ID NO 27
<211> LENGTH: 10
<212> TYPE: PRT
<213> ORGANISM: Sorghum bicolor

<400> SEQUENCE: 27

Met Met Asp Met Gln Ser Arg Cys Gln Ala
1               5                   10

<210> SEQ ID NO 28
<211> LENGTH: 12
<212> TYPE: PRT
<213> ORGANISM: Sorghum bicolor

<400> SEQUENCE: 28

Thr Pro Leu Ala Met Ala Val Ala Gln Val Ala Gln
1               5                   10

<210> SEQ ID NO 29
<211> LENGTH: 9
<212> TYPE: PRT
<213> ORGANISM: Sorghum bicolor

<400> SEQUENCE: 29

Gln Gln Met Arg Met Met Asp Met Gln
1               5

<210> SEQ ID NO 30
<211> LENGTH: 5
<212> TYPE: PRT
<213> ORGANISM: Sorghum bicolor

<400> SEQUENCE: 30

Lys Met Val Ile Val
1               5

<210> SEQ ID NO 31
<211> LENGTH: 6
<212> TYPE: PRT
<213> ORGANISM: Sorghum bicolor

<400> SEQUENCE: 31

Leu Ala Val Cys Leu Ala
1               5

<210> SEQ ID NO 32
<211> LENGTH: 6
<212> TYPE: PRT
<213> ORGANISM: Sorghum bicolor

<400> SEQUENCE: 32

Ala Val Cys Leu Ala Leu
1               5

<210> SEQ ID NO 33
<211> LENGTH: 5
<212> TYPE: PRT
<213> ORGANISM: Sorghum bicolor

<400> SEQUENCE: 33

Arg Gln Gln Cys Cys
1               5

<210> SEQ ID NO 34
<211> LENGTH: 5
<212> TYPE: PRT
<213> ORGANISM: Sorghum bicolor

<400> SEQUENCE: 34

```
Met Cys Gly Trp Gln
1               5

<210> SEQ ID NO 35
<211> LENGTH: 7
<212> TYPE: PRT
<213> ORGANISM: Sorghum bicolor

<400> SEQUENCE: 35

Cys Ala Thr Ser Ala Ala Ile
1               5

<210> SEQ ID NO 36
<211> LENGTH: 6
<212> TYPE: PRT
<213> ORGANISM: Sorghum bicolor

<400> SEQUENCE: 36

Gly Val Val Gln Ser Val
1               5

<210> SEQ ID NO 37
<211> LENGTH: 6
<212> TYPE: PRT
<213> ORGANISM: Sorghum bicolor

<400> SEQUENCE: 37

Gln Leu Gln Gly Val Ala
1               5

<210> SEQ ID NO 38
<211> LENGTH: 5
<212> TYPE: PRT
<213> ORGANISM: Sorghum bicolor

<400> SEQUENCE: 38

Val Gln Gln Leu Gln
1               5

<210> SEQ ID NO 39
<211> LENGTH: 6
<212> TYPE: PRT
<213> ORGANISM: Sorghum bicolor

<400> SEQUENCE: 39

Val Ala Gln Val Ala Gln
1               5

<210> SEQ ID NO 40
<211> LENGTH: 7
<212> TYPE: PRT
<213> ORGANISM: Sorghum bicolor

<400> SEQUENCE: 40

Met Cys Gly Trp Val Val Gln
1               5

<210> SEQ ID NO 41
<211> LENGTH: 5
<212> TYPE: PRT
<213> ORGANISM: Sorghum bicolor

<400> SEQUENCE: 41

Asp Met Gln Ser Arg
1               5
```

```
<210> SEQ ID NO 42
<211> LENGTH: 5
<212> TYPE: PRT
<213> ORGANISM: Sorghum bicolor

<400> SEQUENCE: 42

Gly Leu Gln Asp Leu
1               5

<210> SEQ ID NO 43
<211> LENGTH: 6
<212> TYPE: PRT
<213> ORGANISM: Sorghum bicolor

<400> SEQUENCE: 43

Ala Met Cys Gly Val Val
1               5

<210> SEQ ID NO 44
<211> LENGTH: 4
<212> TYPE: PRT
<213> ORGANISM: Sorghum bicolor

<400> SEQUENCE: 44

Tyr Leu Arg Gln
1

<210> SEQ ID NO 45
<211> LENGTH: 6
<212> TYPE: PRT
<213> ORGANISM: Sorghum bicolor

<400> SEQUENCE: 45

Thr Pro Cys Ala Thr Ser
1               5

<210> SEQ ID NO 46
<211> LENGTH: 6
<212> TYPE: PRT
<213> ORGANISM: Sorghum bicolor

<400> SEQUENCE: 46

Gln Gly Val Ala Ala Ala
1               5

<210> SEQ ID NO 47
<211> LENGTH: 5
<212> TYPE: PRT
<213> ORGANISM: Sorghum bicolor

<400> SEQUENCE: 47

Ala Gln Val Ala Gln
1               5

<210> SEQ ID NO 48
<211> LENGTH: 4
<212> TYPE: PRT
<213> ORGANISM: Sorghum bicolor

<400> SEQUENCE: 48

Gln Gln Leu Gln
1
```

ANTIOXIDANT PROTEIN HYDROLYSATES AND PEPTIDES FROM CEREAL GRAIN CROPS

CROSS-REFERENCE TO RELATED APPLICATION

The present application claims the priority benefit of U.S. Provisional Application No. 62/754,377, filed Nov. 1, 2018, entitled ANTIOXIDANT PROTEIN HYDROLYSATES AND PEPTIDES FROM CEREAL GRAIN CROPS, incorporated by reference in its entirety herein.

SEQUENCE LISTING

The following application contains a sequence listing in computer readable format (CRF), submitted as a text file in ASCII format entitled "Sequence_Listing," created on Oct. 31, 2019, as 7 KB. The content of the CRF is hereby incorporated by reference.

BACKGROUND OF THE INVENTION

Field of the Invention

The present invention is generally directed to peptides derived from the proteins of cereal grain crops and having desirable antioxidant properties, and methods of producing the same.

Description of the Prior Art

Antioxidants are widely used in food industries to delay lipid oxidation and prevent oxidative deterioration. Antioxidants generally refer to substances capable of delaying or inhibiting oxidation reactions. This may be accomplished through a variety of chemical mechanisms, such as H/e donation (which stabilize free radicals and stop chain reactions), chelation of catalytic transition metals, and providing a physical barrier to hinder or minimize the access to targets.

In recent years, growing interests in developing safe and efficient antioxidants from natural sources due to the health-related risks associated with synthetic antioxidants. Recently, peptide antioxidants have drawn growing interests as since proteins are a macronutrient with various functionalities and high consumer acceptability. Many dietary proteins have been validated for their antioxidant potentials especially those obtained from animal proteins, nuts and pulses. Relatively less information is available on characterizing the antioxidant profile of cereal protein, and even less for sorghum protein. Sorghum is the fifth largest crop worldwide and is the third in United States. U.S. is leading in global sorghum production and distribution, and the state of Kansas is producing nearly half of U.S. sorghum. Currently, about one third of the U.S. sorghum is being used for ethanol production, resulting in more than 450 kilotons of by-products (e.g., dried distiller's grains—DDGS) annually, which were often discarded or underutilized. DDGS is a premium protein source (~30% protein). Therefore, there is a need for cost-efficient ways to produce peptide antioxidants and for high-value uses for DDGS by-products from ethanol production.

SUMMARY OF THE INVENTION

In one embodiment of the present invention, there is provided a method of producing an antioxidant peptide product from a cereal crop material. The method comprises reacting the cereal crop material with an enzyme capable of hydrolyzing proteins within the cereal crop material, thereby forming a hydrolysate peptide mixture. The method further comprises fractionating the hydrolysate peptide mixture and recovering peptides having a molecular weight greater than about 1 kDa, thereby forming the antioxidant peptide product. In another embodiment, there is provided an antioxidant peptide product formed by this method. In another embodiment, there is provided a food product comprising the antioxidant peptide product formed by this method.

In another embodiment, there is provided a hydrolysate peptide formed by reacting a cereal crop material with an enzyme capable of hydrolyzing proteins within the cereal crop material. The hydrolysate peptide has a molecular weight of about 1 kDa to about 10 kDa.

In another embodiment, there is provided a method of forming an antioxidant peptide product comprising synthesizing one or more peptides having an amino acid sequence selected from the group consisting of MDMQ (SEQ ID NO: 1), QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and VAQ.

BRIEF DESCRIPTION OF THE DRAWINGS

Figures (FIGS. 1A, 1B, and 1C are graphs showing screening of microbial origin enzymes for kafirin hydrolysis using Alcalase, Neutrase, Flavourzyme, Everlase and Protamex at protein content of 2%, enzyme-to-substrate ratio of 0.4 Au/g and hydrolyzed for 5 hours and 21 hours, with FIG. 1A showing Total protein recovery (%)

FIG. 2B showing DPPH scavenging activity (%) at 5 mg/mL;

FIG. 3B showing DPPH scavenging activity (%) at 5 mg/mL;

FIG. 4B showing degree of hydrolysis; and FIG. 4C showing DPPH scavenging activity (%) at 5 mg/mL;

FIG. 5B showing degree of hydrolysis; and FIG. 5C showing DPPH scavenging activity (%) at 5 mg/mL;

FIG. 6B showing degree of hydrolysis; and FIG. 6C showing DPPH scavenging activity (%) at 5 mg/mL;

FIG. 8B showing DPPH scavenging activity (%); FIG. 8C showing reducing power capacity at 2.5 mg/mL (Abs at 700 nm); FIG. 8D showing ORAC (g Trolox equiv./g); and FIG. 8E showing metal chelating capacity (%), wherein * Blank represents the absorbance of reaction mixture at 700 nm using distilled water in substitute of sample, and different lowercase letters, capital letters, and roman numerals indicated significant difference at P<0.05;

FIG. 9B showing POV (mM cumene hydroperoxide equivalent); and FIG. 9C showing TBARS (µM tetramethoxypropan equivalent), wherein different lowercase and capital letters indicated significant difference at P<0.05;

FIG. 12B showing DPPH scavenging activity (%) at 4 mg/mL, wherein different lowercase letters indicated significant difference at P<0.05;

FIG. 13B showing degree of hydrolysis; FIG. 13C showing total phenolic content (mg GAE/g); and FIG. 13D showing DPPH scavenging activity (%) at 5 mg/mL;

FIG. 15B showing DPPH scavenging activity (%); FIG. 15C showing ABTS scavenging activity (%); FIG. 15D showing reducing power capacity (Abs at 700 nm); and FIG. 15E showing metal chelating capacity (%), wherein * Blank represents the absorbance of reaction mixture at 700 nm using distilled water in substitute of sample, and different lowercase letters, capital letters, and roman numerals indicated significant difference at P<0.05;

FIG. 16C showing TBARS (µM tetramethoxypropan equivalent), wherein different lowercase and capital letters indicated significant difference at P<0.05;

FIG. 19B showing DPPH scavenging activity (%) at 4 mg/mL; FIG. 19C showing ABTS scavenging activity (%); and FIG. 19D showing ORAC (g Trolox equiv./g), wherein different lowercase letters, capital letters, and roman numerals indicated significant difference at P<0.05;

FIG. 20B showing degree of hydrolysis; FIG. 20C showing total phenolic content (mg GAE/g); and FIG. 20D showing DPPH scavenging activity (%) at 5 mg/mL;

FIG. 22B showing DPPH scavenging activity (%); FIG. 22C showing ABTS scavenging activity (%); FIG. 22D showing reducing power capacity (Abs at 700 nm); FIG. 22E showing metal chelating capacity (%); FIG. 22F showing ORAC (g Trolox equiv./g), wherein * Blank represents the absorbance of reaction mixture at 700 nm using distilled water in substitute of sample, and different lowercase letters, capital letters, and roman numerals indicated significant difference at P<0.05;

FIG. 23B showing POV (mM cumene hydroperoxide equivalent); and FIG. 23C showing TBARS tetramethoxypropan equivalent), wherein different lowercase and capital letters indicated significant difference at P<0.05;

FIG. 26B showing DPPH scavenging activity (%) at 4 mg/mL; FIG. 26C showing metal chelating activity (%); and FIG. 26D showing ORAC (g Trolox equiv./g), wherein different lowercase and capital letters indicated significant difference at P<0.05;

DETAILED DESCRIPTION OF THE PREFERRED EMBODIMENT

Figure 1A:
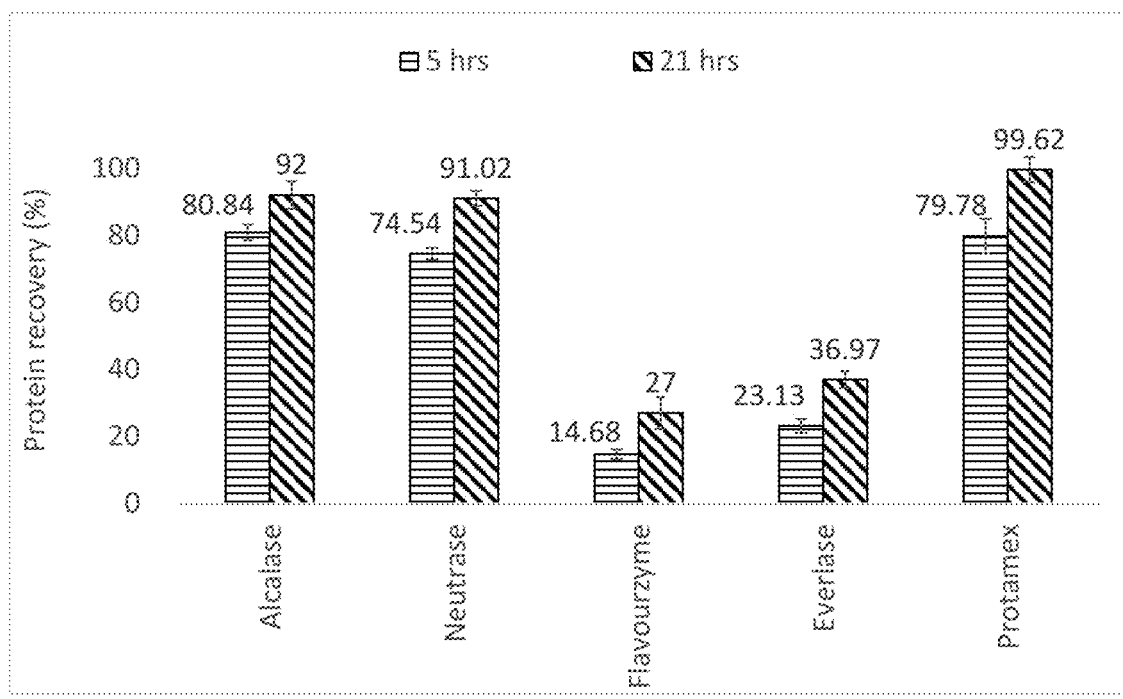
FIG. 1B showing degree of hydrolysis.
FIG. 1C showing DPPH scavenging activity (%) at 5 mg/mL.

Described herein are antioxidant peptide products, and methods of producing the same, which can be derived from cereal (grain) crops and can be used as alternatives to synthetic antioxidants in food and food ingredients, pet food, animal feed, and other applications. The methods of producing the antioxidant peptide products generally comprise reacting the cereal crop material with an enzyme capable of hydrolyzing proteins within the cereal crop material, thereby forming hydrolysate peptides having antioxidant properties.

As noted above, the antioxidant peptide products are produced from a cereal crop material. Thus, the antioxidant peptide products are advantageously derived from plant material, as opposed to synthetically produced. The cereal crop material may comprise any of a number of grains, such as maize (corn), rice (paddy), wheat, barley, sorghum, and the like. However, in certain embodiments, the cereal crop material comprises maize corn or grain sorghum. In certain preferred embodiments, the cereal crop material comprises grain sorghum. Upon harvesting of the cereal crop, the grain kernel generally comprises about 70% to about 80% by weight carbohydrate, about 7% to about 15% by weight protein, and about 2 to about 4% by weight crude fat, with the total weight of the kernel taken as 100% by weight. Other minerals, vitamins, and phytochemicals are typically also present in the kernel. About 40% to about 70% of the protein present in the kernel is prolamin protein. Prolamins are a group of plant storage proteins having a high proline content and found on plant materials mainly, for example, in the seeds of cereal grains such as wheat (gliadin), barley (hordein), rye (secalin), corn (zein), sorghum (kafirin).

The cereal crop material may undergo one or more processing steps prior to reacting with the enzyme. As used herein, the term "cereal crop material" may include unprocessed or processed materials that originate from a cereal crop grain. The processing may include steps for extracting, isolating, and/or concentrating the protein content from the cereal crop, for example to provide a cereal crop material having increased protein concentrations. Such processing steps may include grinding cereal crop kernels to produce a cereal crop flour material, defatting and/or de-oiling the cereal crop material to reduce the crude fat content, and/or isolating the proteins (e.g., prolamin proteins) from the carbohydrate portion of the cereal crop material. By using such steps, the cereal crop material may be provided as a mixture of proteins (i.e., a protein concentrate) that have been extracted from the cereal crop and comprises increased substrate material for reaction with a protease enzyme, as described below. For example, in certain embodiments, the cereal crop material comprises at least about 25% by weight, preferably at least about 50% by weight, and more preferably at least about 75% by weight of protein.

In certain embodiments, the cereal crop material comprises dried distiller's grains (DDGs). Distiller's grains are the cereal by-products of a distillation process, such as ethanol biofuel process, which use mixtures of corn, sorghum, and/or other grains and a fuel source. Since the fermentation uses the carbohydrate in the grains as a fuel source, the by-product DDGs has a greater protein content than the unprocessed grain. Since the protein acts as the substrate material from the enzymatic hydrolysis of the present invention, DDGs can advantageously serve as a high-protein source material for the present invention, while also adding significant value to the DDGs by-product.

The cereal crop material is reacted with an enzyme capable of hydrolyzing proteins within the cereal crop material, which cleaves the proteins into hydrolysate peptides. The reacting step unfolds the 3-D globular protein structures and degrades the long protein amino acid chains into shorter peptides with lower molecular weights. The reacting step also exposes certain functional groups and structural domains that were buried within the hydrophobic core of the protein. A variety of protease enzymes may be used in accordance with the present invention, including microbial-originated proteases, plant-originated proteases, or animal-originated proteases. However, in preferred embodiments, the enzyme is a microbial-originated protease or a plant-originated protease. In certain embodiments, the enzyme is a protease produced by an organism selected from the group consisting of *Bacillus* bacteria, *Aspergillus* fungi, Caricaceae plants (e.g., papaya), *Ficus* plants (*Ficus carica*), Suidae animals (e.g., porcine), and Bovidae animals (e.g., bovine). The particular enzyme can be selected based on the desired peptide chains for the antioxidant product.

Regardless the enzyme, the reaction mixture is generally prepared by dispersing the cereal crop material in a solvent (e.g., distilled water). The protein content of the resulting suspension can impact the recovery of peptides in the antioxidant product. In certain embodiments, the reaction mixture comprises about 1% to about 10% by weight, preferably about 2% to about 6% by weight of protein. The pH of the suspension can then be adjusted to the appropriate acidity for the specific enzyme being used for the hydrolysis reaction. In certain preferred embodiments, the reaction is carried out at a pH of about 5 to about 10, preferably about 6 to about 9. However, a higher or lower pH may be used, depending on the enzyme selected. The enzyme is then added to the suspension, and the reaction mixture can then be agitated. In certain embodiments, the hydrolysis reaction is carried out at a temperature of about 25° C. to about 75° C., preferably about 40° C. to about 60° C. However, the reaction temperature can be varied higher or lower, depending on the enzyme. The reaction is generally carried out for at least 1 hour, preferably about 1 to about 24 hours, more preferably about 2 to about 17 hours, and most preferably about 3 to about 5 hours. The amount of enzyme and substrate (cereal crop material) can be varied depending on the enzyme and reaction conditions. In certain embodiments, the reaction comprises from about 0.1 to about 1 Anson Units of the enzyme per gram of protein in the cereal crop material, preferably from about 0.2 to about 0.8 Anson Units of the enzyme per gram of protein in the cereal crop material, and more preferably from about 0.3 to about 0.5 Anson Units of the enzyme per gram of protein in the cereal crop material.

After the hydrolysis reaction has been carried out for the desired duration, the reaction can be stopped, for example by heating the reaction mixture to a temperature of at least about 75° C., preferably at least about 85° C., and more preferably at least about 95° C., for at least about 5 minutes, preferably at least about 10 minutes, and more preferably at least about 15 minutes. The reaction mixture is then cooled, for example to room temperature, about 10° C. to about 30° C., preferably about 20° C. to about 25° C., and the pH can be adjusted to a neutral pH between about 6 and about 8.

Following hydrolysis, the mixture comprises peptide hydrolysate products having a variety of peptide chain lengths. The hydrolysate peptide mixture is then fractionated, whereby the peptides within the mixture are separated based on molecular weight. The fractionation can be performed using ultrafiltration, gel filtration, or other known methods in the art. During the hydrolysis reaction, the proteins are degraded into hydrolysate peptides having varying chain lengths and molecular weights. The hydrolysate peptides can be generally categorized into small peptides (<1 kDa), medium peptides (1-10 kDa), and large peptides (>10 kDa). The size of the peptides recovered has been shown to have a significant effect on the antioxidant properties of the resulting product, with medium and large peptides being most desirable. Therefore, in certain embodiments, after fractionation the method comprises recovering peptides having a weight average molecular weight greater than about 1 kDa, preferably greater than about 3 kDa, and more preferably greater than about 5 kDa, thereby forming an antioxidant peptide product. In certain embodiments, the recovered peptides have a weight average molecular weight of about 1 kDa to about 20 kDa, preferably about 3 kDa to about 15 kDa, and more preferably about 5 kDa to about 10 kDa. However, in certain embodiments, smaller peptides may be recovered, and the recovered peptides will have a weight average molecular weight of less than about 1 kDa.

The antioxidant peptide products produced using the methods according to embodiments of the present invention have a number of features that make the product advantageous over prior art antioxidants. In certain embodiments, the antioxidant peptide product has a total phenolic content of greater than about 20 milligrams of gallic acid equivalent per gram (mg GAE/g), preferably greater than about 30 mg GAE/g, and more preferably greater than about 40 mg GAE/g. Additionally, certain amino acid sequences are present in increased amounts in peptide chains having particularly favorable antioxidant properties. Therefore, in certain embodiments, the antioxidant peptide product comprises peptides having amino acid sequences MDMQ (SEQ ID NO: 1), VAQ, QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and/or VAQ. In certain embodiments, the antioxidant peptide product comprises a higher occurrence of glutamine (Q) than any other amino acid.

In another embodiment, the present invention includes a method of forming an antioxidant peptide product by synthesizing one or more peptides having desirable having similar functionality to the antioxidant peptide products described above. The peptides may be synthesized using any of a variety of methods known in the art. However, the peptides will generally comprise an amino acid sequence selected from the group consisting of MDMQ (SEQ ID NO: 1), QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and VAQ.

The antioxidant peptide products can be incorporated into food products as an alternative to synthetic antioxidants or as a synergistic ingredient to protect the susceptible ingredients from oxidative spoilage. Therefore, in one embodiment, there is provided a food product comprising the antioxidant peptide product of the present invention. The food product may be any of a variety of foods where an antioxidant component may be desirable. The antioxidant peptide product of the present invention is particularly beneficial in oil-in-water emulsion systems and ground meat model systems. Without being bound by any theory, it is believed that the antioxidant peptide product acts to quench or terminate free radicals, chelate prooxidative catalytic metal ions, electron or proton donating, reducing peroxide products, interrupts the decomposition of hydroperoxide, and/or minimizes physical contact of oxidizing agent to susceptible targets in such systems.

The antioxidant peptide products of the present invention provide a number of advantages over antioxidants of the prior art. The methods described herein provide an efficient, cost-effective process for producing naturally-derived, clean-labeled antioxidants using components that are generally recognized as safe (GRAS) at high dosage. Using cereal crop material as the protein source also provides an energy source and desirable nutritional profile. The antioxidant peptide products described herein have no known toxicity, and little or no side effects. The antioxidant peptide products are also useful for a variety of functionalities in food products, such as solubility, emulsifying, foaming, gelation, oil or water binding capacity.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than or equal to about 10" (with no upper bounds) and a claim reciting "less than or equal to about 100" (with no lower bounds).

EXAMPLES

The following examples set forth production and efficacy testing of antioxidant peptide products in accordance with embodiments of the present invention. It is to be understood, however, that these examples are provided by way of illustration and nothing therein should be taken as a limitation upon the overall scope of the invention.

Example I

Reaction Optimization, Antioxidant Activity Characterization, and Peptides Identification of Sorghum Kafirin Hydrolysates Prepared with Neutrase
Abstract Sorghum kafirin protein was extracted from defatted white sorghum flour and hydrolyzed with different types of enzymes from bacterial, plant and animal origins. Hydrolysate prepared with Neutrase displayed excellent antioxidant activities as well as total protein recovery yield. Therefore, it was primarily selected for further optimization and analysis. Essential reaction parameters in producing these antioxidant peptides include substrate content, enzyme-to-substrate ratio, and hydrolysis time, which will make impacts on the molecular weight distribution, amino acid composition, structural characteristics and functional properties of the resulting peptides. Hydrolysates obtained at optimized conditions (substrate content of 4%, enzyme-to-substrate ratio of 0.4 Au/g, and hydrolysis time of 17 hours) were fractionated by ultrafiltration. Medium-sized hydrolysates (3-10 kDa) were found to possess relatively higher total phenolic content and stronger antioxidative activities with regard to free radical scavenging activity, metal ion chelating activity, reducing power, and oxygen radical absorbance capacity. In an oil-in-water emulsion model system, the selected fraction of hydrolysates incorporated at 50 mg/mL inhibited the formation of primary and secondary oxidation products by 77.14% and 54.34%, respectively, during a 14-day incubation period. In the ground meat model system, the addition of peptides at 0.5 mg/g decreased the lipid peroxidation by 24.16% during a 12-day storage. The selected fraction of hydrolysate with strongest activities was further fractionated by gel filtration chromatography, and the most potent fraction of peptides (F2) was collected and identified for its major peptide compositions and sequences using RP-HPLC and MALDI-TOF/TOF MS. Glutamine and alanine were the top two amino acids found in identified peptide sequences whilst MDMQ (SEQ ID NO: 1) and VAQ the most frequently appeared peptide sequences, which could be vital constituent peptides and/or amino acids for the antioxidant activity of kafirin hydrolysates.

These combined results revealed that our selected sorghum peptides obtained through enzymatic hydrolysis and fractionation can act as efficient antioxidants in real food products to protect oil and fat from oxidative stress. Possible antioxidative mechanisms include free radical scavenging, metal ion chelation, hydrogen donating, reducing hydroperoxides, and forming physical barriers to deter the contact between oxidative agents and susceptible targets. Positive correlation between total phenolic content and antioxidant activities indicated that the peptides with phenolic amino acid residues and phenolic compounds released during hydrolysis contributed largely to their antioxidant activities.

Introduction

Oxidation of oils and fats in food products results in the deterioration of many quality features such as color, flavor, aroma, and texture, which will ultimately shorten the shelf-life and decrease the sensory and nutritional quality. In biological systems, oxidation could cause structure alteration and biological function failures such as destabilization and disintegration of cell membranes, DNA mutation, protein damage, and many age-related diseases including cancer. Antioxidants play an important role in neutralizing and reducing oxidative stress. In food industry, antioxidants are widely used to preserve various food products from oxidation and deterioration, hence, maintain the stability and integrity of qualities, and extend their shelf-life. In human body, antioxidants provide prevention effect of oxidative reactions induced diseases. Chemically synthetic antioxidants such as butylated hydroxytoluene (BHT), butylated hydroxyani sole (BHA), and tert-Butylhydroquinone (TBHQ) are cheap and effective at low dosage thus have been widely used in food industry. However, due to the potential risks to human health such as induction of DNA damage and toxicity, safety concerns over synthetic antioxidants have restricted the use of these compounds. Naturally extracted antioxidants such as green tea extracts and rosemary extracts are found to be effective antioxidants, but they are much more expensive due to the complex manufacturing process and relatively low yield.

In recent years, the interest of research is growing in developing safe and effective natural antioxidants from protein sources. Protein sourced antioxidants can serve as energy source and provide profile of essential amino acids while exerting antioxidative effects in food products. In addition, the unique amphiphilicity of antioxidant peptides allow them to perform oxidation inhibition functions in both aqueous and lipid systems as well as many other functionalities such as surface-active agents, emulsifiers, and foaming agents. All these properties make antioxidative peptides very applicable to food industry. Enzymatic hydrolysis is a predominant approach in producing peptide sequences with good selectivity and high antioxidant activity. Many studies have reported the antioxidative activities of protein hydrolysates. However, few reports have been found on characterizing the antioxidative activities of sorghum protein hydrolysates. Kafirin, the main storage protein of sorghum endosperm, can be obtained by isolating the alcoholic extractant in sorghum protein fractionation which has been proven to be biologically active by several studies. Thus, kafirin is being an attractive source for production of antioxidant peptides with various human health promoting benefits and quality-enhancing functional properties.

This study was designed to utilize the sorghum kafirin as a protein source to produce hydrolysates with antioxidative activities. Reaction parameters involved in hydrolysis will be optimized in turns using single factor methodology, and more than ten types of enzymes of different origins will be screened. The hydrolysates obtained with promising enzymes at optimal conditions will be further fractionated by ultrafiltration and gel filtration chromatography. Peptides in the fraction that showed strongest activities will be identified using mass spectrometry. The antioxidative capacities of the obtained hydrolysates will be evaluated by in vitro assays and will be applied into two different model systems. To summarize, the objectives of this study are to: 1) evaluate the antioxidative performances of the sorghum kafirin enzymatic hydrolysates; 2) optimize the reaction parameters affecting the hydrolysate yield and antioxidative activity for hydrolysis with Neutrase; and 3) study the peptide sequences and molecular structures related to the antioxidative activities of kafirin hydrolysates.

Materials and Methods

Materials and Chemicals

The Harvest Pearl white sorghum flour was kindly provided by ADM Milling Co. (Overland Park, Kans., USA). Alcalase® 2.4 L (Proteinase from *Bacillus licheniformis* Subtilisin A), Flavourzyme® (Protease from *Aspergillus oryzae*), Neutrase® 0.8 L (Protease from *Bacillus amyloliquefaciens*), Everlase 16.0 L (Protease from *Bacillus* sp.), Protamex® (Protease from *Bacillus* sp.), Papain (Papaya latex), and Bromelain (Pineapple stem) were purchased from Sigma-Aldrich (St. Louis, Mo., USA). Another brand of Papain (*Carica papaya*) was bought from EMD Millipore Corporation (Billerica, Mass., USA). Ficin (Fig tree latex) was received from TCI America Co. (Portland, Oreg. USA). Trypsin (Bovine pancreas) was received form Alfa Aesar (Haverhill, Mass. USA). Pepsin (Porcine) was obtained from Acros Organics (New Jersey, USA).

Rosemary leaf extract powder was acquired from Z Natural Foods (West Palm Beach, Fla., USA). 2,2-Diphenyl-1-picrylhydrazyl (DPPH), 2,2'-Azino-bis (3-ethylbenzothiazoline-6-sulfonic acid) diammonium salt (ABTS), 2,2'-Azobis (2-methylpropionamide) dihydrochloride (AAPH), fluorescein, 6-hydroxy-2,5,7,8-tetramethylchroman-2-carboxylicacid (Trolox), Folin & Ciocalteu phenol reagent, sodium tetraborate decahydrate ($Na_2B_4O_7$), and cumene hydroperoxide were from Sigma-Aldrich (St. Louis, Mo., USA). Potassium ferricyanide ($K_3[Fe(CN)_6]$), and L-serine, were purchased from Acros Organics (New Jersey, USA). Sodium dodecyl sulfate (SDS), trichloroacetic acid (TCA), o-phthaldialdehyde (OPA), and dithiothreitol (DTT), were acquired from Thermo Fisher Scientific Inc. (Ottawa, ON, USA).

Unless otherwise specified, all chemicals and solvents were of analytical grade.

Preparation of Sorghum Protein Hydrolysates

Defat of Sorghum Flour

The sorghum flour was extracted three times by mixing with twice volumes of chloroform to remove the oil and crude fat. The flour suspension was mixed on a magnetic stirrer at room temperature. The chloroform was then removed by paper-filtration with vacuum. The filtrate from the three extractant was combined and transferred to a rotary evaporator (IKA®, Wilmington, N.C., USA) to recycle the chloroform. The total crude fat content was determined by measuring the weight difference of flask after distilling chloroform extractant. The flour residue and the flask containing residual fat were kept in a fume hood for 48 hours to evaporate the solvent and then stored in a zippered bag at −4° C. before use.

Kafirin Extraction

Kafirin was isolated from the defatted sorghum flour. Defatted sorghum flour was presoaked in four volumes of 0.5% (w/w) sodium metabisulfite for 16 hours on a magnetic stirrer at 4° C. The suspension was centrifuged (Avanti® J-E high-speed centrifuge, Beckman Coulter Inc., Brea, Calif., USA) at 8200×g, 4° C. for 10 minutes to remove the sodium metabisulfite solutions. The precipitated residue was transferred to another beaker and added with five volumes of glacial acetic acid and stirred for 1 hour at room temperature. After centrifugation at 8200×g, 20° C. for 15 minutes, the supernatant was collected and adjusted to pH of 5.0 with 3 M NaOH in an ice water bath. The resulting suspension was left on benchtop overnight at 4° C. After centrifuging at 8200×g, 4° C. for 20 minutes, the precipitate was collected and rinsed with distilled water three times by centrifuging at 8200×g for 10 min. The obtained protein was lyophilized using a freeze-drier (Freezone 4.5, Labconco Corporation, Corneous City, Mo. USA) and stored in zippered bags at −4° C. for later use. Glutelin can be further extracted from the flour residue by using the sodium borate/sodium hydroxide buffer, which will not be discussed in detail here.

Enzymatic Hydrolysis of Kafirin

Extracted sorghum kafirin protein was dispersed into distilled water in a conical flask on a magnetic stirrer to form a protein suspension. pH of the suspension was adjusted in accordance with enzymes requirements with 1 N HCl and/or 1 M NaOH, and then, enzyme was added to the protein solution. The flask sealed with a rubber stopper was transferred to a water bath shaker (Shel Lab SWBR27, VWR International, LLC., Radnor Pa., USA) and incubated with shaking force. Table 1 summarizes the preliminary recommended reaction parameters for different enzymes used in this study. After reaching the predetermined hydrolysis time, the reaction was stopped by heating the reaction mixture in a boiling water bath for 15-20 minutes. After cooling down, the resulting solution was adjusted to pH of 7.0 with 1 M NaOH and centrifuged at 3500×g, 4° C. for 25 minutes. The supernatant was collected and freeze-dried and was referred to as the protein hydrolysates. The precipitate was freeze-dried and weighed for calculation of total protein recovery.

TABLE 1

Preliminary experiments of sorghum kafirin hydrolysis.

| Enzyme | Origin | Enzyme Unit | pH | T (° C.) | Density | Ratio | Enzyme/g of protein | Time | Recovery (%) | DPPH (%) - 5 mg/mL |
|---|---|---|---|---|---|---|---|---|---|---|
| Neutrase | *Bacillus amyloliquefaciens* | 0.8 U/g | 7.0 | 45 | 1.26 g/ml | 0.4 Au/g | 0.39682 ml | 21 hours | 91.02 | 42.57 |
| Flavourzyme | *Aspergillus oryzae* | 500 U/g | 5.0-7.0 | 50 | 1.27 g/ml | 10 Au/g | 0.015748 ml | 21 hours | 27.00 | 31.25 |
| Alcalase | *Bacillus licheniformis* | 2.4 U/g | 8.3 | 50 | 1.18 g/ml | 0.4 Au/g | 0.14124 ml | 21 hours | 92.00 | 14.09 |

TABLE 1-continued

Preliminary experiments of sorghum kafirin hydrolysis.

| Enzyme | Origin | Enzyme Unit | pH | T (° C.) | Density | Ratio | Enzyme/g of protein | Time | Recovery (%) | DPPH (%) - 5 mg/mL |
|---|---|---|---|---|---|---|---|---|---|---|
| Everlase | *Bacillus* sp. | 16 U/g | 8.0 | 50 | 1.27 g/ml | 0.4 Au/g | 19.685 ul | 21 hours | 36.97 | 39.35 |
| Protamex | *Bacillus* sp. | 1.5 U/g | 7.0 | 50 | / | 0.4 Au/g | 0.26667 g | 21 hours | 99.62 | 15.23 |
| Papain - Sigma | Papaya latex | 1.5-10 U/mg | 6.0-7.0 | 50 | / | 180 U/g | 120 mg | 5 hours | 74.02 | 40.15 |
| Papain - EMD | *Carica papaya* | 31850 U/mg | 6.0-7.0 | 50 | / | 360 kU/g | 56.514 mg | 4 hours | 77.89 | 37.52 |
| Bromelain | Pineapple stem | 1200 GDU/g | 3.0-6.5 | 45-65 | / | 180 kU/g | 150 mg | 5 hours | 71.89 | 49.95 |
| Ficin | Fig tree latex | 680 MCU/mg | 5.0-7.5 | 50-55 | / | 60 kU/g | 225.5 mg | 5 hours | 67.48 | 48.23 |
| Trypsin | Bovine pancreas | 2500 USP/mg | 7.0-9.6 | 37 | / | 25 kU/g | 10 mg | 5 hours | 14.30 | 41.82 |
| Pepsin | Porcine | 400 U/mg | 1.5-1.6 | 37 | / | 25 kU/g | 62.5 mg | 5 hours | 64.60 | 65.45 |

Fractionation and Identification of Antioxidative Peptides

Ultrafiltration with Centrifugal Tubes

Peptide fractions with different molecular size ranges were separated from the hydrolysate mixture through centrifugation by sequentially loading into Amicon® Ultra-15 Centrifugal Filter Devices (EMD Millipore Corporation, Billerica, Mass., USA) at molecular weight cut-off of 3 kDa and 10 kDa. The processing time for 10 kDa and 3 kDa centrifugal filters is 23 minutes and 55 minutes, respectively, at 4° C., 3500×g. Permeates and retentate with different Mw were obtained as followed: <3 kDa fraction, 3-10 kDa fraction, and >10 kDa fraction. Along with the initial hydrolysates that did not go through ultrafiltration, the four fractions of hydrolysates were collected and lyophilized respectively for later analysis.

Gel Filtration Chromatography

The aforementioned hydrolysates (100 mg) prepared at optimized reaction conditions were dissolved in 3 mL deionized water and loaded onto a Sephadex G-25 (medium) gel filtration column (26 mm×850 mm) which had been previously equilibrated with deionized water. A total portion of 600 mL deionized water was used to elute the sample, and aliquots of 3 mL were collected at a gravity-driven flow. The absorbance of collected fractions was measured at 280 nm to determine the elution profile. Fractions of eluent making up major peaks were combined into several fractions and lyophilized for analysis.

Identification of Representative Peptide Sequences from Gel Filtration

Trypsin Digestion and MALDI-TOF/TOF MS Analysis of Kafirin Crude extracted kafirin was dissolved in 100 μL DTT (15 μg/mL) for 30 minutes at 80° C. 100 μL iodoacetamide (18 μg/mL) was then added. The mixture was placed in the dark and incubated for 1 hour at room temperature. The proteins were then digested with 10 μL of trypsin (1 μg/30 μL, Trypsin Gold, mass spectrometry grade; Promega Corp., Madison, Wis.) overnight at 37° C. Digested kafirin solutions were spotted in a 2,5-dihydroxybenzoic acid (DHB) matrix (Sigma-Aldrich, St. Louis, Mo.) on a Bruker Ultraflex III Matrix-Assisted Laser Desorption Ionization—Time of Flight/Time of Flight Mass Spectrometry (MALDI-TOF/TOF MS) (Bruker Daltonik GmbH, Bremen, Germany). Spectra were obtained in positive ion reflection mode at 66.7 Hz with 1000 laser shots per spectrum. Spectra were analyzed using FlexAnalysis (version 3.3, Bruker Daltonik GmbH) and internally calibrated with DHB matrix peaks. Known alpha, beta, and gamma kafirin protein sequences were obtained from http://www.uniprot.org. Using mMass (http://www.mmass.org) software, these sequences were analyzed allowing for up to 4 missed cleavages, a peptide mass tolerance of 0.55 Da, and variable modifications of carbamidomethyl (C) and oxidation (W, M). The spectrum from the trypsin cleavage of the proteins was compared to the known theoretical sequence cleavage results.

HPLC Peak Collecting and Sequence Analysis of Gel Filtration Sample

Samples of lyophilized fractions from gel filtration were analyzed using reverse phase high performance liquid chromatography (RP-HPLC) on a Beckman machine running 32 Karat (version 8.0) software with a C8 column (Buffer A: 99.9% water and 0.1% TFA; Solvent B: 90% Acetonitrile, 9.9% water, and 0.1% TFA) with a 10% to 50% Buffer B gradient over 30 minutes. Peaks from the RP-HPLC runs were manually collected and analyzed using the same MALDI-TOF/TOF MS procedure as described for crude kafirin. The spectra obtained were compared to beta kafirin protein sequences (http://www.uniprot.org). These protein sequences were cleaved using non-specific cleavage sites that resulted in peptides between 500 and 3,000 Da, and masses were compared to the spectra from the HPLC peaks using a peptide mass tolerance of 0.55 Da.

Evaluation of Hydrolysis Process

Total Protein Recovery

Total protein recovery was an indicator of the yield of hydrolyzed water-soluble peptides released from water-insoluble intact proteins. Total protein recovery was determined by the percentage of the hydrolysates to the initial protein by excluding the unhydrolyzed protein obtained through centrifuging the resulting reaction mixture:

$$\text{Total protein recovery} = \frac{W_i - W_p}{W_i} \times 100\%$$

where $W_i$ was the weight of initial protein, and $W_p$ was the weight of lyophilized precipitate from centrifuging the resulting mixture at the end of hydrolysis.

Degree of Hydrolysis

Degree of hydrolysis (DH) is defined as the percentage of hydrolyzed peptide bonds to the number of total bonds per unit weight of the substrate protein, which is a typical indicator of the extent of hydrolysis degradation. The value of DH can also be used for comparison among different protein hydrolysates. DH in this study was determined using OPA method. Basically, OPA reagent was prepared by dissolving 7.62 g $Na_2B_4O_7$ and 200 mg SDS in 150 mL deionized water and then added with 160 mg OPA dissolved in 4 mL ethanol. 176 mg DTT was added to the above solution and the total volume was equilibrated to 200 mL with deionized water. The serine standard solution was prepared by dissolving 50 mg serine in 500 mL deionized water (0.9516 meqv/L). 400 µL of the hydrolysate sample at 1.2 mg/mL was added to 3 mL of OPA reagent and vigorously mixed for 5 seconds. The absorbance of the mixture was measured at 340 nm on a spectrophotometer (UV-6300PC, VWR International, LLC., Radnor Pa., USA) after standing for exactly 2 minutes at room temperature. 400 µL of serine standard or deionized water instead of sample was measured using the same procedure and the means of triplicates denoted as standard and blank, respectively, were used for calculations. DH (%) was calculated as followed:

$$SerineNH_2 = \frac{A_{sample} - A_{blank}}{A_{standard} - A_{blank}} \times 0.9516 / (X \times P)$$

where $A_{sample}$ was the absorbance of sample, $A_{standard}$ was the absorbance of serine standard, $A_{blank}$ was the absorbance of deionized water, X=1.2 mg/mL sample concentration; P=100% protein purity; $SerineNH_2$ represents meqv serine $NH_2$/g protein;

$$h = \frac{SerineNH_2 - \beta}{\alpha}$$

where α=1, β=0.4, h represents meqv/g protein; degree of hydrolysis was calculated as:

$$DH = \frac{h}{h_{tot}} \times 100\%$$

where $h_{tot}$=8.3 mmol/g.

Total Phenolic Content

The total phenolic content (TPC) was determined using the Folin-Ciocalteu procedure. Generally, 1 mL 1:10 (v/v) Folin-Ciocalteu reagent and 3 mL 7.0% (w/w) $Na_2CO_3$ was sequentially added to 1 mL of sample solution at 1.0 mg/mL. The absorbance of the reaction mixture was measured at 760 nm after incubated for 30 minutes in darkness at room temperature. Distilled water was used as a blank control, and gallic acid was used in generation of a standard curve. The total phenolic content in sample was expressed as mg gallic acid equivalents per gram of sample (mg GAE/g).

Assessment of Antioxidative Activity

DPPH Radical Scavenging Activity

DPPH radical scavenging activity (DPPH %) was determined by the percentage of decrease in DPPH radical concentration. Briefly, 0.02 mM DPPH reagent was prepared freshly by dissolving 7.88 mg of DPPH in 100 mL 95% (v/v) ethanol. 4.8 mL of sample dissolved in with deionized water at varied concentration (1-10 mg/mL) was mixed with equal volume of DPPH reagent. The reaction mixture was incubated in darkness for 30 minutes at room temperature before reading absorbance at 517 nm. Deionized water without sample was set as a blank control. DPPH is a free radical that has an intrinsic purple color which can be detected at 517 nm. The reduction of DPPH radicals by samples was expressed as percentage of decrease in absorbance at 517 nm as compared to a blank control. DPPH radical scavenging activity was calculated as:

$$DPPH \% = \frac{A_b - A_s}{A_b} \times 100\%$$

where $A_b$ was the absorbance of blank and $A_s$ was the absorbance of sample.

Oxygen Radical Absorbance Capacity

Oxygen radical absorbance capacity (ORAC) assay measures the effect of antioxidant on delaying the decline of fluorescence induced by a peroxyl radical generator, AAPH. The assay was performed using a Biotek® Synergy H1 Hybrid Microplate Reader (Winooski, Vt., USA). Fluorescein was used as the fluorescent probe. Except for hydrolysate samples and Trolox standards, which were dissolved in deionized water, all other reagents were prepared with 75 mM phosphate buffer (pH=7.4). 100 µL 6 nM fluorescein solution was added to 50 µL sample solution. The mixture was incubated at 37° C. for 30 minutes. Then, 50 µL 76.5 mM AAPH solution was added to the previous mixture. The fluorescence of the reaction mixture was recorded every minute for 2 h at 37° C. with excitation and emission wavelengths were 485 and 528 nm, respectively. Trolox was used as standards to generate a standard curve under the same experimental conditions. ORAC values for samples were expressed as gram of Trolox equivalent per gram of sample (g Trolox equiv./g) by comparing the relative area under the sample curve to the Trolox standard curve.

Ferric Ion Reducing Power

The reducing power assay measures the ability of the antioxidant to reduce ferric ion to ferrous ion, which indicates the antioxidant's capacity in donating an electron or hydrogen. Briefly, hydrolysates dissolved in 4 mL 0.2 M phosphate buffer (pH=6.6) were added with 4 mL 1% (w/v) potassium ferricyanide ($K_3[Fe(CN)_6]$). The mixture was incubated at 50° C. for 20 minutes, after which 4 mL of 10% (w/v) trichloroacetic acid was added. The reaction mixture was centrifuged at 3500×g, 20° C. for 10-15 minutes and 4 mL of the supernatant was transferred. Finally, 4 mL of deionized water and 0.8 mL of 0.1% (w/v) ferric chloride were added to the reactant supernatant. After 10 minutes incubation at room temperature, the absorbance of the resultant mixture was measured at 700 nm. Distilled water was set as blank. A larger increased absorbance of the sample over blank indicates a stronger reducing power.

Metal Chelating Capacity

The metal chelating capacity was determined. Generally, 1 mL of sample solution at different concentrations (1-10 mg/mL) was pre-mixed with 0.05 mL of 2 mM $FeCl_2$ solution, then, 2 mL of distilled water was added to the mixture and the solution was mixed vigorously on a Vortex mixer (Vortex-Genie 2, Scientific Industries, Inc., Bohemia N.Y., USA). Then, 0.1 mL ferrozine solution at 5 mM was added to the previous reaction mixture. The absorbance of the final solution was measured at 562 nm after 10 minutes' incubation at room temperature. Distilled water was used as a blank control. The metal chelating ability was calculated as:

$$Metal\ Chelating\ \% = \frac{A_c - A_s}{A_c} \times 100\%$$

where $A_s$ and $A_c$ represent the absorbance of sample and control, respectively.

Inhibition of Lipid Oxidation in an Oil-in-Water Emulsion System

Emulsion Preparation and Incubation

The edible oils are easily oxidized during processing, storage, and cooking. An oil-in-water emulsion system is suitable to mutate the chemical, physical and environmental conditions in real food products, and the lipid autoxidation and peroxidation can be therefore monitored. The oil-in-water emulsion samples were prepared. Briefly, 250 mg and 500 mg of kafirin hydrolysates were suspended in 45 mL of 0.1 M phosphate buffer (pH=7.0) in 100 mL cap-screwed bottles. The protein solutions were sequentially added with 5 mL soy oil and 0.45 mL Tween 20. The final concentrations of hydrolysates were 50 mg and 100 mg per mL of soy oil (50 mg/mL & 100 mg/mL), respectively. The mixture was blended with a homogenizer (PowerGen 700, Fisher Scientific Inc., Ottawa ON, USA) for 2 minutes followed by passing through a high-pressure microfluidizer (Microfluidics Corp, MA, USA) twice at 30,000 psi to obtain final fine emulsions. For comparison, a blank control containing all other reagents at same emulsifying conditions except for hydrolysates was also prepared. The three obtained emulsions (blank, 50 mg/mL, and 100 mg/mL) were transferred to 50 mL cap-screwed tubes and were incubated in a dark oven (Gravity Convection General Incubator, VWR International, LLC., Radnor Pa., USA) set at 37° C. for autoxidation. A few drops of 3 mM sodium azide were added as a microbial preservative, and the oxidative stabilities were evaluated by measuring the accumulation of hydroperoxide values (POV) and thiobarbituric acid reactive substances (TBARS) at 0, 2, 4, 6, 8, 10, 12, and 14 days of incubation, respectively.

Emulsion Turbidity and Stability

The emulsion turbidity and stability were determined. 25 µL of the obtained fine emulsion was transferred to 7 mL of 0.1% SDS solution immediately after the emulsion was formed, and the absorbance of the mixture was monitored at 500 nm on a spectrophotometer. After 180 minutes, this value was monitored again using the same procedure. The absorbance at time 0 minute was interpreted as emulsion turbidity. The emulsion stability was defined as the percentage of turbidity ratio of 180 minutes to 0 minute.

Lipid Hydroperoxide Values

Lipid hydroperoxide values (POV) were determined using a ferric thiocyanate method. 0.3 mL of the incubated emulsion was added with 1.5 mL isooctane/2-propanol (3:1, v/v) and the slurry was vigorously swirled on a vortex three time for 10 seconds. The organic solvent phase (supernatant) was separated by centrifugation at 2000×g for 2 minutes. 200 µL of the supernatant was transferred to 2.8 mL of methanol/1-butanol (2:1, v/v). Meanwhile, a ferrous chloride solution was freshly prepared by mixing equal amount of 0.132 M $BaCl_2$ and 0.144 M $FeSO_4$ and excluding the precipitate through centrifugation at 3000×g for 3 minutes. The ferrous chloride solution was mixed with equal amount of 3.97 M ammonium thiocyanate, and 30 µL of this mixture was added to the methanol/1-butanol solution containing emulsion extractant. The absorbance of the resulting mixture was monitored at 510 nm after 20 minutes of incubation at room temperature on spectrophotometer. POV was determined using a standard curve made from cumene hydroperoxide and was expressed as mM cumene hydroperoxide equivalent. The inhibition rate of emulsion sample added with hydrolysates was calculated by percentage decrease in POV concentration from blank control.

Thiobarbituric Acid Reactive Substances

The accumulation of secondary reaction products thiobarbituric acid reactive substances (TBARS) was determined by mixing 0.3 mL of the incubated emulsion sample with 0.7 mL of deionized water and 2 mL of TBA reagent containing 15 g of trichloroacetic acid (TCA), 0.375 g of 2-thiobarbituric acid (TBA), and 1.76 mL of 12 N HCl in 82.9 mL of distilled water. The mixture was heated in a boiling water bath for 15 minutes and then cooled to room temperature for 10 minutes in a cool water bath. After cooled down, the mixture was centrifuged at 3500×g for 15 minutes and the absorbance of upper layer was determined at 532 nm after 10 minutes standing at room temperature. The concentration of TBARS was calculated against a standard curve prepared with 1,1,3,3-tetramethoxypropane and expressed as µM tetramethoxypropan equivalent. The inhibition rate of emulsion sample added with hydrolysates was calculated by percentage decrease in TBARS concentration from blank control.

Inhibition of Lipid Oxidation in a Meat System

Meat Preparation

The kafirin hydrolysates fraction from ultrafiltration exhibited stronger antioxidative activities in previous assays were further evaluated for their performances against lipid peroxidation in a ground pork model system according to a protocol described by Zhang et al. (2010). Fresh ground pork was purchased and was stored at 4° C. before use. Kafirin hydrolysates were dispersed in 5 mL distilled water and then transferred to 50 g of ground pork to reach final concentrations of 0.5 mg and 1.0 mg hydrolysate per gram of meat. The homogenized samples were added with a few drops of 3 mM sodium azide before transferred to 100 mL glass bottles with screwed caps and centrifuged at 100×g, 4° C. for 10 minutes to eliminate trapped air. The meat samples were stored at 4° C. refrigerator until analysis. Distilled water was incorporated to the ground meat as a blank control, and rosemary extracts at 0.5 mg/g was used as a positive control. The extent of lipid peroxidation was quantified by measuring TBARS on 0, 1, 2, 4, 6, 8, 10, and 12 days during incubation period.

Thiobarbituric Acid Reactive Substances

The concentration of secondary reaction products thiobarbituric acid reactive substances (TBARS) was measured as an indicator of lipid peroxidation extent. Briefly, the meat sample at certain days of incubation was gently blended with a glass rod before weighting out 5 g of sample. The sample was added with 50 ml of distilled water, 0.1 mL of 10% sodium dodecyl sulfate (SDS) solution, and 10 mL of reducing solution containing 0.01% propyl gallate and 0.02% ethylenediaminetetraacetic acid (EDTA). The meat sample containing above reagents was thoroughly homogenized in a blender (Oster®, Boca Raton, Fla., USA) at high speed for 60 seconds. 1 mL of the resulting homogenate, in triplicate, was immediately transferred into a 15 mL centrifuge tube and was added with 4 mL of TBA buffer containing 0.4% TBA, 0.5% SDS, and 9.3% acetic acid. The mixture was vigorously stirred on a vortex for 15 seconds and then heated in a boiling water bath for 60 min. After cooling, 5 mL of pyridine/n-butanol (1:15, v/v) was added and mixed on a vortex. After centrifugation at 3500×g, 4° C. for 15 minutes, the upper organic layer was collected and monitored for absorbance at 532 nm on a spectrophotometer. 1,1,3,3-teramethoxypropane (TMP) solutions were prepared at 0.0, 2.5, 5.0, 7.5, and 10.0 µM to generate a standard curve, and the coefficient was used to convert absorbance values into TBARS. The final TBARS value was expressed as mg malonaldehyde equivalents per kg of sample (mg MDA equiv./kg). The inhibition rate of meat sample added with hydrolysates or rosemary extract was calculated by percentage decrease in TBARS concentration from blank control.

Statistical Analysis

The data were analyzed using SAS software version 9.3 (SAS Institute, Cary N.C., USA). Results were evaluated by one-way analysis of variance (ANOVA). Tukey's post-hoc test was used to assess the significant differences among individual data set. The results were illustrated as means±standard deviation (n=3) and were considered as significant at $P<0.05$.

Results and Discussion

Kafirin Extraction

The extracted kafirin obtained from glacial acetic acid extractant along with other protein samples from fractional extraction was analyzed for their protein content using nitrogen combustion analysis with LECO FP-2000 nitrogen analyzer (St. Joseph, Mich.) (Table 2). The protein content was calculated based on nitrogen content using a conversion factor of 6.25. The total protein content of the white sorghum flour was 9.33%. The defatted sorghum flour was found to have a lower protein content than original flour as 8.27%, which might be due to the partial loss of protein removed by the organic solvent during defatting. Crude kafirin obtained from different batches of extraction were combined and had a protein content of 97.31%. The end-up extraction rate of kafirin from the sorghum flour was 4.95±0.111% on a weight basis. The total crude fat content was determined to be 0.5125% on a weight basis percentage.

TABLE 2

Protein content of sorghum flour and extracted fractions.

| Sample | Nitrogen (%) | Protein (%) * |
|---|---|---|
| Ardent Mills sorghum flour | 1.493 | 9.333 |
| ADM defatted sorghum flour | 1.323 | 8.269 |
| Kafirin (glacial acetic acid fraction) | 15.570 | 97.313 |
| Glutelin (Borate/NaOH buffer fraction) | 10.804 | 67.525 |
| Sorghum residue after protein extraction | 0.098 | 0.612 |

* Used conversion factor of 6.25.

Reaction Optimization of Kafirin Enzymatic Hydrolysis

Enzyme, protein substrate, and the hydrolysis conditions (time, pH, temperature, etc.) altogether imposed a synergistic impact on the yield and bioactivity of protein hydrolysates. Five bacterial originated enzymes, two animal originated enzyme and three plant originated enzymes were preliminary screened in obtaining antioxidative hydrolysates. Further, the substrate content, enzyme-to-substrate ratio, and hydrolysis time were optimized individually using single factor methodology.

Total protein recovery rate and degree of hydrolysis (DH) were measured as key indicators in evaluating the total yield of the water-soluble hydrolysates as well as the production of short-chained polypeptides. DPPH radical scavenging activity assay has been widely used in evaluating the antioxidant capacities, which can be used as a primary screening method in evaluating the abilities of hydrolysates to act as electron donors in antioxidative performances.

Enzyme Screening

The type of enzyme applied to the substrate plays a dominant role in determination of the properties of hydrolysates. Due to the specificity of enzyme, different cleavage positions on polypeptides chain resulted in uniqueness of hydrolysates in amino acid sequences, peptide lengths, structural characteristics that influencing the antioxidative properties of hydrolysates.

Five bacterial originated enzymes Alcalase, Flavourzyme, Neutrase, Everlase, and Protamex were primarily selected to hydrolyze kafirin at substrate content of 2%, enzyme-to-substrate ratio of 0.4 Anson Units per gram of protein (Au/g). The hydrolysis performed with each enzyme was carried out at the optimal pH and temperature conditions (Table 1). The reaction was stopped after 5 hours by deactivating enzyme at 92° C. for 15-20 minutes.

Figure 1B:
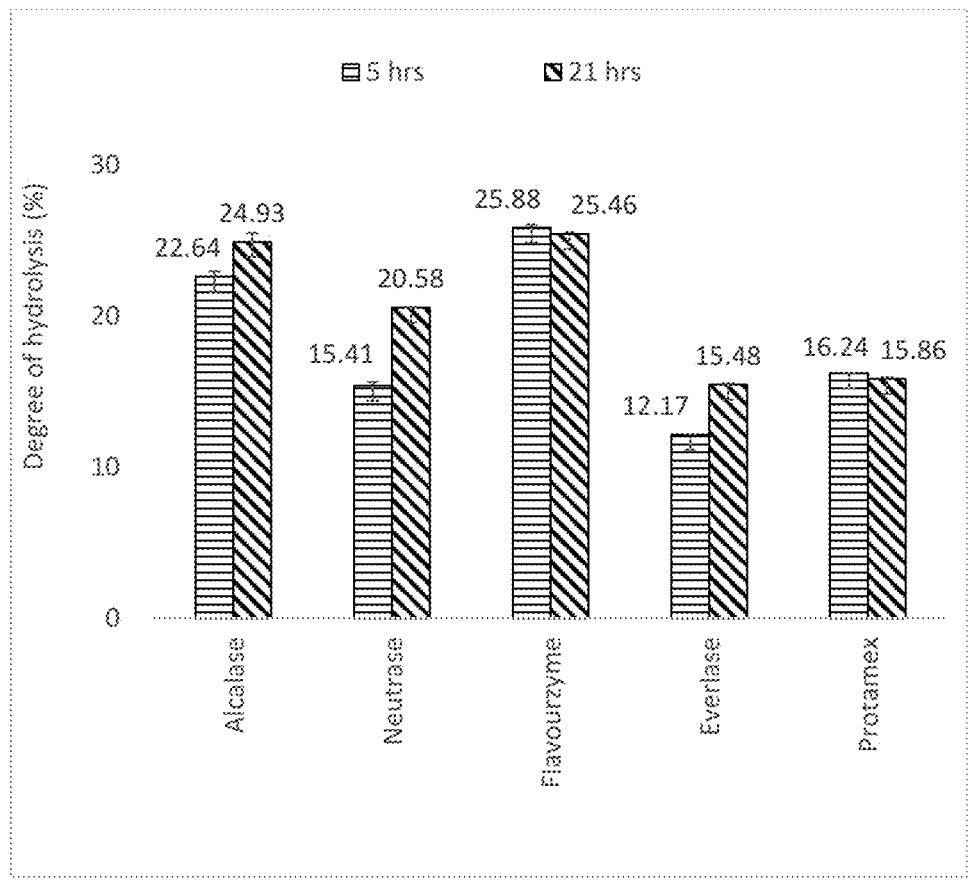
Figure 1C:
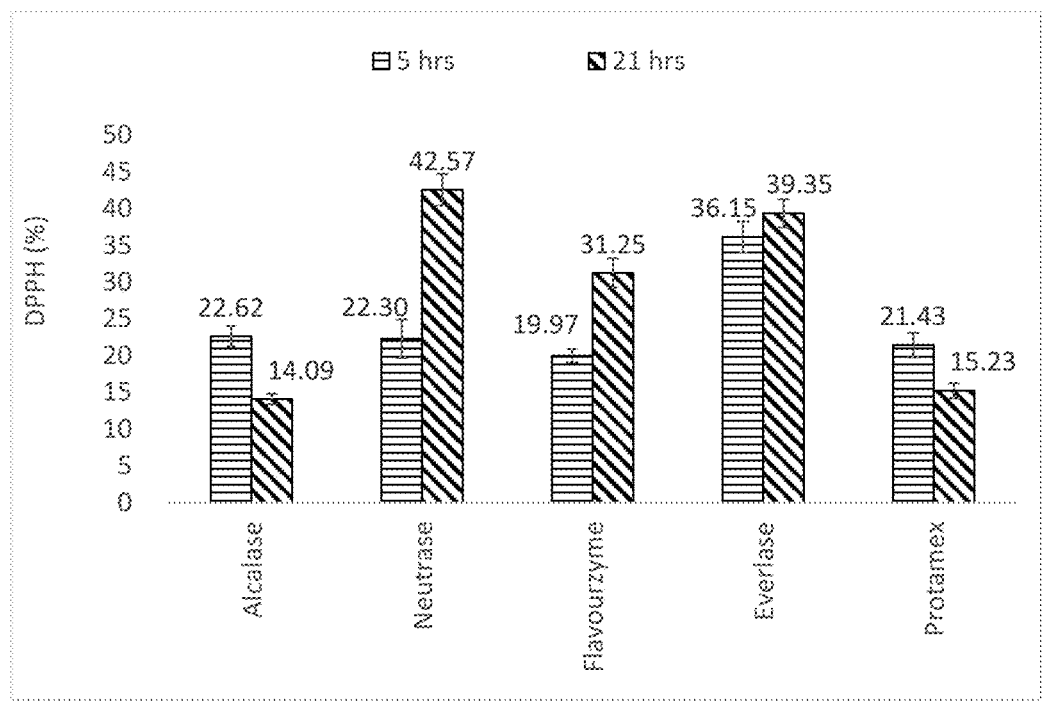

FIGS. 1A-1C show the protein recovery yield, DH, and DPPH % of the hydrolysates obtained by treatment with five different bacterial originated enzymes. Protein recovery percentage is the indicator of total yield of the water-soluble peptides, which was obtained by centrifuging the resulting reactant mixture and collecting the supernatant, which was freeze-dried and was generally regarded as hydrolysates. The protein recovery percentage tended to increase with prolonged hydrolysis time. Hydrolysate prepared with Alcalase, Neutrase, and Protamex led to higher yield, while Flavorzyme and Everlase resulted in extremely low yield, which was due to the different of protease. For example, endo-protease nature of Neutrase that it randomly cleaves the internal peptide bonds. During hydrolysis, the molecular weight of protein was decreased to short-chained peptides with more charged groups ($NH_3^+$ and $COO^-$) exposed through cleavage of peptide linkage, which improve the solubility and the consequent recovery yield.

DH indicates the percentage of cleaved peptide bonds to total peptide bonds and is associated with lots of properties including peptide size, amino acid composition, and biological activities of peptides. Thus, it is important to control the DH for preparation of reproducible hydrolysates with desired functional and biological properties. Hydrolysates prepared with Flavourzyme had the highest DH (25.88±0.21%) and hydrolysates prepared with Everlase had the lowest DH (12.17±0.01%) for 5 hours of hydrolysis. Flavourzyme is a fungal protease complex that contains both endo-peptidase and exo-peptidase, which might be responsible for the higher DH compared to other endo-protease only proteases.

The ability of an antioxidant in donating electron to free radicals and further interrupt the radical mediated lipid chain oxidation is an important indicator of antioxidant capacity. DPPH is a radical that was commonly used to imitate the free radicals present in biological tissue and therefore used to evaluate the electron donating ability of a sample. All five kafirin hydrolysates exhibited some extent of DPPH radical scavenging abilities, which indicated that some peptides within the hydrolysates were potential radical scavengers. Hydrolysates prepared with Neutrase and hydrolyzed for 21 hours exhibited the highest radical scavenging activity (42.57±2.13%), followed with hydrolysates prepared with Everlase (39.35±1.92) and Flavourzyme (31.25±2.00%). The activities of unhydrolyzed kafirin was not tested as it formed a turbid solution even at low concentration due to low solubility in water.

Figure 2A:
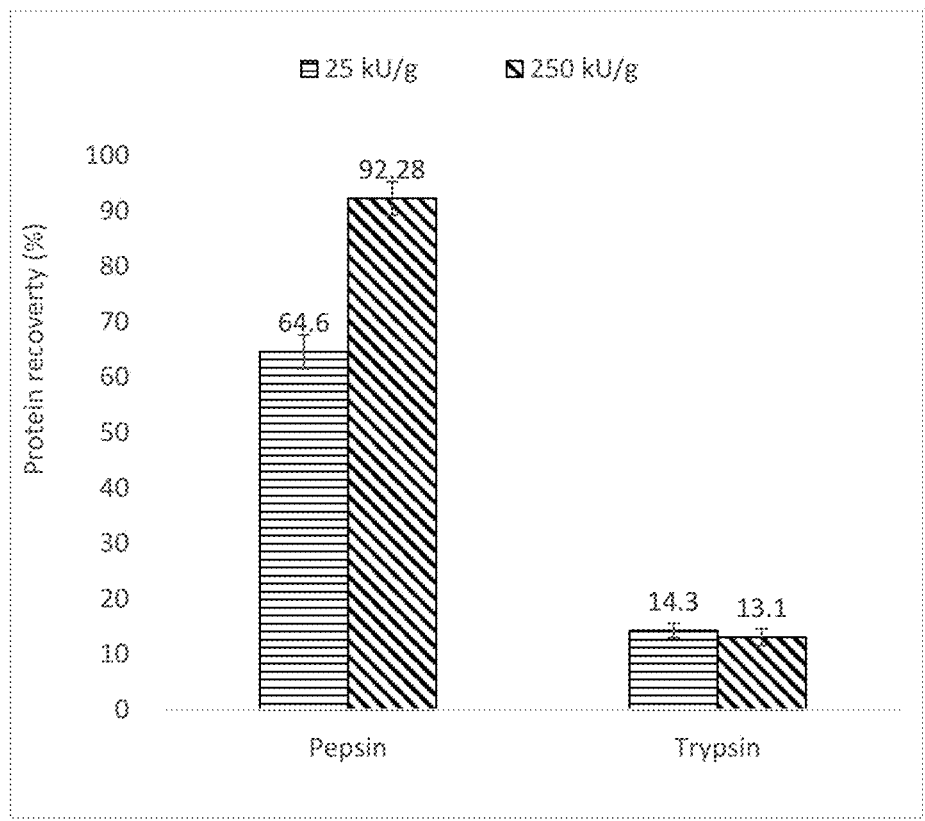
FIGS. 2A and 2B are graphs showing animal origin enzyme screenings of kafirin hydrolysis using porcine Pepsin and bovine Trypsin at protein content of 4%, with enzyme-to-substrate ratios of 25 kU/g and 250 kU/g and hydrolyzed for 5 hours, with FIG. 2A showing Total protein recovery (%)
Figure 2B:
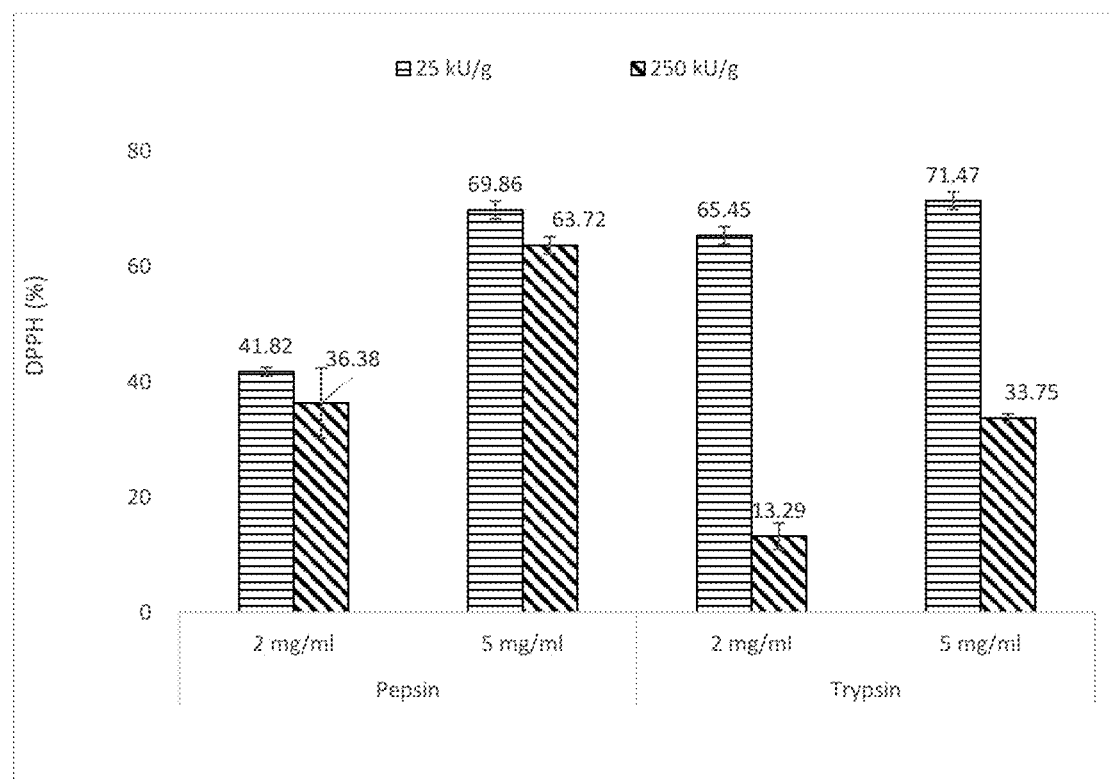

Trypsin and pepsin are animal-originated enzymes which were typically used to hydrolyze animal proteins. It was found that kafirin hydrolyzed with pepsin and trypsin had relatively lower protein recovery rates as compared to microbial-originated proteases (FIGS. 2A and 2B). Especially for hydrolysate prepared with trypsin, it was observed that with ten times of enlargement in enzyme use, no significant improvement on protein recovery was detected. The increased amount of trypsin also largely decreased the DPPH % of hydrolysates. Canola meal proteins hydrolyzed with pepsin has a low yield compared to that of several other enzymes. This might be imputable to the specificity nature of the pepsin as it mainly breaks the peptide bonds in macro-proteins between hydrophobic and cleaves aromatic amino acids. Meanwhile, trypsin not only hydrolyzed the peptide chains mainly at the carboxyl side of the amino acid into oligopeptides, but they also produced more free amino acids due to its greater hydrolysis activities. Thus, these specific properties might lower their yield of kafirin hydrolysate.

Figure 3A:
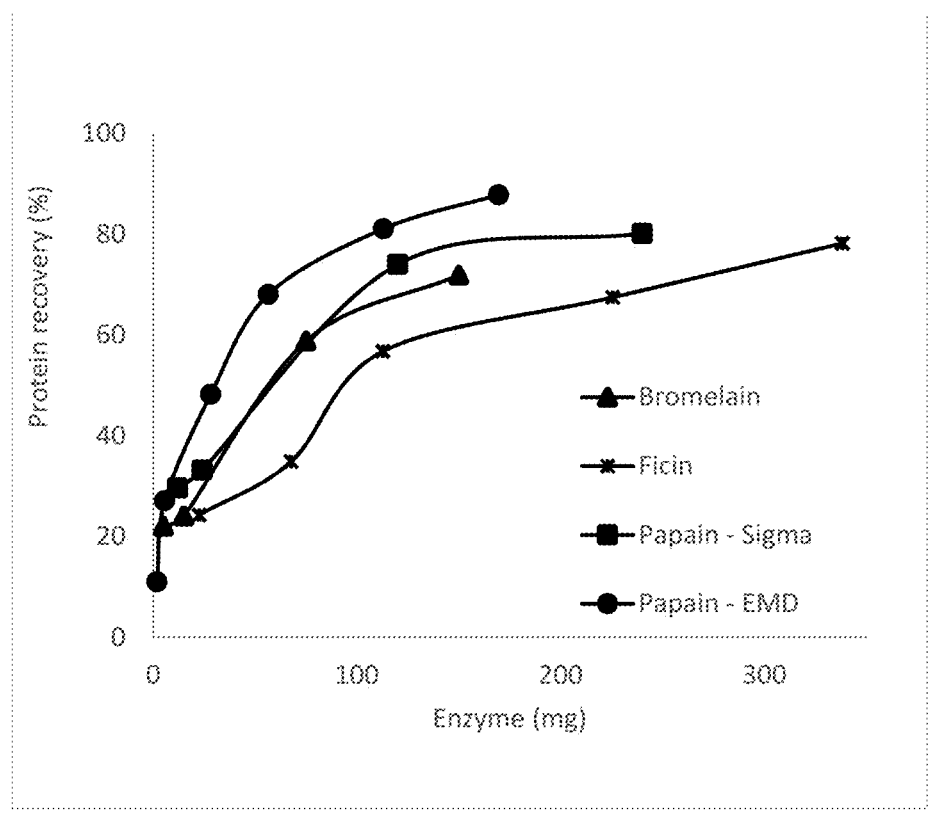
FIGS. 3A and 3B are graphs showing plant origin enzyme screenings of kafirin hydrolysis using Bromelain, Ficin, Papain obtained from Sigma and Papain obtained from EMD at protein content of 4% and hydrolyzed for 5 hours, with FIG. 3A showing Total protein recovery (%)
Figure 3B:
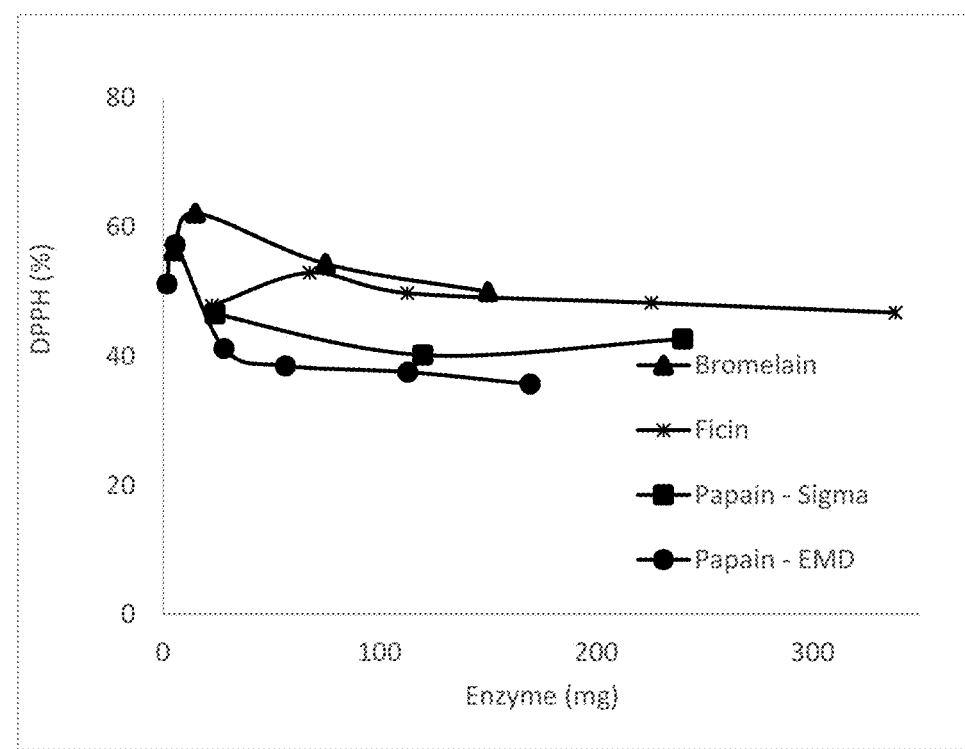

Bromelain, Ficin, and Papain are plant-originated protein enzymes. Due to the inconsistency of enzyme units, the efficacy of different enzyme was compared on a weight basis given the same time of hydrolysis (FIGS. 3A and 3B). It was found that Papain purchased from EMD yielded highest protein recovery rate with minimum amount of enzyme applied. The DPPH % of hydrolysate prepared with Papain EMD were also competitive. Thus, it was selected for future study as described in Example III.

The results above demonstrated that type of enzyme used is a key factor in determining total yield and antioxidative activities of resulting hydrolysates due to the specificity of enzyme. Overall, microbial-originated and plant-originated proteases are more preferred than animal-originated enzymes. Microbial-originated proteases are most efficient regarding total protein recovery with minimal amount of incorporation. Hydrolysates prepared with Neutrase possessed a good balance in total protein recovery, degree of hydrolysis, and antioxidative activities compared to those prepared with other enzymes. Thus, Neutrase was primarily selected as a promising enzyme for future study in reaction optimization and isolation for antioxidant peptides.

Protein Content

Figure 4A:
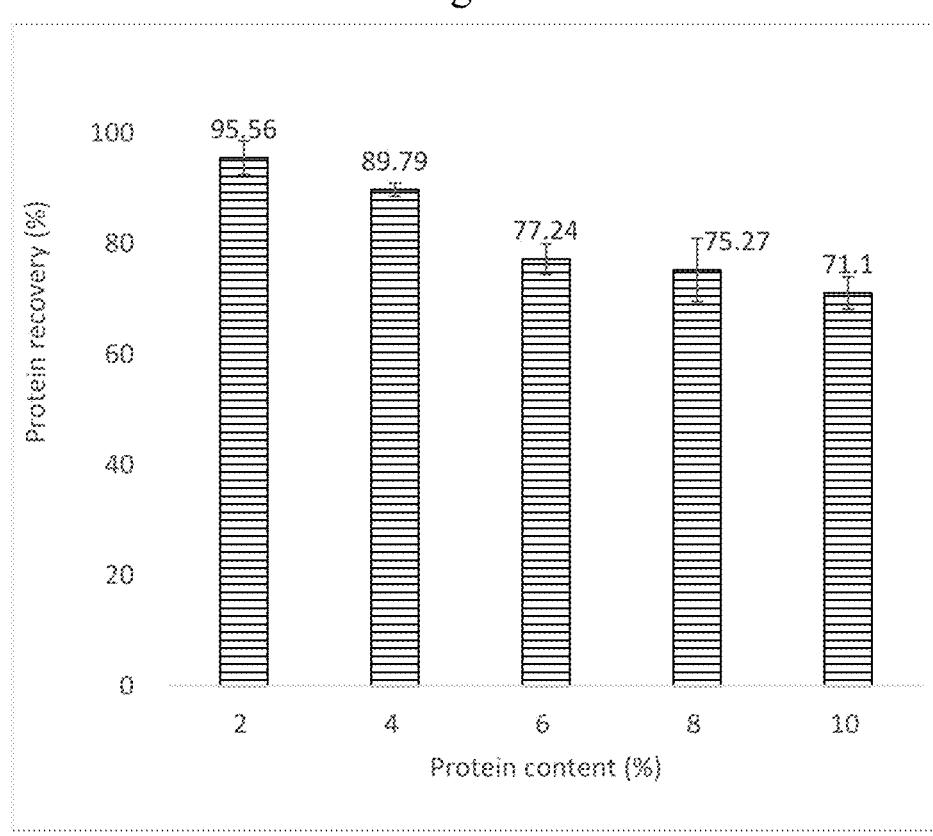
FIGS. 4A, 4B, and 4C are graphs showing effect of protein content on kafirin hydrolysate prepared with Neutrase at enzyme-to-substrate ratio of 0.4 Au/g, hydrolyzed for 21 hours, and substrate content at 2%, 4%, 6%, 8%, and 10%, with FIG. 4A showing Total protein recovery (%)
Figure 4B:
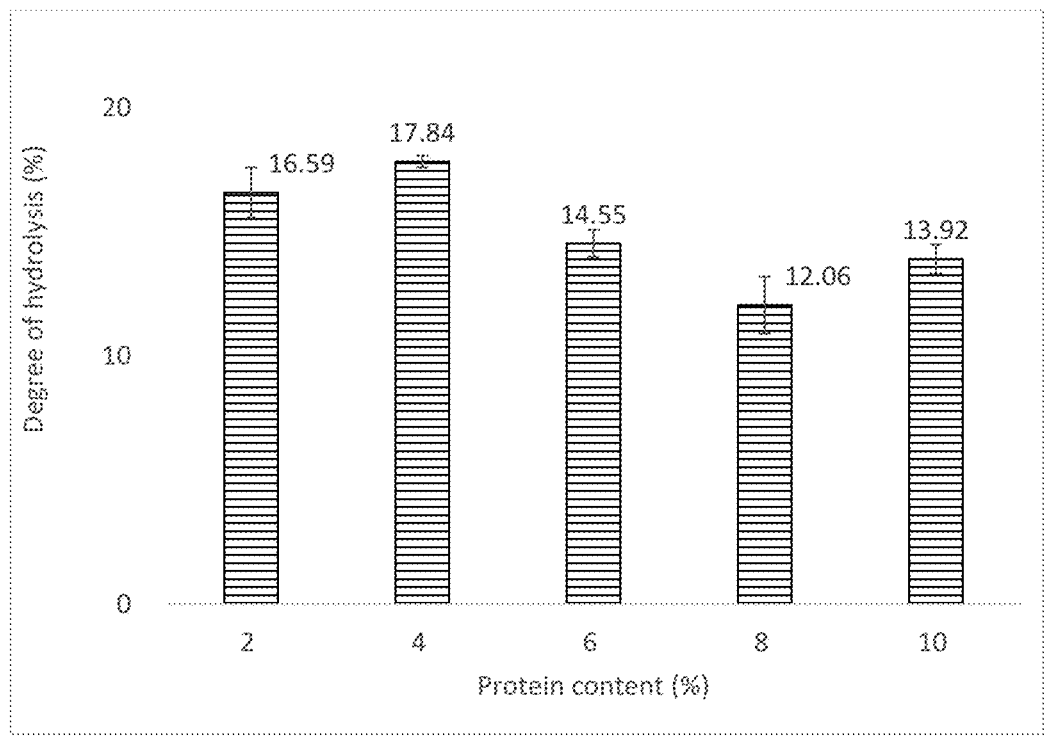
Figure 4C:
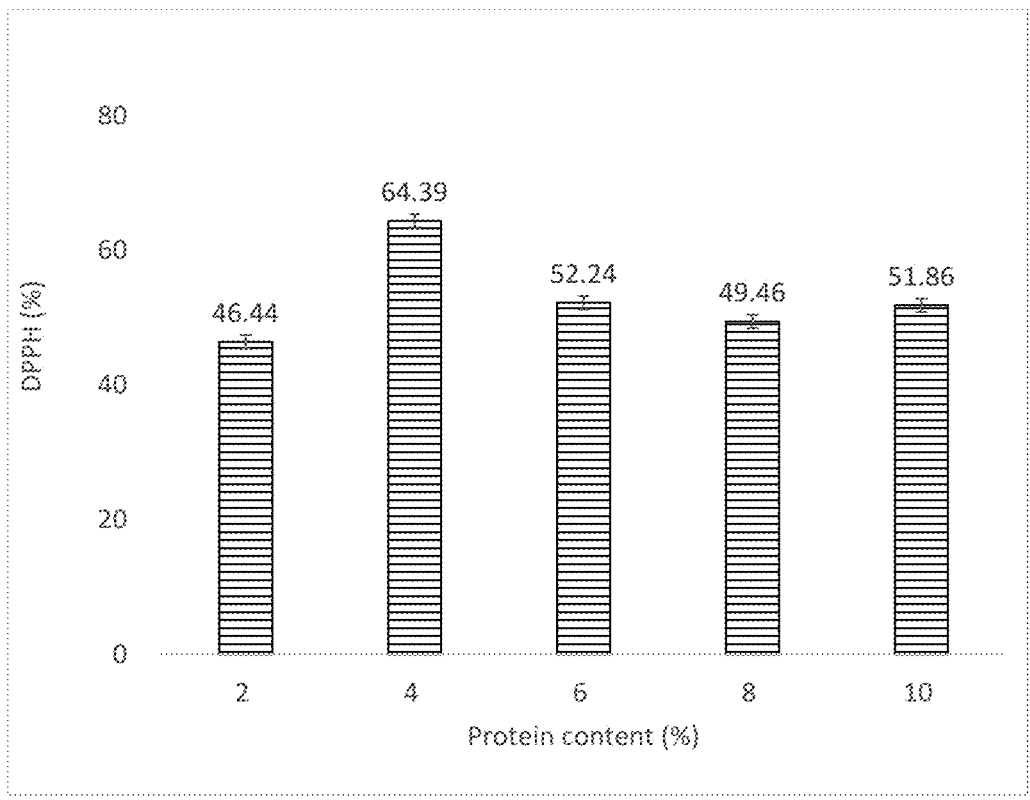

In order to study the effect of substrate content on the yield of hydrolysates and their activities, kafirin was hydrolyzed with Neutrase at different protein content from 2% to 10% while keeping the other parameters constant. The results FIGS. 4A-4C clearly specified that the total soluble protein recovered from hydrolysis persistently decreased (from 95.56% to 71.1%) as protein content increased from 2% to 10%. Degree of hydrolysis initially increased from 16.59±0.91% to 17.84±0.24% when protein content increased from 2% to 4%. However, after reaching the maximum value at 4% protein content, DH decreased afterwards. Similarly, DPPH % initially increased and then decreased after reached its maximum at 4%.

It was assumed that initially the substrate content in the hydrolysis system was too low, and the probability of collisions between the substrate and protease was limited due to lack of substrate, therefore the progress of hydrolysis was slow. Followed with an increasing amount of substrate, the overall hydrolysis was accelerated until the system reached its opportune saturation. As the reaction system was getting much more concentrated, excessive amount of substrate took up reaction space and reduced the availability of enzyme-to-substrate proteins, and the diffusion motions of the protease was also inhibited. Moreover, the enzymes activity was restricted. Thus, the reaction process was limited in the reaction system.

Considering a good balance in total soluble protein recovery and antioxidant activity, protein concentration of 4% was determined as the optimum substrate content for future experiments.

Enzyme-to-Substrate Ratio

Figure 5A:
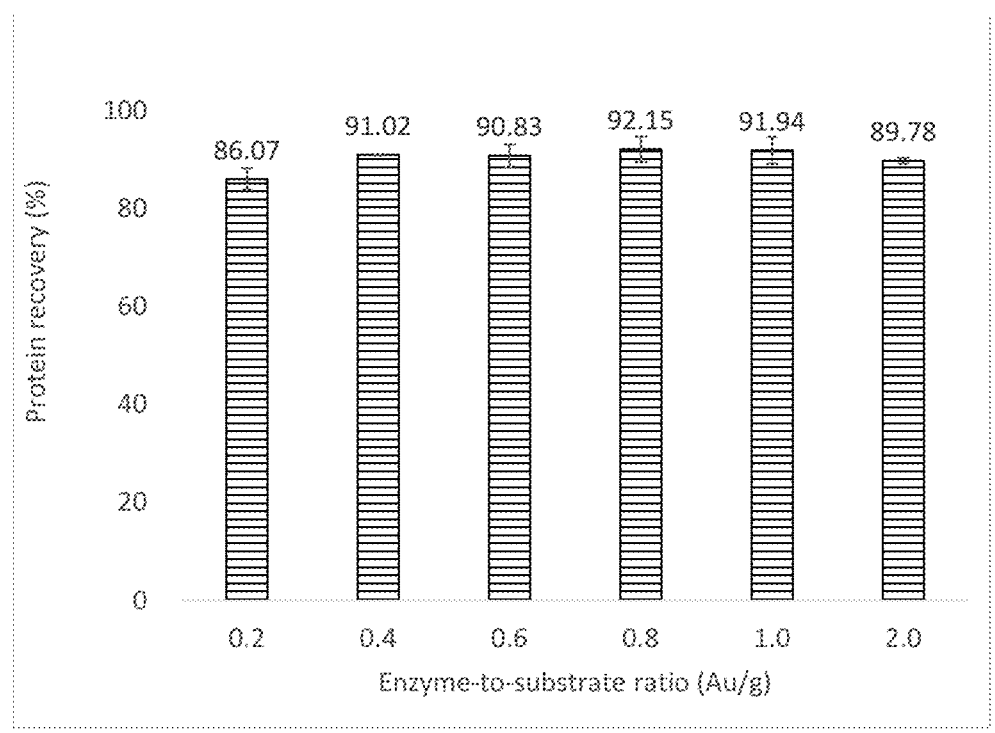
FIGS. 5A, 5B, and 5C are graphs showing effect of enzyme-to-substrate ratio on kafirin hydrolysate prepared with Neutrase at protein content of 4% hydrolyzed for 21 hours at enzyme-to-substrate ratios of 0.2, 0.4, 0.6, 0.8, and 1.0 Au/g, with FIG. 5A showing Total protein recovery (%)
Figure 5B:
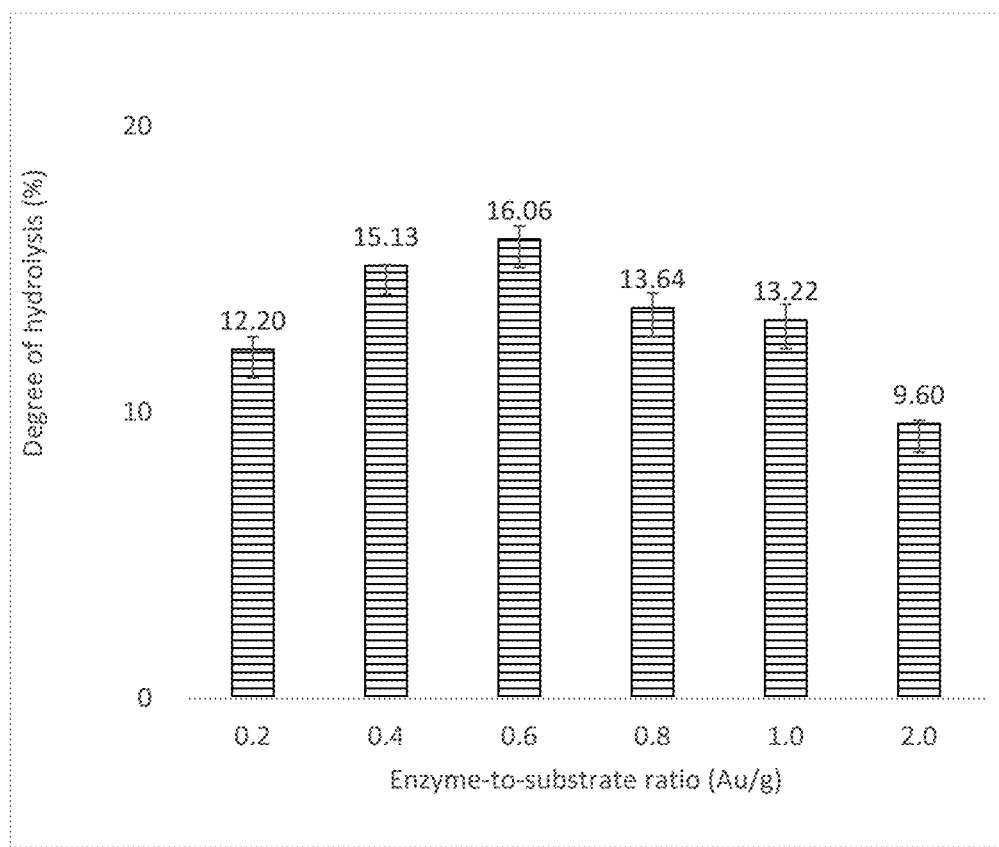
Figure 5C:
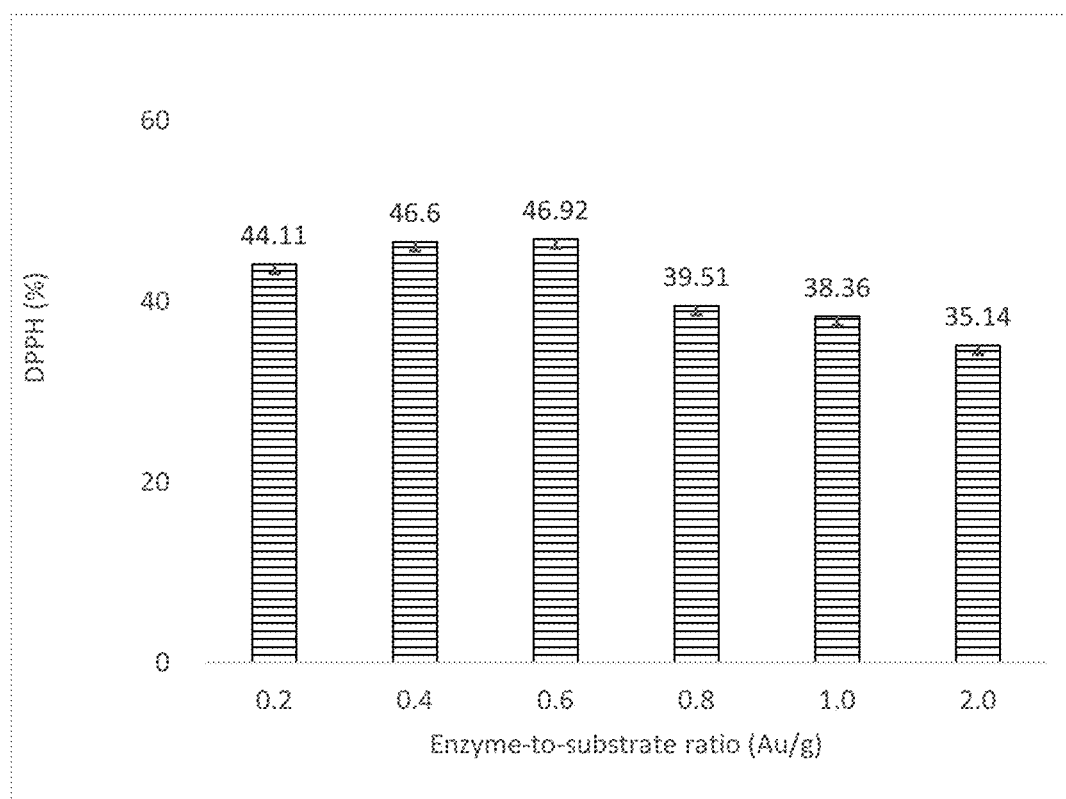

Enzymes used same units as the enzyme standard, Anson Units (Au). The effects of enzyme-to-substrate ratio Au per gram of protein (Au/g) on the peptide yield and antioxidant activity of kafirin hydrolysates prepared with Neutrase was studied. FIGS. 5A-5C show the total protein recovery, degree of hydrolysis, and DPPH % of the kafirin hydrolysates prepared with Neutrase. The ratio was gradually elevated from 0.2 Au/g to 2.0 Au/g while keeping all other reaction conditions constant. It can be seen that, both total protein recovery rate and DH increased along with the increased enzyme-to-substrate ratio from 0.2-0.6 Au/g. Later after, DH began to decrease, and protein recovery kept plateau at around 90% as the enzyme amount continued to increase. The DPPH % of the resulting hydrolysates had a similar trend with DH as it reached maximum at 0.4-0.6 Au/g and decreased afterwards. It can be concluded that at exceptional high enzyme levels, the protein available to be hydrolyzed was the limiting factor, and the additional addition of enzyme will be unnecessary for improvement of protein recovery. The experimental results showed that 0.4 Au/g was the optimum enzyme-to-substrate ratio to produce hydrolysates with fairly high antioxidant activity. Therefore, 0.4 Au/g was used for all future experiments.

Hydrolysis Time

Reaction time has a crucial impact on enzymatic hydrolysis process. It directly affected the degree of hydrolysis and the yield of water-soluble hydrolysates. Furthermore, the composition and protein structure of the hydrolysates were also influenced.

Figure 6A:
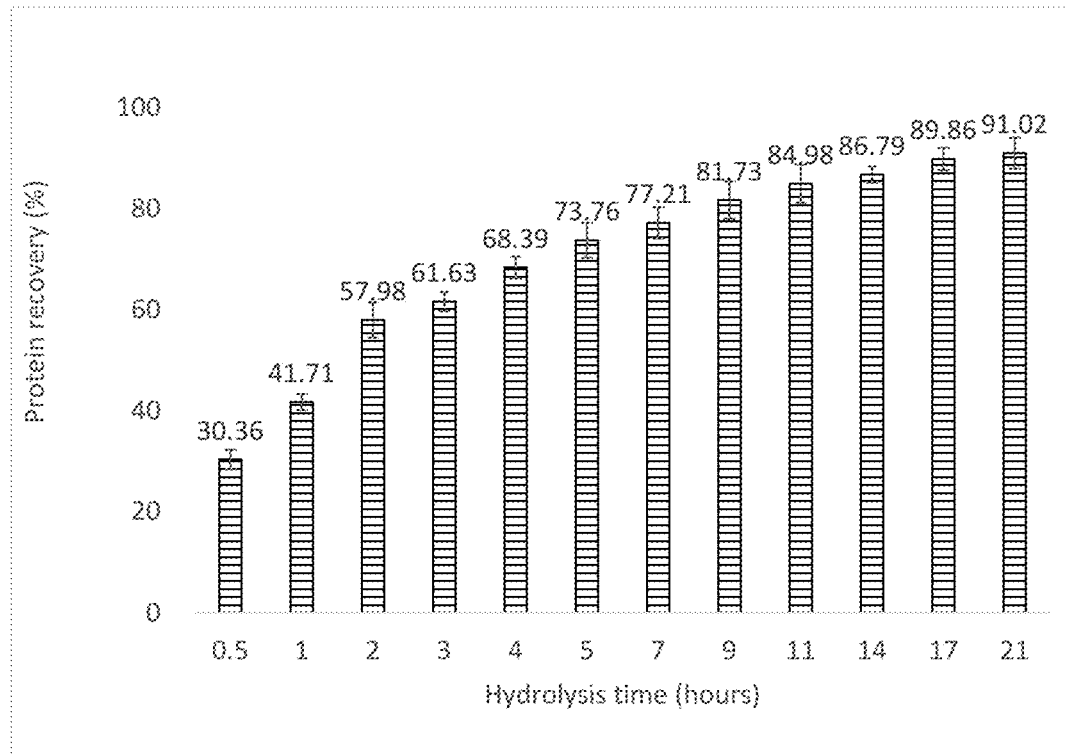
FIGS. 6A, 6B, and 6C are graphs showing effect of hydrolysis time on kafirin hydrolysate prepared with Neutrase at protein content of 4% and enzyme-to-substrate ratio of 0.4 Au/g with different time of hydrolysis (hours), with FIG. 6A showing Total protein recovery (%)
Figure 6B:
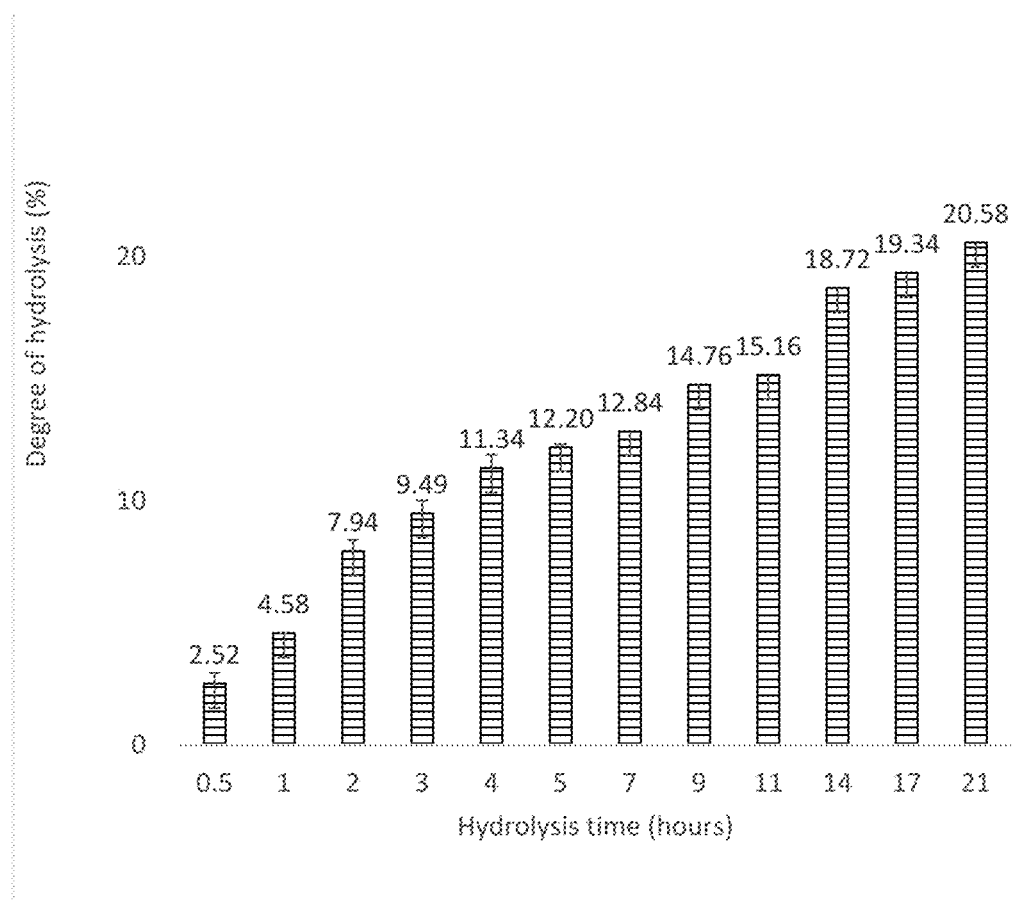
Figure 6C:
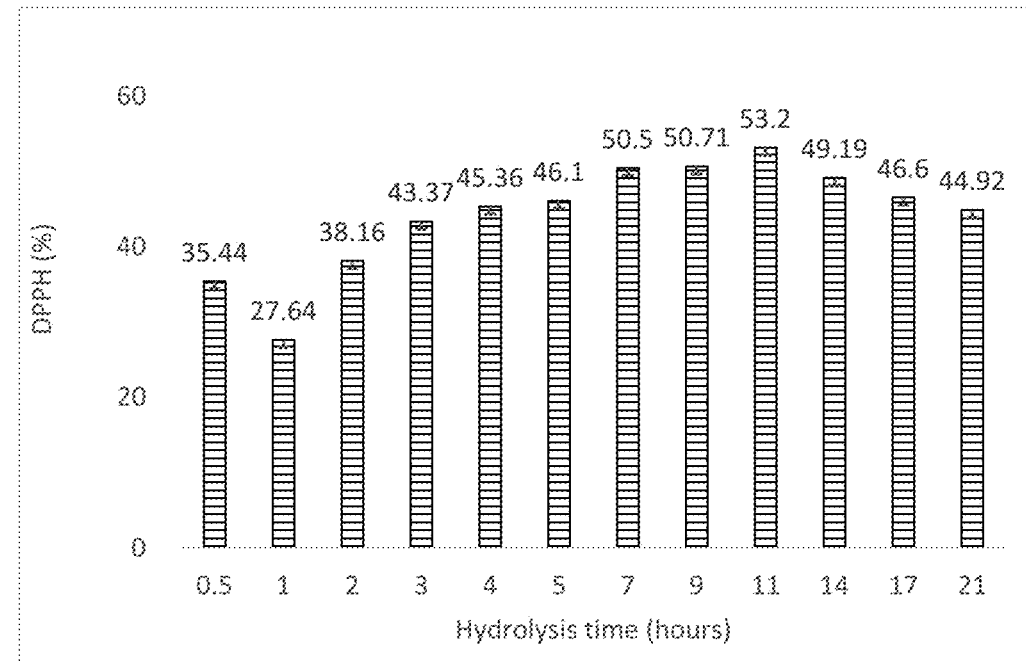

Kafirin was hydrolyzed with Neutrase at enzyme-to-substrate ratio 0.4 Au/g, substrate concentration 4% with varied hydrolysis time and the results were illustrated in FIGS. 6A-6C. Given an elongated hydrolysis time, both DH and total protein recovery continuously increased, which indicated that peptide bonds had been cleaved during the hydrolysis, and protein started to break down into fragments, producing more short chain peptides that are inclined to be water-soluble. After the reaction reached the steady state phase, no apparent increase in total protein recovery was observed. It was assumed that, at initial stage when both substrate concentration and the enzyme activity were high, the protein was hydrolyzed at a higher rate. As the hydrolysis progressed, the rate of hydrolysis decreased subsequently due to the reduced enzyme activity and the decreased substrate concentration.

A previous study claimed that higher DH of hydrolysates usually associated with stronger antioxidative activities. However, a prolonged hydrolysis time or a higher DH did not necessarily produce a higher antioxidant activity in this study. As shown in FIG. 6C, DPPH % of the hydrolysates gradually increased until it reached its maximum values and then decreased as hydrolysis time extended. Thus, the hydrolysis time is a key factor in producing antioxidative peptides as specific structure and critical peptide size may be necessary to manifest a certain antioxidant activity. The longer time the substrate exposed to enzymes, the more excessive hydrolysis could possibly have occurred. Unnecessary excessive hydrolysis produced short peptides and amino acids that had lost the essential structure accounting for the antioxidative activities thus exhibited a decreased DPPH %. Besides, the transformation of peptide structure could be another reason causing DPPH % decreased.

Considering both total protein recovery as well as hydrolysate antioxidant activity, 17 hours of hydrolysis time was determined as an optimal reaction time for later experiments.

Ultrafiltration of Kafirin Neutrase Hydrolysates

Molecular weight distribution is one of the most important properties in determination of the functionality and bioactivity of hydrolysates. Kafirin hydrolysate prepared with Neutrase at optimal conditions (protein content of 4%, enzyme-to-substrate ratio of 0.4 Au/g and hydrolyzed for 17 hours) were sequentially subjected to Amicon Ultra-15

Figure 7:
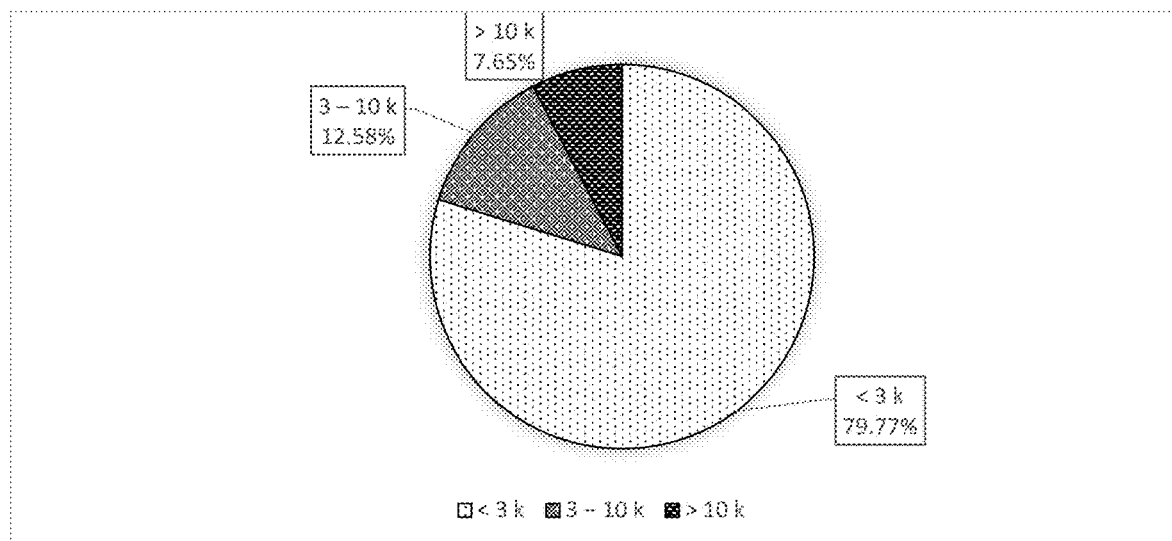
FIG. 7 is a pie chart showing distribution of ultrafiltrated fractions of kafirin Neutrase hydrolysate prepared at protein content of 4% enzyme-to-substrate ratio of 0.4 Au/g and hydrolyzed for 17 hours followed with membrane filtration using 10 kDa and 3 kDa membranes.

Centrifugal Filter Devices with 10 kDa and 3 kDa molecular weight cut-off membranes to categorize the distribution of hydrolysates based on molecular weight, and to study the relationship between peptide size and their antioxidant activities. As a result, permeate and retentate fractions with different molecular weight range were obtained as followed: the small-sized peptide fraction with $M_w$ lower than 3 kDa fraction (denoted as <3 k), the medium-sized peptide fraction with $M_w$ between 3 kDa and 10 kDa (denoted as 3-10 k), and large-sized peptide fraction with $M_w$ exceeding 10 kDa fraction (denoted as >10 k). The proportional distribution of these three fractions were shown in FIG. 7. As it can be seen, smaller-sized peptide fraction (<3 k) was the largest portion which took up about 79.77% followed with medium-sized peptide fraction (3-10 k) accounted for 12.58% and large-sized peptide fraction (>10 k) accounted for 7.65%. It was speculated that, prolonged hydrolysis time provided adequate digestion of protein into short-chained peptides, which can also be perceived by a relatively higher degree of hydrolysis and total protein recovery. The released peptides might be divided into even shorter oligopeptides or free amino acids as hydrolysis proceeded. Thus, majority of hydrolysates fell into smaller-sized fraction. Since the proportional distribution of ultrafiltrated hydrolysates was not commonly reported, there were limited literatures for comparison.

The three fractions from ultrafiltration along with the original hydrolysates without going through ultrafiltration (denoted as Mix) were analyzed for their total phenolic content and antioxidant activities as shown in FIG. 8A-8E.

Figure 8A:
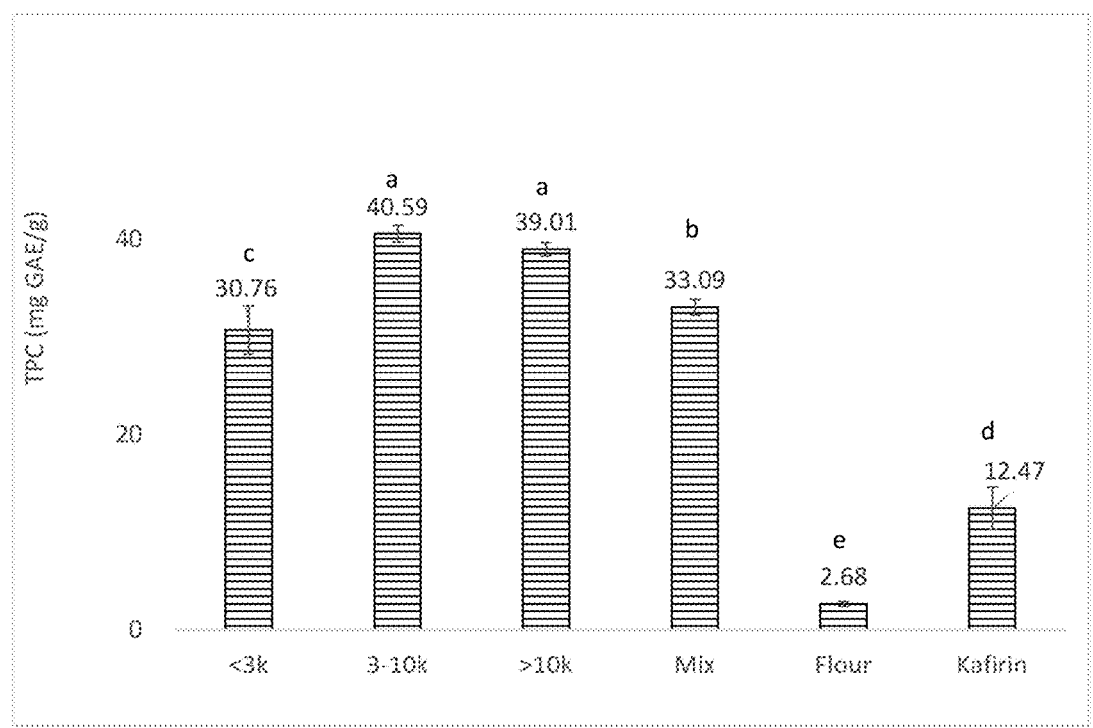
FIGS. 8A, 8B, 8C, 8D, and 8E are graphs showing total phenolic content and antioxidant activities of kafirin Neutrase hydrolysate ultrafiltrated fractions prepared at protein content of 4% enzyme-to-substrate ratio of 0.4 Au/g and hydrolyzed for 17 hours followed with membrane filtration using 10 kDa and 3 kDa membranes, with FIG. 8A showing Total phenolic content (mg GAE/g)

The total phenolic content (TPC) was measured for sorghum flour, extracted kafirin, and kafirin hydrolysates along with its ultrafiltration fractions by using the Folin-Ciocalteu method. The results were expressed as gallic acid equivalent per gram of sample (GAE/g) as shown in FIG. 8A. Among the four fractions of hydrolysates, 3-10 kDa fraction possessed highest TPC value (40.59±0.86 mg GAE/g), followed with >10 kDa fraction of 39.01±0.68 mg GAE/g, and <3 kDa the lowest value (30.76±2.47 mg GAE/g). The TPC values of 3-10 kDa and >10 kDa fractions are both significantly higher than Mix (P<0.05), which indicated that process ultrafiltration concentrated the TPC in these fractions. However, the difference between 3-10 kDa and >10 kDa is not significant. The TPC values of kafirin hydrolysates are all significantly higher than that of sorghum flour (2.68±0.24 GAE/g) and sorghum protein kafirin (12.47±2.15 mg GAE/g). This result revealed that sorghum protein kafirin contains concentrated phenolic content within sorghum flour, and the hydrolysis process dramatically increased the total phenolic content of sorghum kafirin by releasing the peptides with phenolic amino acid residues and other free phenolic compounds. Phenolic compounds could be released during enzymatic hydrolysis, which contributed to a higher TPC. It is important to note that, TPC may be overestimated due to the interference of other products that could react with Folin-Ciocalteu reagent such as nucleic acids.

Figure 8B:
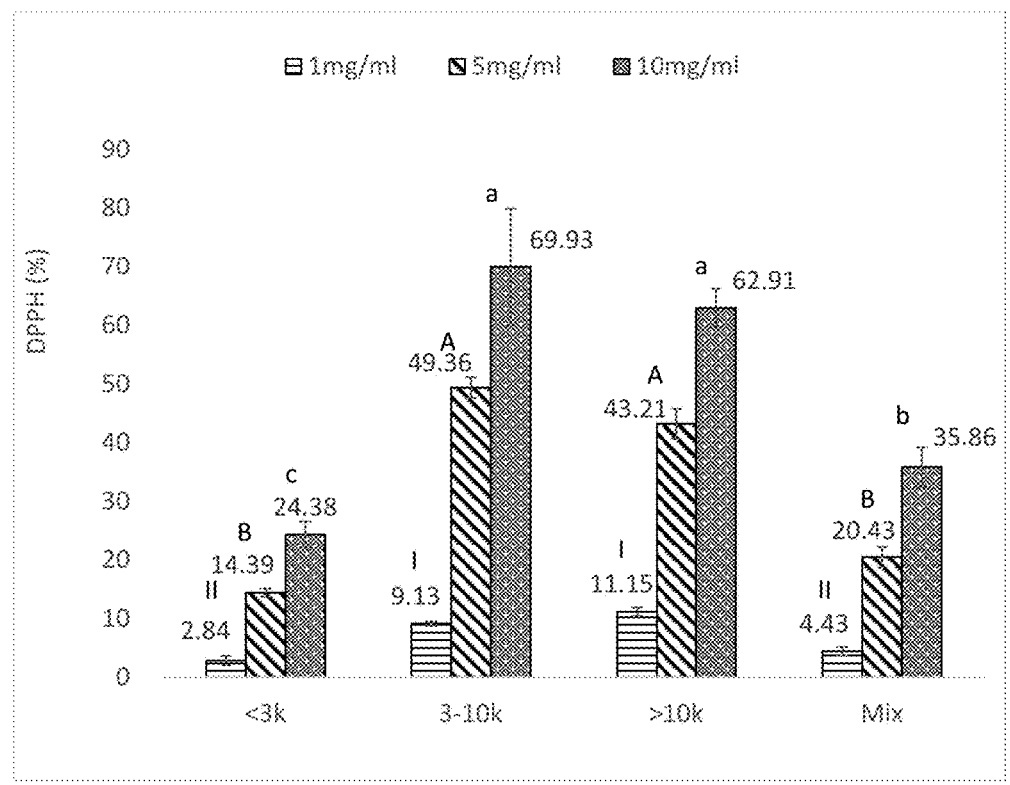

Free radical scavenging activity of proteins or peptides is closely related to the molecular weight. DPPH % was measured for the kafirin ultrafiltrated hydrolysates to compare their difference in electron donating activities as shown in FIG. 8B. It was found that, 3-10 kDa and >10 kDa fractions exhibited higher DPPH % than other hydrolysate fractions at varied substrate concentrations (1-10 mg/mL). Meanwhile, <3 kDa fraction exhibited the lowest activity. This result indicated that the medium-sized hydrolysate fraction, specifically, 3-10 kDa fraction possessed stronger potential to act as electron donors in quenching free radicals.

Figure 8C:
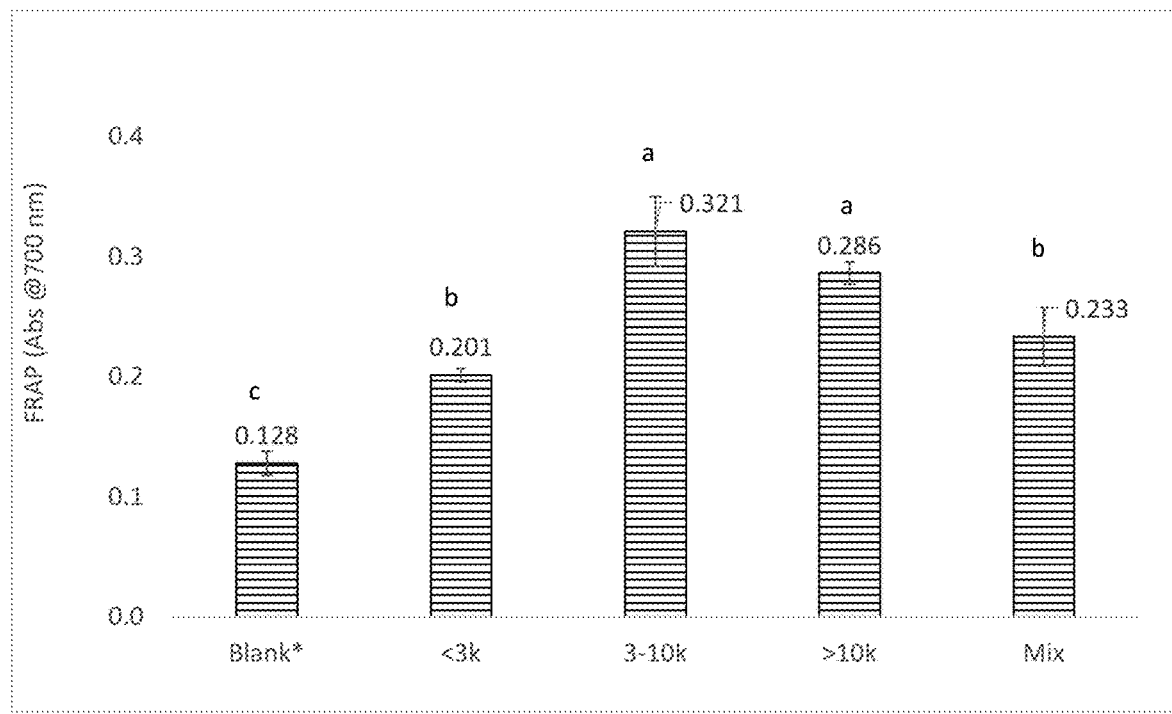

The ferric iron reducing power assay (FRAP) measured the ability of an antioxidant to reduce Fe' to Fe', which was often used as an indicator of electron-donating or hydrogen-donating abilities. The formation of Fe' complex was monitored using Perl's Prussian blue at 700 nm wavelength absorbance. Thus, an increased absorbance at 700 nm indicated a higher reducing power. Many reports had revealed a positive correlation between antioxidant activities and reducing power. As shown in FIG. 8C, the 3-10 kDa fraction exhibited the strongest reducing power ability with the highest absorbance value (0.321±0.029) followed with >10 kDa fraction (0.286±0.010), and the <3 kDa fraction had the lowest absorbance (0.201±0.006) among the four peptide samples. All the four ultrafiltrated hydrolysate fractions exhibited significantly (P<0.05) higher absorbance over the blank control (0.128±0.010). This result could serve as the evidence that the antioxidative peptides act as electron-donors and result in reduction of Fe' to Fe'. The medium-sized peptide fraction (3-10 kDa) was the most active fraction in regards of the electron-donating ability.

Figure 8D:
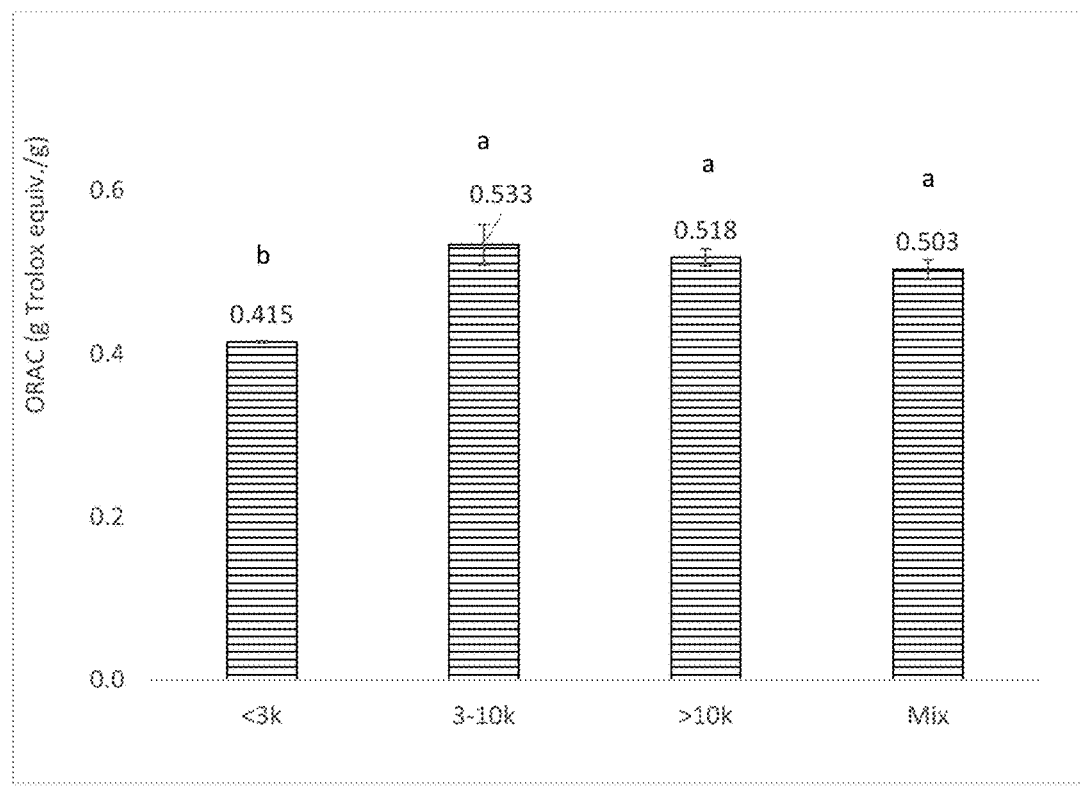

ORAC assay follows a hydrogen atom transfer mechanism where the H of the peptides neutralizes the radicals and breaks the chain reactions of thermally generated peroxyl radical from AAPH. Therefore, ORAC evaluated the hydrogen donating capacity of the antioxidant. The small-sized fraction of peptides had a significant lower (P<0.05) ORAC values than the other ultrafiltrated fractions of kafirin Neutrase hydrolysates (FIG. 8D). Besides, all hydrolysate fraction had a relatively high ORAC value (>0.4 g Trolox equiv./g) compared with other previously reported values. This data revealed the fact that the antioxidant peptides are excellent proton donors to quench radicals as counterpart of their antioxidant profile.

Figure 8E:
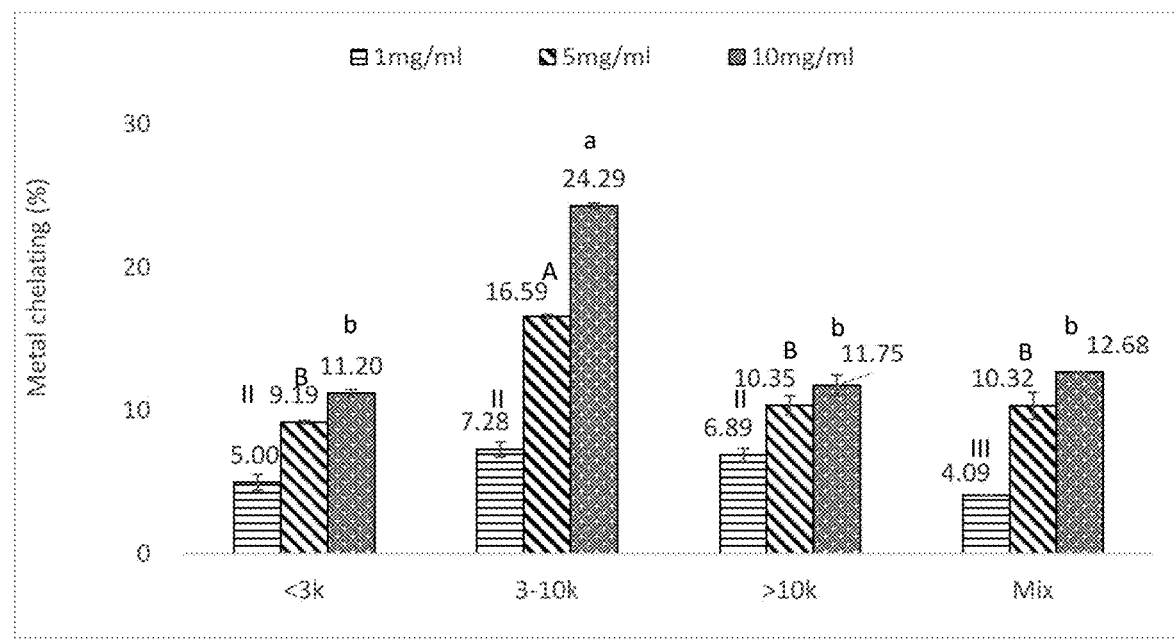

Transition metal ions such as Fe' and Cu' are key catalyst in generation of oxygen species that lead to oxidation of unsaturated fat and could cause physiological damages to biomolecules and subsequent aging, cancer and diseases. Especially, Fe' generates highly reactive and destructive hydroxyl radicals by Fenton reaction and accelerate the lipid peroxidation chain reaction. Thus, it is necessary to measure the chelating ability of the compound for evaluating its antioxidative activities. FIG. 8E shows the metal chelating ability of kafirin Neutrase hydrolysate fractions at different concentrations. All the hydrolysates fractions exhibited metal chelating abilities, and the ability was enhanced as the antioxidant dosage increased. 3-10 kDa fraction presented exceptional higher chelating capacity (24.29±0.18% at 5 mg/mL) (P<0.05) than the other three fractions (11.20-12.68% at 5 mg/mL). This result indicated that kafirin hydrolysates prepared with Neutrase had iron binding capacity which contributed to its activity as an antioxidant. The chelation capacity may be attributed to the exposure of more acidic and basic amino acids during the process of hydrolysis as the carboxyl and amino groups in their side chains can bind Fe', and this ability may also contribute to their hydroxyl radical scavenging effects of antioxidants due to the combined effects.

Some studies indicated that short-chained peptides fraction with smaller $M_w$ are more efficient antioxidants, as they are more accessible to the oxidant agents. However, other studies indicated that medium- or large-sized peptides were more active. In this study, the medium-sized peptide fraction was found to be more effective. It was speculated that, the hydrolysates permeated through 3 kDa membrane yielded much small-sized peptides and free amino acids that eventually decreased the overall activity of <3 kDa fraction. It was also explained previously that excessive hydrolysis results in breakage of essential structures including peptide sizes and specific amino acid sequences that were responsible for the radical scavenging activities.

In addition, it was found that TPC was positively correlated to antioxidant activity measured by DPPH % ($R^2$=0.8807) and reducing power ($R^2$=0.9804). Both TPC ($R^2$=0.972) and peptide content ($R^2$=0.937) had a strong positive correlation with and antioxidant activity of wheat germ hydrolysates measured by DPPH %. Some studies reported that the ABTS radical scavenging activity of rice bran protein hydrolysate was coincidental with TPC with positive correlation (coefficient R=0.7). However, others reported that there were no correlations between TPC and DPPH %. Phenolic compound was not the only factor in determining the overall antioxidant activity of the hydrolysates, instead, peptides and phenolic compounds released during hydrolysis both contributed to the antioxidant activity. Throughout the hydrolysis, the mode of polyphenol-peptide interaction was changed and free phenolics were released from bound-phenolics. The phenolic content contributed to the radical scavenging activity via hydrogen atom donation activity of hydroxyl group in phenolic compounds. Meantime, amino acids with a phenolic hydroxyl group in peptide sequence may also be responsible for radical scavenging activity. It was proposed that the antioxidant capacity was also dependent on the interaction of peptide and phenolic content at different stages of hydrolysis. At early stage of hydrolysis, the increase of peptide content might be dominant in the increase of antioxidant activity; however, as hydrolysis proceeded, the peptides were digested into free amino acids resulting in a decreased activity. The phenolic content released for the late stage were more responsible for the activity. Therefore, the medium-sized (3-10 kDa) hydrolysates fraction with a concentrated phenolic content demonstrated higher antioxidant activities as revealed by DPPH %, reducing power, and metal chelating %.

In general, ultrafiltration is an effective approach to fractionate and isolate peptide fraction from hydrolysate mixture based on molecular weight distribution. The isolated peptide fraction with medium molecular range (3-10 kDa) exhibited stronger antioxidative activities. The antioxidative capacity of hydrolysates could be possibly utilized to reduce the oxidized intermediates in lipid peroxidation process, and therefore, act as primary and secondary antioxidants.

Inhibition of Lipid Oxidation in Model Systems
Oil-in-Water Emulsion System

The ability of antioxidants to inhibit lipid oxidation in food emulsions depends on a lot of factors such as reactivity and concentration of antioxidants; environmental conditions including pH, ionic strengths, and temperature; and partitioning between oil, water and interfacial phases. An oil-in-water emulsion model system was utilized to mimic the chemical, physical and environmental conditions in real food products. 3-10 kDa fraction kafirin Neutrase hydrolysate at 50 mg and 100 mg per mL of soy oil was incorporated to prepare emulsion samples. Emulsion prepared with hydrolysates as the sole emulsifier did not reach steady state even at high concentrations, which indicated that protein hydrolysate was not an ideal emulsifier on its own. Thus, Tween-20 was incorporated as an additional stabilizer to enhance the emulsion stability. The physical properties of the emulsion samples were characterized by measuring their turbidity and stability. The degrees of lipid autoxidation and peroxidation were determined by quantifying the concentrations of lipid peroxide (POV) and thiobarbituric acid reactive substances (TBARS) as primary and secondary lipid oxidation products, respectively. The results of emulsion samples incorporated with hydrolysates were compared to that of blank control during the incubation period at 37° C. until 14 days.

Figure 9A:
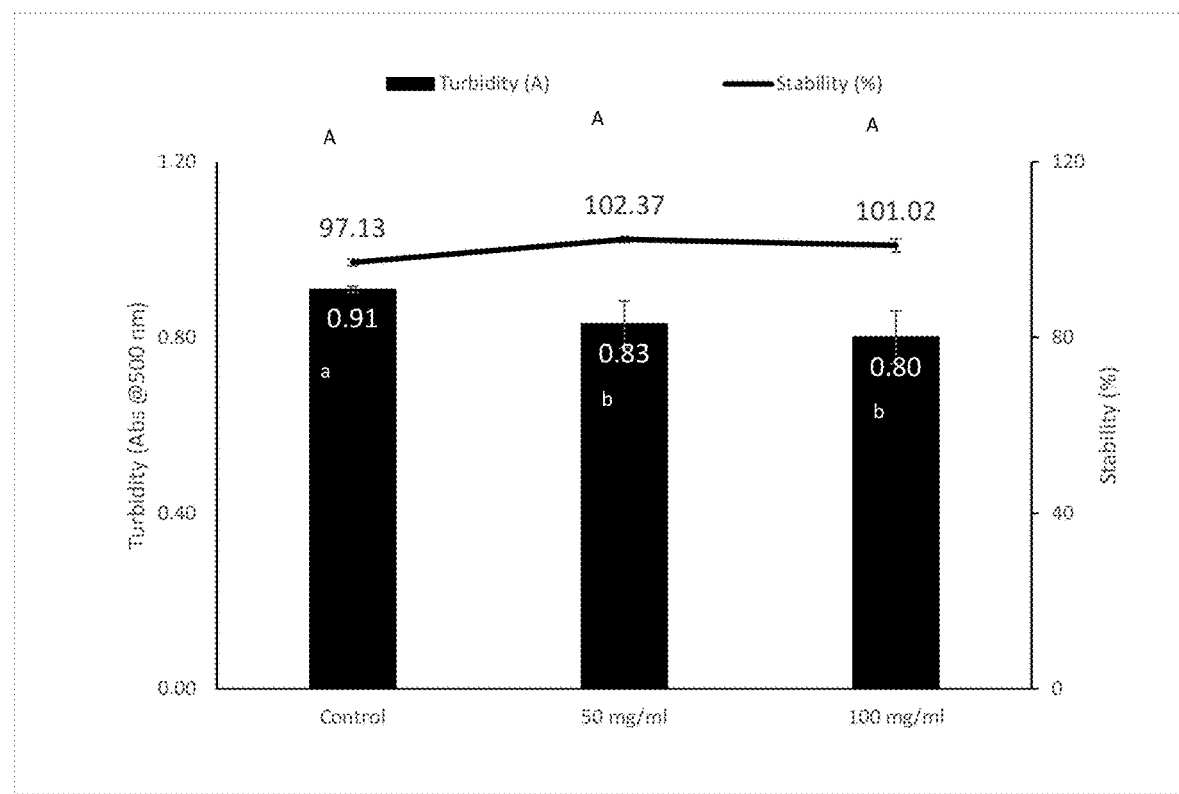
FIGS. 9A, 9B, and 9C are graphs showing inhibition effect of kafirin Neutrase 3-10 kDa hydrolysate prepared at enzyme-to-substrate ratio of 0.4 Au/g and hydrolyzed for 17 hours in an oil-in-water emulsion model system added with 50 and 100 mg/mL oil, with FIG. 9A showing Emulsion turbidity (Abs at 500 nm) and stability (%)
Figure 9B:
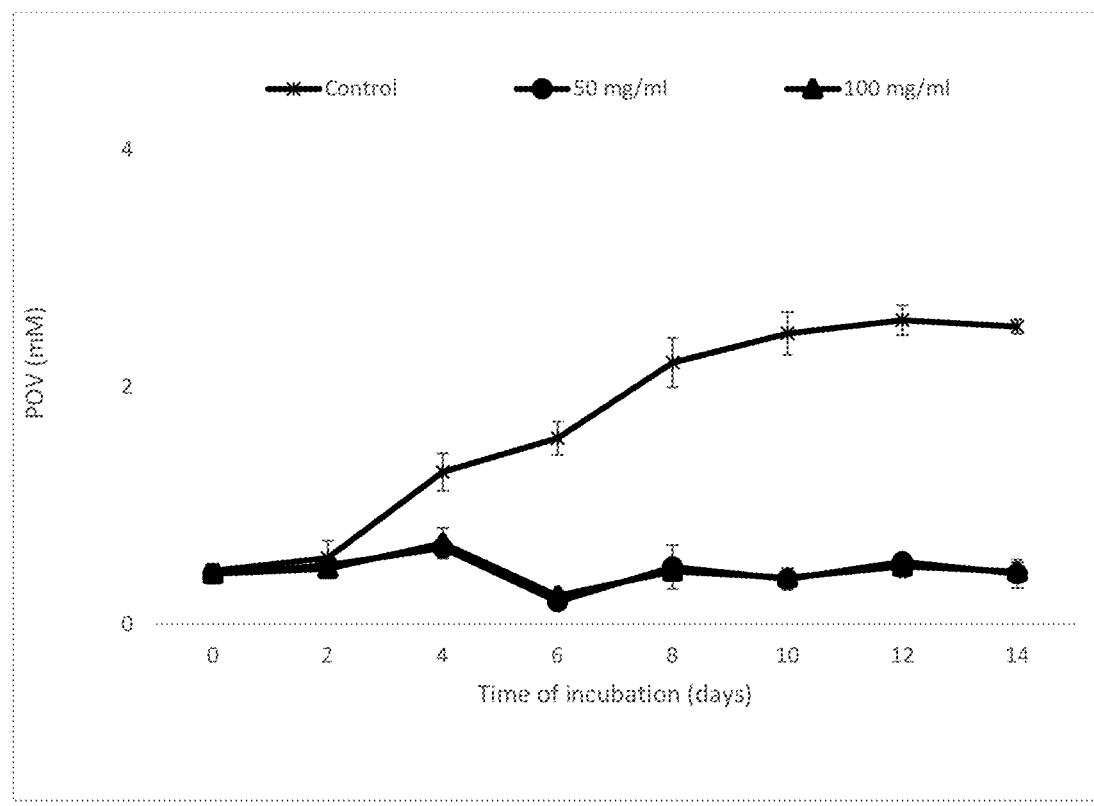
Figure 9C:
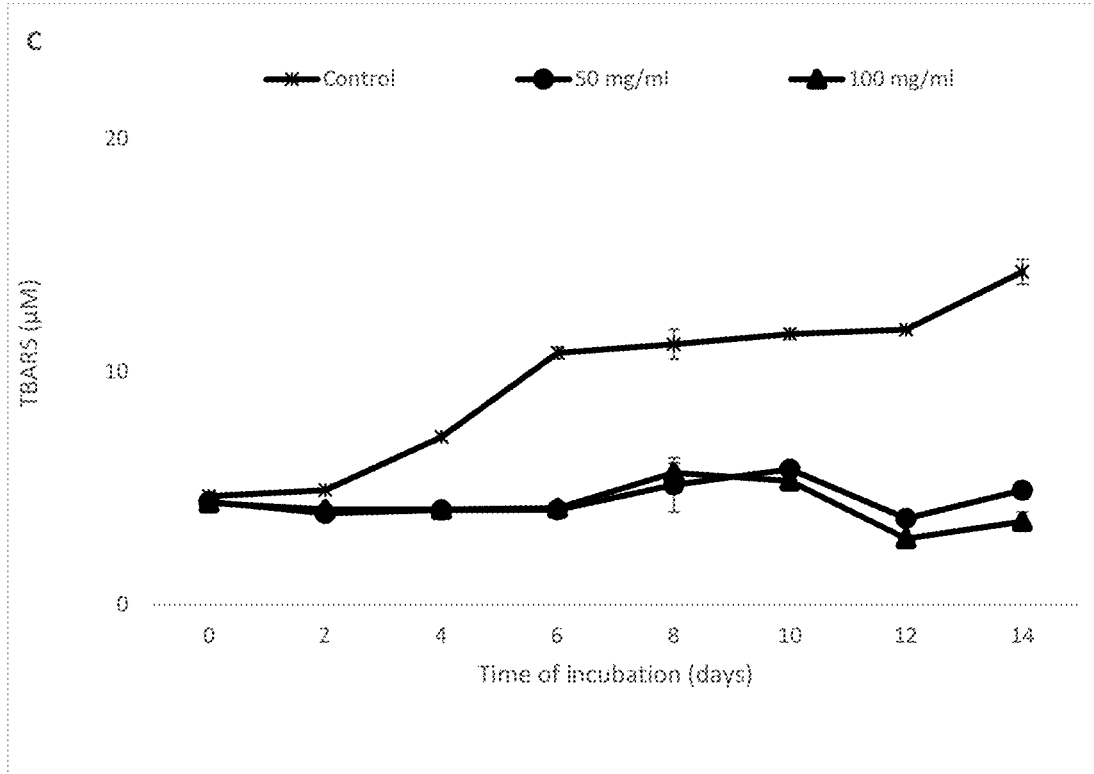

As shown in FIG. 9A, with hydrolysate incorporated at 50 mg/mL ($A_{500}$=0.83±0.03) and 100 mg/mL ($A_{500}$=0.80±0.03), both emulsion sample had a lower turbidity than that of blank control ($A_{500}$=0.91±0.02). However, the high turbidity values ($A_{500}$>0.80) observed in all emulsion samples indicated that the soy oil was effectively dispersed. Meantime, the addition of hydrolysates slightly increased emulsion stability as determined by changes in emulsion turbidity. This was probably due to the adsorption action of hydrolysates resulted in a better dispersion of oil droplets. From this point, the addition of hydrolysate enhanced the overall emulsion stability. On the other hand, the emulsion samples with hydrolysate incorporated had a less tendency to stay stable during the extended storage time till 14 days, and with more hydrolysate added, the less stable it became. It was interpreted that a competitive adsorption at the interface which favored hydrolysates at high concentrations.

Most importantly, the presence of kafirin hydrolysates decreased both POV and TBARS in the entire incubation period as compared to the control. After 14 days of incubation at 37° C., the emulsion sample with addition of 50 mg hydrolysate per mL of soy oil exhibited an average inhibition the formation of POV and TBARS by 77.14±13.81% and 54.34±9.78%, respectively. The emulsion sample with increased concentration of hydrolysate at 100 mg/mL displayed a slight but not substantial enhancement of POV and TBARS inhibition, which were 76.41±13.81% and 59.91±13.51%, respectively.

The inhibition efficacy of kafirin hydrolysate in this study was higher than that of potato protein prepared at same concentration reported by a previous study. This result provided important evidence clarifying the antioxidative effects of kafirin hydrolysate in stabilizing the oil-in-water emulsions by reducing the formation of lipid hydroperoxide and TBARS. This activity might be associated with the free radical scavenging activities and pro-oxidative metal chelating abilities of the kafirin hydrolysates. Besides, in food emulsion systems due to the amphiphilicity of proteins and peptides, the hydrolysates can diffuse to the water-oil interface and act as surfactants to adsorb or loosely bind to oil droplets and form a physical barrier to hinder the access of oxidizing agents thus contribute to reduced lipid peroxidation. The protein emulsifiers can also prevent oil droplets from coalescing whilst protecting the interior of oil droplets from oxidation.

Ground Meat System

The ground meat is easily susceptible to oxidative process due to the grinding process disrupts the muscle membrane systems and therefore exposes unsaturated fatty acids and proteins to oxidative agents such as molecular oxygen, oxidative enzymes, heme compounds, and metal prooxidants. The oxidation of lipid does not directly result in rancidity until fatty acids are decomposed to low $M_w$ volatile compounds know as secondary lipid oxidation products. These products adversely affect the sensory quality of foods perceived as off-flavors and aroma. In order to evaluate the inhibiting effects of peptide antioxidants against lipid and/or fat peroxidation, 3-10 kDa fraction of kafirin hydrolysate prepared with Neutrase at optimized conditions was incorporated with ground pork at 0.5 mg and 1.0 mg hydrolysate per gram of meat. The oxidative stability of meat samples was determined by quantifying their secondary oxidative products by measuring TBARS at different days during incubation at 4° C. and compared to a blank control and a positive control prepared with rosemary extract at 0.5 mg/g.

Figure 10:
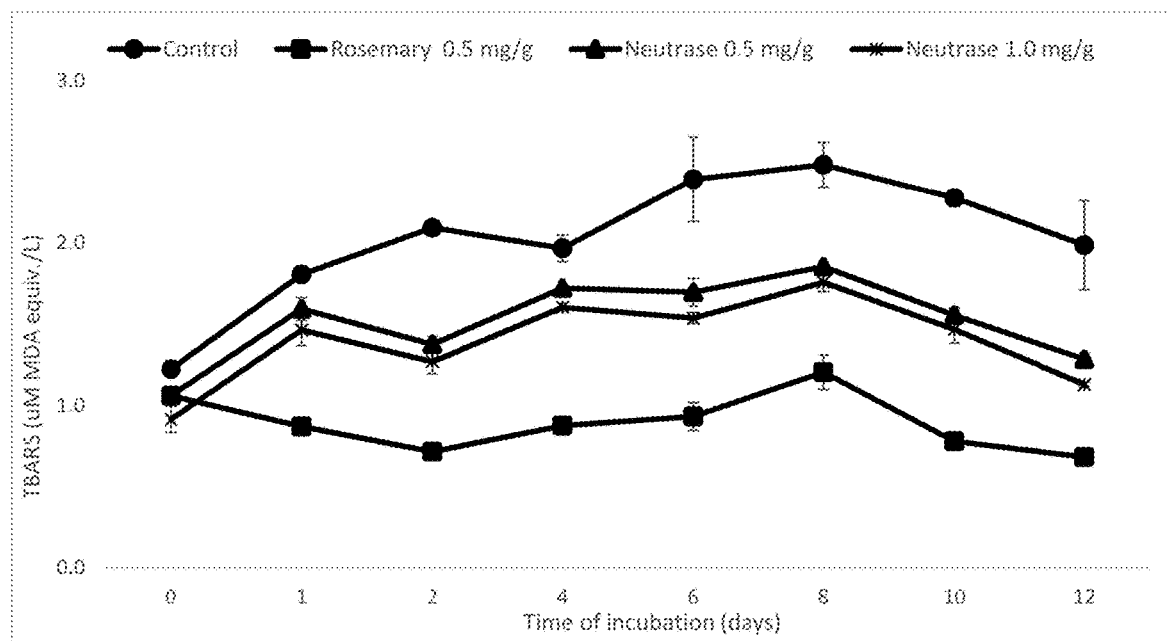
FIG. 10 is a graph showing inhibition effect shown as TBARS of kafirin Neutrase 3-10 kDa hydrolysate prepared at enzyme-to-substrate ratio of 0.4 Au/g and hydrolyzed for 17 hours in a ground meat system added with 0.5 and 1 Mg/g meat.

The results in FIG. 10 clearly indicated the trend that meat peroxidation gradually proceeded along with days of incubation as reflected by the continuous increase of TBARS values. On day 0 right after the meat samples were prepared, all the meat samples showed close values of TBARS. From day 1, TBARS of meat samples with addition of hydrolysates started to become lower than that of control, and the trend of inhibition is obvious with prolonged incubation time. At the end of incubation, TBARS of meat sample was inhibited by 35.34% and 43.17% with hydrolysates incorporated at 0.5 mg/g and 1.0 mg/g, respectively. The average inhibition rate was 24.16±10.14% and 30.71±9.26% during the 12-day storage period. This result indicated that the addition of hydrolysates lowered amount of lipid peroxide generated, which provides important evidence showing the inhibition effect of kafirin hydrolysates against lipid peroxidation of ground pork. Rosemary extract is a well-known natural antioxidant found to exhibit inhibition on lipid oxidation at low concentrations of 100-2500 ppm. The inhibition effects of peptide antioxidants are not as strong as rosemary extract, which could be due to the impurity of hydrolysates. Thus, further fractionation to isolate critical peptide sequences responsible for the activities is needed.

Figure 11:
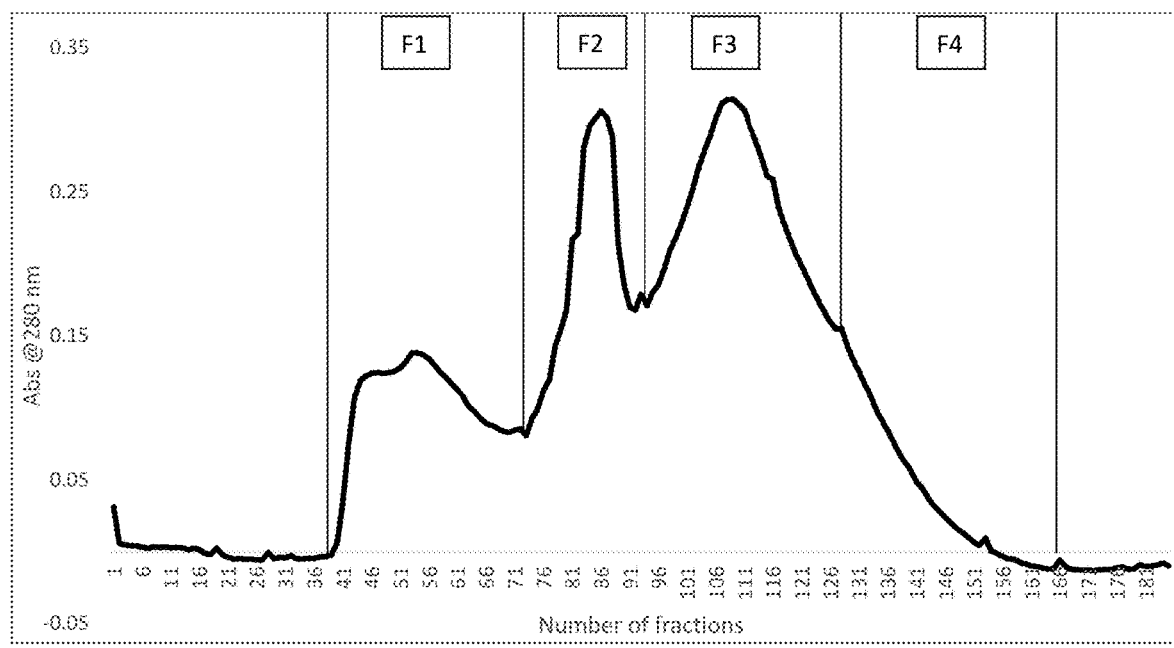
FIG. 11 is a graph showing gel filtration chromatogram of kafirin Neutrase 3-10 kDa hydrolysate prepared at enzyme-to-substrate ratio of 0.4 Au/g and hydrolyzed for 17 hours in a Sephadex G-25 column (26 mm×850 mm)
Figure 12A:
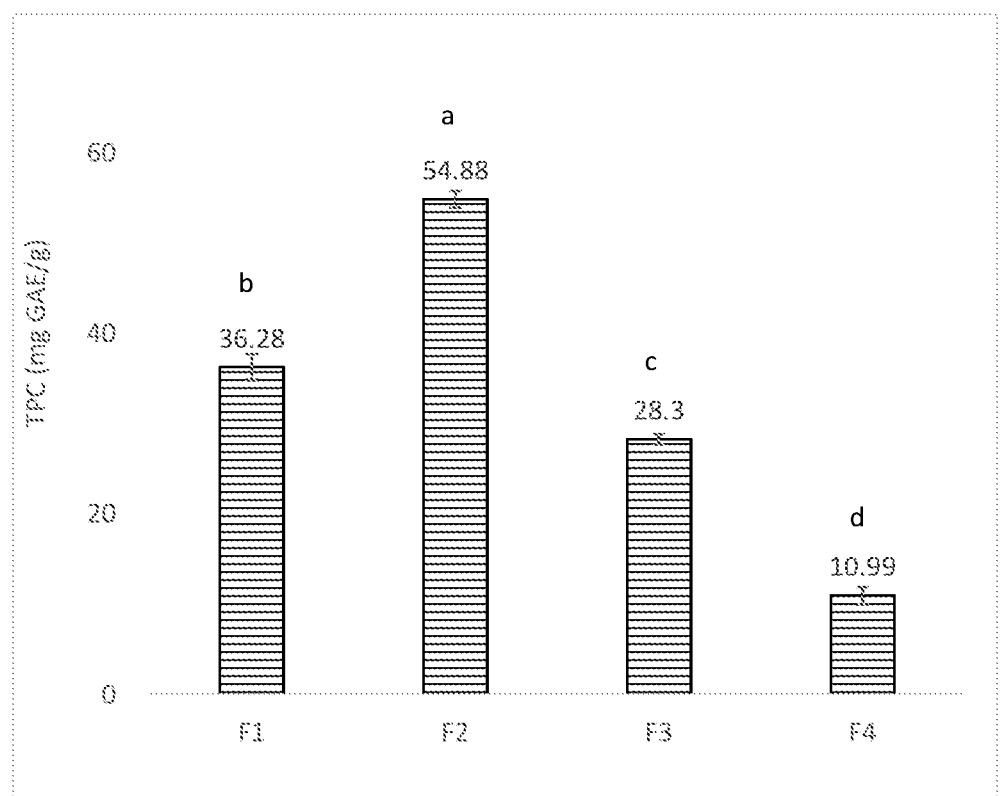
FIGS. 12A and 12B are graphs showing total phenolic content and antioxidant activities of gel filtration fractions F1-F4 of kafirin Neutrase 3-10 kDa hydrolysate prepared at 0.4 Au/g, 4%, and hydrolyzed for 17 hours, with FIG. 12A showing Total phenolic content (mg GAE/g)
Figure 12B:
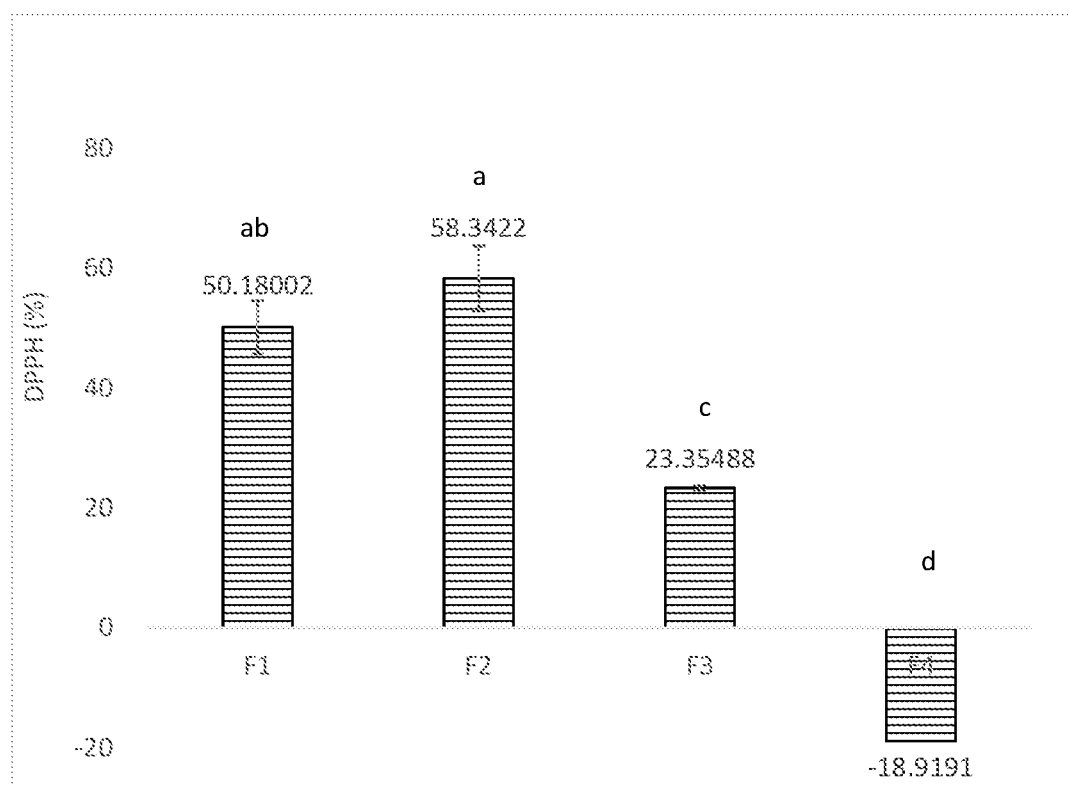
Figure 13A:
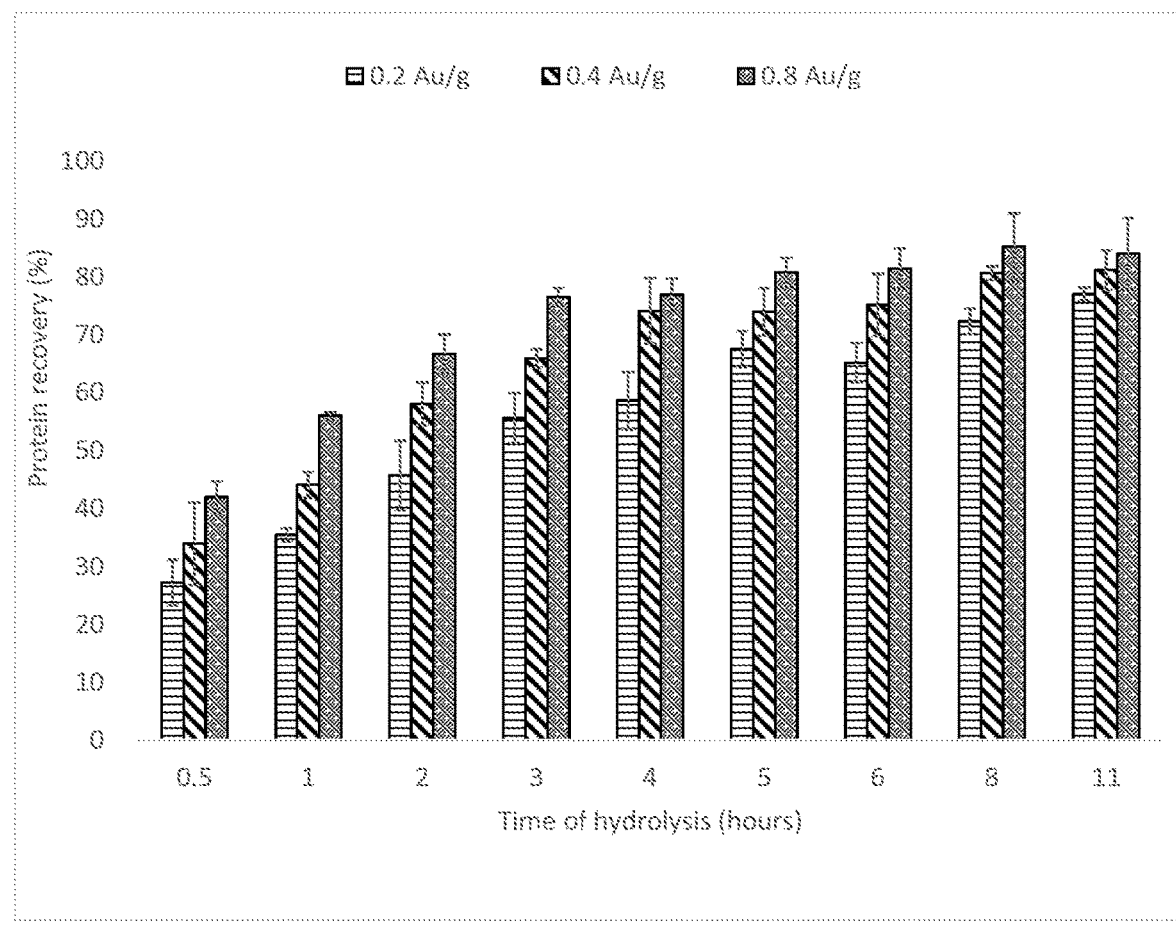
FIGS. 13A, 13B, 13C, and 13D are graphs showing reaction optimization and antioxidant activities of kafirin Alcalase hydrolysates prepared at combinations of different hydrolysis time and enzyme-to-substrate ratios of 0.2, 0.4, and 0.8 Au/g, with FIG. 13A showing Total protein recovery (%)
Figure 13B:
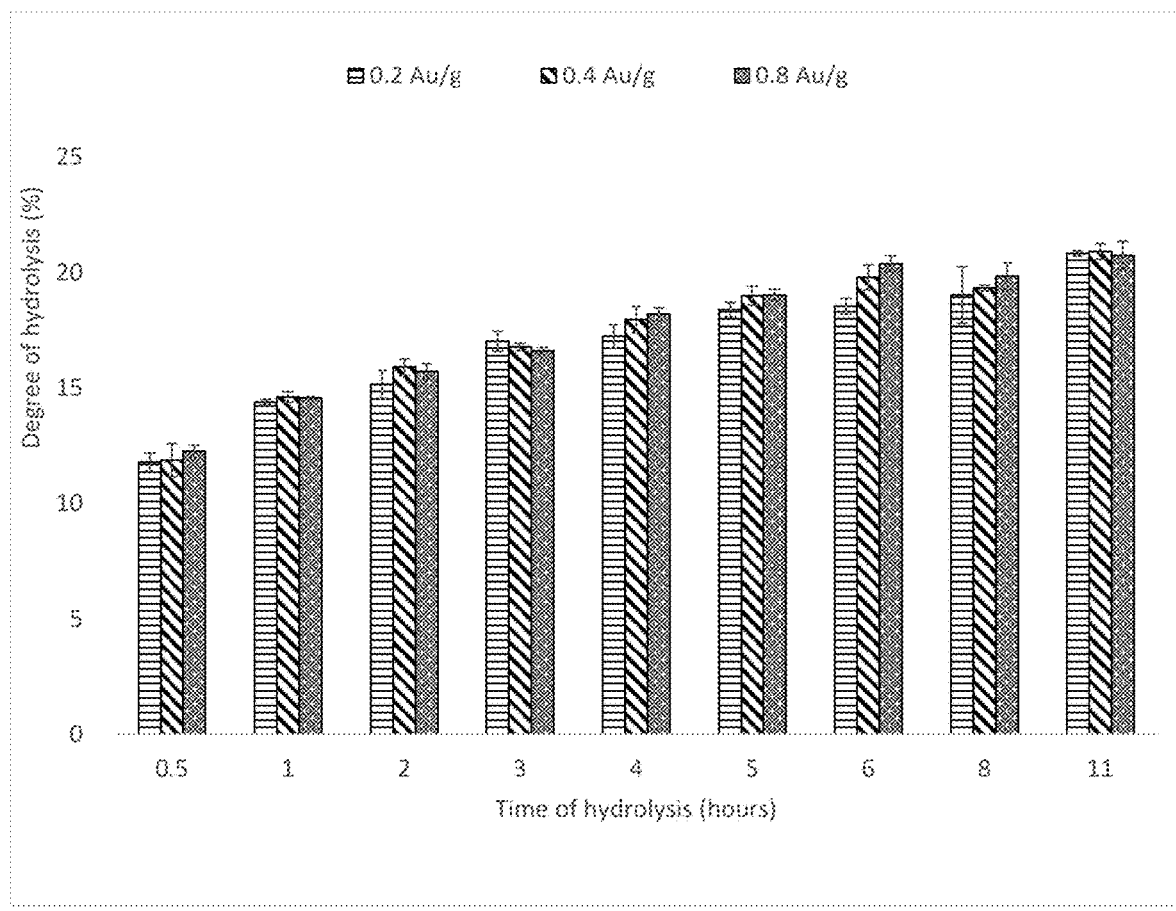
Figure 13C:
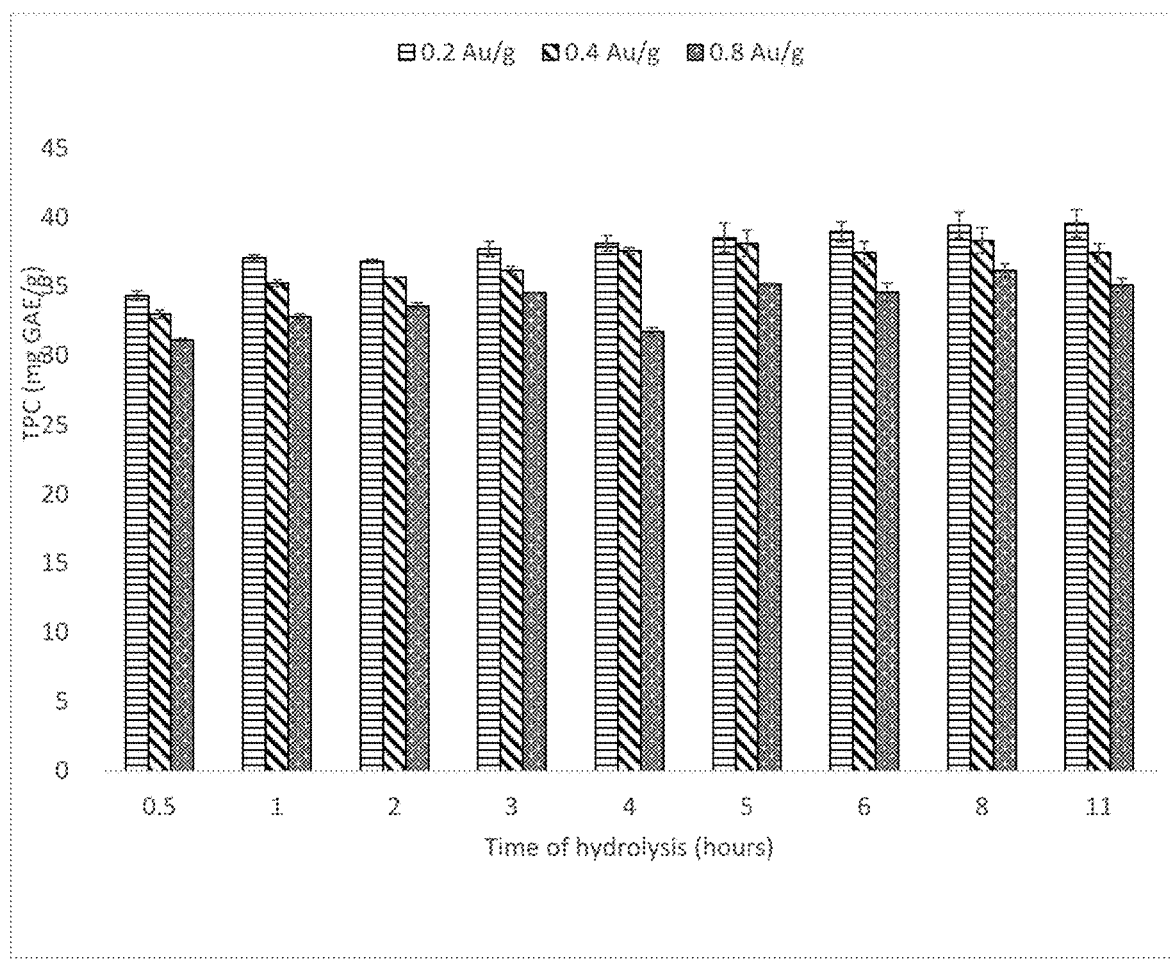
Figure 13D:
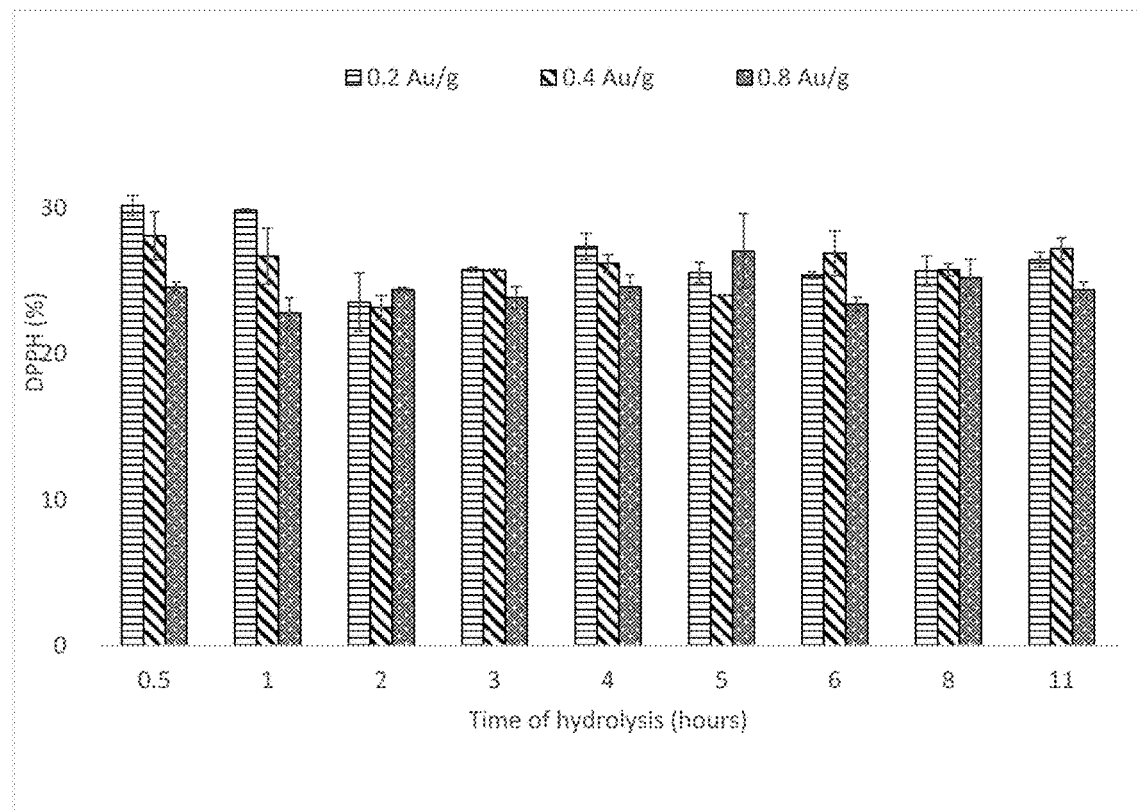

Purification and Identification of Antioxidative Peptides from Kafirin 3-10 kDa Neutrase Hydrolysates Gel Filtration of Kafirin Neutrase 3-10 kDa Hydrolysates In order to further fractionate the antioxidative peptides according to its molecular weight profile, 100 mg of 3-10 kDa Neutrase kafirin hydrolysates prepared at optimized conditions (17 hours, 0.4 Au/g, 4%) which showed highest antioxidant activity from previous results was loaded onto a Sephadex-G25 column for gel filtration chromatography. From the elution profile, three peaks appeared, and the entire eluent were divided into four major fractions (F1-F4) for analysis of their total phenolic content and antioxidant activities (FIGS. 11, 12A, and 12B). Overall, F1 represented the fraction of peptides that had larger molecular sizes and F4 had the smallest sizes as the larger molecules were eluted first and smaller molecules are retained longer by the gel medium. Fraction 2 exhibited significant higher value of TPC as well as DPPH % than other three fractions, thus was collected for peptide sequences identification. It was notable that, F4 possessed a negative DPPH % which might be due to its relatively higher salt content as well as other prooxidant components.

Identification of Representative Peptide Sequences from Gel Filtration

Not only peptide size, the solubility, the amino acid composition, characteristic peptides sequences, and abundance of certain amino acids may also impact the overall antioxidant activity of peptides and proteins. In order to characterize the peptide profile of potent antioxidant fraction, crude kafirin extracted from sorghum flour as well as isolated peptide fraction (F2) from gel filtration was subjected to RP-HPLC followed with MALDI-TOF/TOF MS analysis.

The spectrum of trypsin-digested kafirin was compared to known alpha, beta, and gamma kafirin protein patterns obtained from http://www.uniprot.org, and a 100% coverage to beta-kafirin, around 30-50% coverage to gamma-kafirin, and 0% coverage to alpha-kafirin was detected. Thus, the beta kafirin sequences were used to categorize the peptides present in hydrolysate sample. Peaks at 13.3-, 14.2-, 15.2-, and 17.2-minute represent largest area percentage from the HPLC chromatogram, which accounted for a total coverage of 26.25%, were collected and analyzed for sequences by MS. A total of 23 peptides were identified and summarized in Table 3.

TABLE 3

Representative antioxidant peptides in kafirin Neutrase hydrolysates.

| Peak | 13.3 min | 14.2 min | 15.2 min | 17.2 min |
|---|---|---|---|---|
| Area % | 9.95% | 5.77% | 6.43% | 4.10% |
| Coverage % | 92.70% | 40.10% | 70.30% | 66.70% |
| | QAMCGVV (SEQ ID NO: 7) | VAQNMP (SEQ ID NO: 16) | MRMMDMQS (SEQ ID NO: 19) | MDMQSRCQAM (SEQ ID NO: 26) |
| | AMCGVVQ (SEQ ID NO: 8) | VQSVVQ (SEQ ID NO: 17) | GGGLYPCAEY (SEQ ID NO: 20) | MMDMQSRCQA (SEQ ID NO: 27) |
| | SASALQM (SEQ ID NO: 9) | QPQCSP (SEQ ID NO: 18) | VAQVAQNMPA (SEQ ID NO: 21) | TPLAMAVAQVAQ (SEQ ID NO: 28) |
| | PAAQALTPL (SEQ ID NO: 10) | | AVAQVAQNMP (SEQ ID NO: 22) | QQMRMMDMQ (SEQ ID NO: 29) |
| | LPAAQALTP (SEQ ID NO: 11) | | TPCATSAAIPP (SEQ ID NO: 23) | |
| | LPSYCTTP (SEQ ID NO: 12) | | FLYPCAEYL (SEQ ID NO: 24) | |
| | SAAIPPYY (SEQ ID NO: 13) | | VQSVVQQLQ (SEQ ID NO: 25) | |
| | CGLYQLPS (SEQ ID NO: 14) | | | |
| | YALREQT (SEQ ID NO: 15) | | | |

Among the identified peptide sequences, it was found that, glutamine (Gln, Q) and alanine (Ala, A) were the top two amino acids, which were present in 18 and 16 sequences, respectively, out of the total 23 identified peptides. Thus, glutamine and alanine could be important constituent amino acids responsible for the antioxidant activities of hydrolysate peptides. Ala (A), Pro (P), Leu (L) and Cys (C) were in significantly high abundance in the identified sequences in this study (16 of Ala, 13 of P, 10 of L, 10 of C). Thus, they could be critically associated with the antioxidant activity of kafirin peptides.

A previous study found that all fractions of corn protein hydrolysate contained the sequence of Leu-Pro-Phe (LPF). Hence, this sequence may be related to their high antioxidant activity. In this study, the peptide Leu-Pro was found in three peptides, and 13 of the 23 identified peptides contained Pro, while 10 peptides contain Leu in their sequences. Peptides MDMQ (SEQ ID NO: 1) and VAQ were found to be the most frequently appeared sequences. VAQ tend to appear at the end terminals while MDMQ (SEQ ID NO: 1) were most often found within the sequences. Methionine (Met, M), valine (Val, V), tyrosine (Tyr, Y) are generally accepted as antioxidants or important constituent amino acids in antioxidant peptides reported by massive literatures. The frequent presence of Met and Tyr in the identified sequences (11 of Met, 8 of Val, and 6 of Tyr) also contributed to the overall antioxidant activities.

The determination of peptide sequences and structural analysis lay a solid foundation for future artificially synthesis and amplification of antioxidant peptides.

Conclusions

Enzymatic hydrolysis is an effective method to produce peptides with enhanced antioxidant activity from their parent proteins. The type of enzyme is a crucial factor impacting the protein recovery, DH, TPC, and the antioxidant capacity of consequent hydrolysates. Sorghum kafirin hydrolysates prepared with Neutrase displayed a balanced total protein recovery, DH, and antioxidant activity, thus was selected for further analysis. Other critical reaction factors were optimized to be protein content of 4%, enzyme-to-substrate ratio of 0.4 Au/g, and hydrolysis time of 17 hours. Hydrolysates with medium $M_w$ (3-10 kDa) exhibited higher TPC and antioxidative activities. The positive correlation between TPC and antioxidant activities indicated the phenolic peptides and phenolic compounds released during hydrolysis might be the components responsible for higher activities. The selected fraction of hydrolysates successfully retarded oil/lipid autoxidation and peroxidation in model systems. Upon further fractionation and peptide identification, glutamine and alanine were found to be the most abundant amino acids; MDMQ (SEQ ID NO: 1) and VAQ were the most frequent sequences, which could be associated with a higher activity.

This study provided an applicable processing technique for production of peptide antioxidants from sorghum kafirin. It was suggested that this naturally-extracted antioxidant could be used as alternatives to synthetic antioxidants or as synergetic effective component in improving the oxidative stability for various foods, beverages, animal feeds, pharmaceutical, industrial, and other applications. This work also delivered positive information to the sorghum ethanol industries by utilizing by-product such as distiller's grains as a protein source to produce peptide antioxidants as a potential revenue stream.

Example II

Reaction Optimization, Antioxidant Activity Characterization, and Peptides Identification of Sorghum Kafirin Hydrolysates Prepared with Alcalase Abstract Alcalase was a promising enzyme in producing antioxidative hydrolysates and peptides from sorghum kafirin according to preliminary experiment results. Hydrolysis of kafirin extracted from defatted white sorghum flour was conducted with combined treatment of varied hydrolysis time and enzyme-to-substrate ratios. The optimal reaction parameters were determined to be at substrate content of 4%, enzyme-to-substrate ratio at 0.4 Au/g, and hydrolysis time of 4 hours. At these conditions, hydrolysate was prepared and fractionated by ultrafiltration to categorize its molecular weight distribution, and fractions with different $M_w$ range were evaluated for their antioxidative capacity through free radical scavenging activity, metal chelating ability, reducing power, and oxygen radical absorbance capacity. Medium sized hydrolysate (5-10 kDa) exhibiting promising activities through in vitro chemical assays was subjected to further evaluation model systems. With an incorporation at 50 mg/mL oil, the formation of primary and secondary oxidation products was successfully inhibited by the selected fraction of hydrolysates by 68.26% and 37.83%, respectively, during the 14-day incubation period. When incorporated at 1.0 mg/g meat, the lipid peroxide products were reduced by 46.92% during the 12-day storage stage. This selected hydrolysate fraction was further fractionated on a Sephadex G-25 gel filtration column and F3 demonstrating stronger activities was pooled and analyzed by RP-HPLC, and a total of 26 peptide sequences were therefore identified from major peaks of HPLC by MALDI-TOF/TOF MS. Sequences QQWQ (SEQ ID NO: 2) and QWQQ (SEQ ID NO: 3) were found to be present in all isolated peaks. Hence, these sequences may be related to the antioxidant activity of kafirin hydrolysates peptides. A significant high level of hydrophobic amino acids was also found to contribute to the overall antioxidant activity of kafirin Alcalase hydrolysates by increasing the accessibility of antioxidants to hydrophobic targets. These combined results demonstrated that antioxidant peptides obtained from sorghum kafirin are capable of delaying or inhibiting the oil and fat peroxidation.

Introduction

Adding values to under-utilized crops and optimize their values for various industrial applications is an increasing trend. Sorghum is the third largest cereal crop in U.S. mainly used as animal feed and starch source for biofuel. The by-products from sorghum ethanol industries (e.g., DDGS) are a premium protein source which could be potentially used for manufacture of value-added products such as peptide antioxidants.

Driven by the heightened safety concerns over synthetic antioxidants and consumers' preference for natural ingredients, the development of novel natural antioxidants have drawn growing interests. Protein has been on the top-ten driving factor in current markets with extensive popularity. Peptide antioxidants are naturally existed (e.g., GSH) and can be produced from dietary protein hydrolysates, which exert antioxidative performances through multiple pathways such as scavenging free radicals, chelating transition metals, reducing oxidized substances, interrupting the decomposition of hydroperoxide, forming physical barriers hindering access of prooxidant to targets and so on. Peptide antioxidant is naturally-derived, efficient, generally considered as safe at high dosages, and able to serve as an energy source and amino acid and provider. Besides, due to the surface amphiphilicity, peptide antioxidants can also serve as functional ingredients with special properties (e.g., gelation, emulsifying, foaming, water and/or oil binding capacity). Thus, they are promising alternatives to synthetic antioxidants to be incorporated into various food products as additives in protecting lipid and/or oil from peroxidation.

Upon enzymatic hydrolysis, native globular matrix of intact proteins will be cleaved, characteristic structures (e.g., functional R groups, structural domains) attributing to the antioxidative activities will be exposed, and specific peptide sequences will be released. The solubility of hydrolyzed proteins is increased, yet, the amino acid profile and antioxidant activities could remain essentially unchanged or improved in some fractions. The resulting hydrolysates can be purified and isolated by various techniques to obtain peptides with enhanced activities.

The selection of enzyme is important in determining the end-use properties of hydrolysates. Alcalase is a food-grade commercial protease in liquid form prepared by submerged fermentation of a selected strain from *Bacillus licheniformis*, with Subtilisin Carlsberg as a major proteolytic component. It is a serine endopeptidase with broad specificity, which cleaves peptide bonds at the interior of the chain and produces peptide with varied sizes. Alcalase is readily soluble in water at all concentrations and has a relatively low bulk sale price, which has been widely used in food industry to hydrolyze plant and animal proteins for improvements in functional and nutritional values. Alcalase, alone or as a partial step, can be used for generation of antioxidative peptides from plan and/or animal proteins such as those from wheat germ, barley glutelin, rice bran protein, corn gluten, zein, green tender sorghum protein, soy protein, chickpea protein, rapeseed, sardine by-product proteins, egg yolk, pollack skin and so on. The obtained bioactive peptides prepared with Alcalase are more resistant to digestive enzymes. Alcalase is completely soluble in water with all concentrations and available in food grade, make it a readily used enzyme in protein dispersions in producing water soluble peptides.

According to the results of preliminary experiments, sorghum protein kafirin hydrolysates prepared with Alcalase exhibited promising antioxidative activities as well as good protein recovery yield. Thus, Alcalase was selected to hydrolyze kafirin in producing antioxidative peptides in this study. The objectives of this study were to: 1) optimize the reaction conditions of kafirin hydrolysis using Alcalase; 2) evaluate the antioxidant performances of kafirin Alcalase hydrolysates antioxidants via in vitro chemical assays and model systems; and 3) purify the using different characterization techniques and identify the major molecular weight distribution identify the structural characteristics including molecular weight distribution, amino acid composition, and characteristic peptide sequences of the antioxidative activities.

Materials and Methods
  Materials and Chemicals
  The materials and chemicals used for the study in this chapter is the same as those used in Example I, thus, will not be listed.
  Preparation of Sorghum Protein Hydrolysates
  The procedures used in preparation of sorghum hydrolysates for this study were similar to those described in Example I, which include the defatting of sorghum flour, extraction of sorghum kafirin, and enzymatic hydrolysis of kafirin, except that Alcalase protease was used.
  Evaluation of Hydrolysis Process
  The process of hydrolysis was evaluated and optimized as determined by several indicators including total protein recovery, degree of hydrolysis, and total phenolic content as previously discussed.
  Fractionation and Identification of Antioxidative Peptides
  The only difference from the study in Example I was ultrafiltration using a stirred cell instead of centrifugal tubes, which will be described as followed. Other fractionation and identification procedures including gel filtration with Sephadex G-25, RF-HPLC, and MALDI-TOF/TOF MS followed the same procedure as previously described.
  Ultrafiltration with Stirred Cell
  The ultrafiltration was achieved using an Amicon® Stirred Cell (EMD Millipore Corporation, Billerica, Mass., USA) sequentially assembled with Ultracel® Ultrafiltration Discs (EMD Millipore Corporation, Billerica, Mass., USA) with molecular weight cut-off at 10 k, 5 k, 3 kDa and 1 kDa. New membranes were floated in deionized water with skin (glossy) sides adown for 24 hours with water changed at least three times to remove the pretreated glycerine residues. The membrane was then placed into the stir cell and loaded with hydrolysate solution at 5 mg/mL. The stir cell was placed on top of a magnetic stirrer at 60 rpm. Compressed nitrogen was connected to the stir cell at a maximal pressure of 60 psi to accelerate the penetration process.
  Assessment of Antioxidative Activity
  In addition to the assays and model systems described in Example I, ABTS radical scavenging activity was also employed as depicted below.
  ABTS Radical Scavenging Assay
  The ABTS radical scavenging activity of protein hydrolysates or peptides was determined. The ABTS stock solution was made by mixing equal amount of 7.4 mM ABTS solution and 2.6 mM potassium persulfate solution and stored for 12-16 h in dark at room temperature to generate ABTS radicals. The ABTS stock solution was then diluted with deionized water to achieve an absorbance of 1.1±0.02 at 734 nm on a spectrophotometer. 2.85 mL of the diluted ABTS radical solution was mixed with 0.15 mL of sample solution and incubate at room temperature in darkness for 10 minutes before reading its absorbance at 734 nm. Deionized water was used as a blank control. The ABTS radical scavenging activity was calculated using follow equation:

$$ABTS \% = \frac{A_b - A_s}{A_b} \times 100\%$$

where $A_b$ was the absorbance of blank and $A_s$ was the absorbance of sample.
  Statistical Analysis
  The statistical analysis method used in this study was same as described in Example I.
Results and Discussion
  Reaction Optimization of Kafirin Enzymatic Hydrolysis
  Enzyme type, substrate, and hydrolysis conditions have a synergistic effect on the production of peptide. 4% kafirin solution was hydrolyzed with Alcalase at 0.2, 0.4, and 0.8 Au/g enzyme-to-substrate ratio with varied hydrolysis time. Degree of hydrolysis (DH), total protein recovery, total phenolic content (TPC) and DPPH radical scavenging activities (DPPH %) were evaluated for the resulting hydrolysates (FIGS. 13A-13D).

Percentage of water-soluble hydrolysate yield was calculated as total protein recovery and used to determine the efficiency of the hydrolysis process. Total protein recovery was found to increase with extended hydrolysis time. After 2 hours hydrolysis, yields for all three enzyme-to-substrate ratios are over 50%, and after 4 hours, kafirin with 0.4 Au/g enzyme reached a yield over 74%, which indicated that majority of high $M_w$ proteins were degraded into low $M_w$ soluble peptides and amino acids through peptide cleavage. An obvious enhancement in total protein recovery was observed when increased enzyme-to-substrate ratio from 0.2 to 0.4 Au/g. However, there was no noteworthy enhanced yield when increase enzyme-to-substrate ratio to 0.8 Au/g.

Besides, DH increased consistently with prolonged hydrolysis time until reached plateau at around 4 hours. This was because at initial stage, the substrate concentration as well as the enzyme activity were relatively higher, which led a higher rate of peptide bond cleavage and protein hydrolysis. As the hydrolysis progressed, the rate of hydrolysis decreased when the system tended to reach reaction equilibrium.

DPPH is a stable free radical that has an intrinsic purple color in ethanol solvent, which can be detected at 517 nm. When encounters an electron-donating substrate, DPPH radical accepts an electron and becomes a stable diamagnetic molecule hence loses the purple color as well as a reduced absorbance at 517 nm. Therefore, the ability of kafirin hydrolysate to act as electron donors in its antioxidative performances can be tested by DPPH radical scavenging activity. The DPPH % of kafirin hydrolysates after 3 hours of hydrolysis was 23.89%-27.23% at 5 mg/mL. The abnormal high value of DPPH % at 0.5 hour might be due to the intrinsic activity of the protease. All other hydrolysates exhibited fairly similar values of DPPH % and no obvious increase of DPPH % was observed when longer hydrolysis time was applied. This result indicated that kafirin hydrolysates are antioxidants that can act through radical scavenging activity. The antioxidant activity was not enhanced or decreased with extended hydrolysis time, which might be due to the fact that extended hydrolysis time only increased the hydrolysate yield but did not changed the hydrolysate nature.

TPC of Alcalase hydrolysates was between 31.13 and 39.47 mg GAE/g. While TPC was increased with hydrolysis time extended from 0.5 hour to 2 hours for all three enzyme-to-substrate ratios, increasing hydrolysis time from 4 hours to 11 hours did not make a huge impact on TPC.

Thus, protein content of 4%, enzyme-to-substrate ratio at 0.4 Au/g, and hydrolysis for 4 hours were determined to be optimal reaction conditions with a good balance of protein recovery, antioxidant activity, and production cost for kafirin hydrolysis with Alcalase.

Ultrafiltration of Kafirin Alcalase Hydrolysates

Previous studies have revealed that the antioxidative activities of hydrolysate peptides is dependent on their $M_w$ distribution. Kafirin Alcalase hydrolysate was prepared at previously determined optimal reaction conditions (protein content of 4%, enzyme-to-substrate ratio of 0.4 Au/g and hydrolysis time of 4 hours). It was then sequentially fractionated in an ultrafiltration stirred cell coupled with $M_w$ cut-off membranes 10 k, 5 k, 3 k, and 1 kDa.

Figure 14:
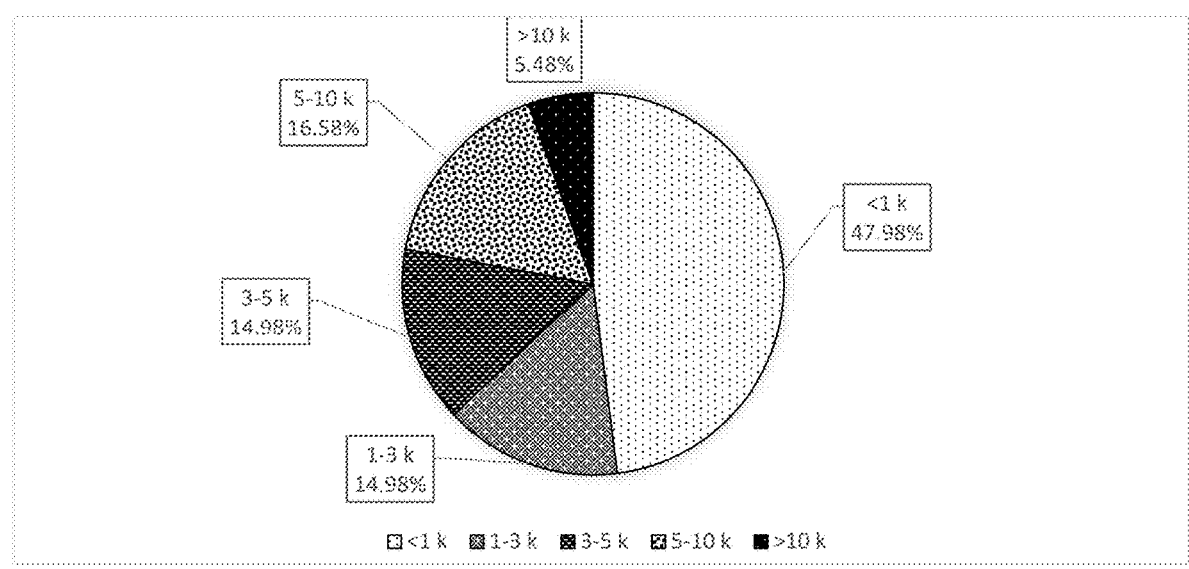
FIG. 14 is a pie chart showing distribution of ultrafiltrated fractions of kafirin Alcalase hydrolysate prepared at enzyme-to-substrate ratio of 0.4 Au/g and hydrolyzed for 4 hours followed with membrane filtration using 10 k, 5 k, 3 k, and 1 kDa membranes.

FIG. 14 shows the $M_w$ distribution profile of the five fractions. The yield of each fraction was found to decrease with increased fraction size. The hydrolysate in <1 kDa fraction (47.98%) was significantly higher than others. 1-3 kDa (14.97%), 3-5 kDa (14.98%), and 5-10 kDa (16.58%) shared similar portions while >10 kDa fraction had the lowest percentage (5.48%). Since percentage yield of protein hydrolysates is not commonly reported, adequate comparison could not be compared.

Figure 15A:
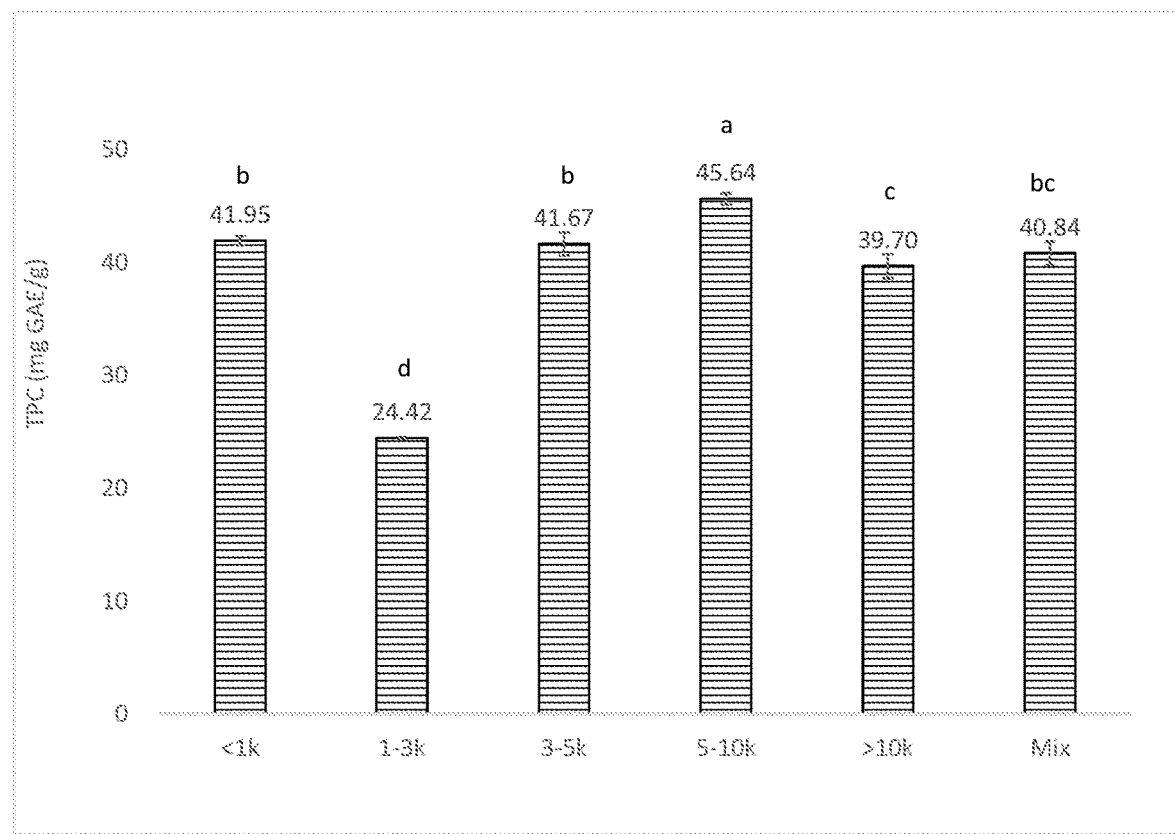
FIGS. 15A, 15B, 15C, 15D, and 15E are graphs showing total phenolic content and antioxidant activities of kafirin Alcalase hydrolysate ultrafiltrated fractions prepared at enzyme-to-substrate ratio of 0.4 Au/g and hydrolyzed for 4 hours followed with membrane filtration using 10 k, 5 k, 3 k, and 1 kDa membranes; with FIG. 15A showing Total phenolic content (mg GAE/g)

All fractionated fractions of hydrolysates as well as the hydrolysate mixture were evaluated for total phenolic content as shown in FIG. 15A. Except for 1-3 kDa fraction having the lowest TPC, other hydrolysate fractions all had TPC over 39 mg GAE/g. With TPC of 45.64±0.51 mg GAE/g, 5-10 kDa fraction had the highest value (P<0.05) than other fractions.

Figure 15B:
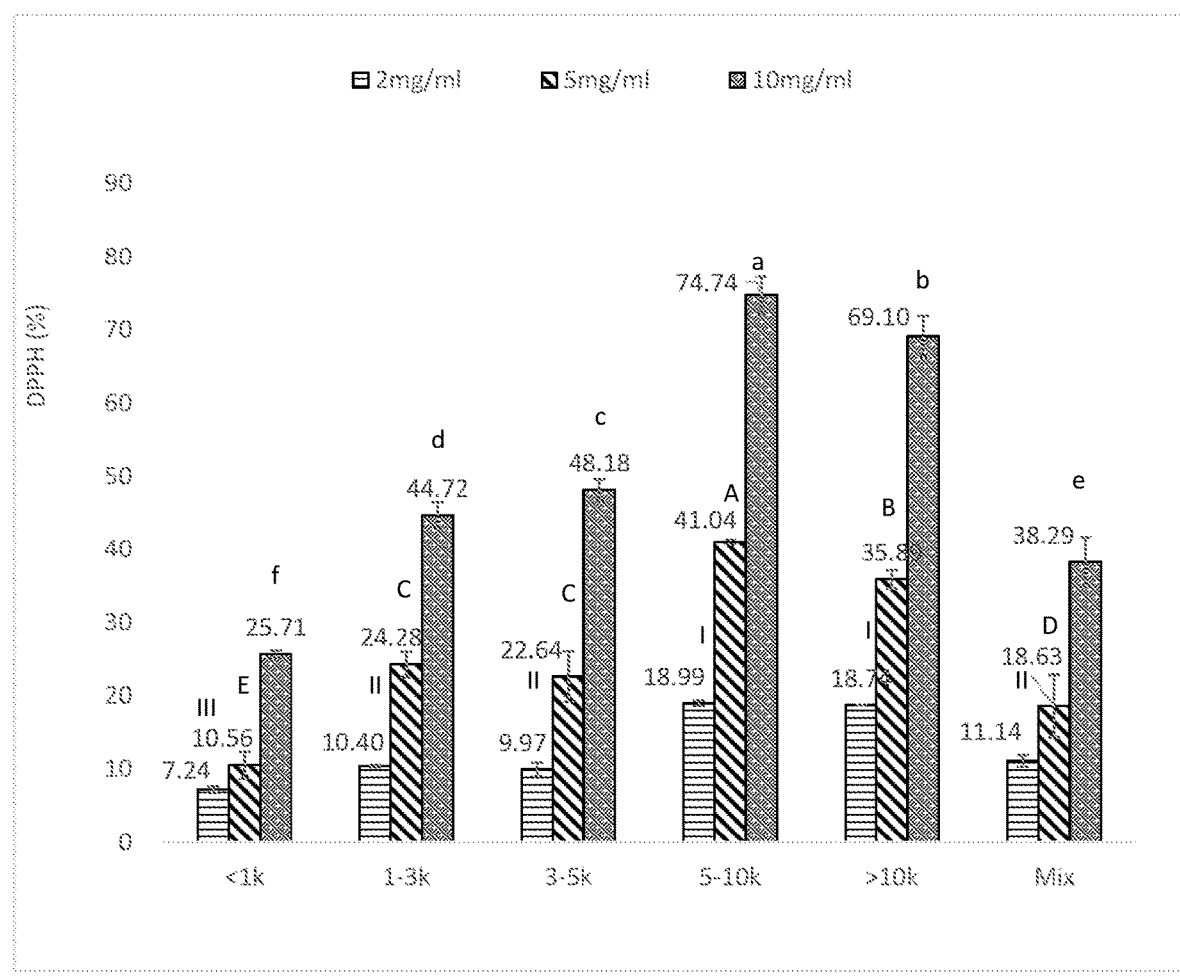

DPPH % was measured for each of the filtrate fraction plus the mixture as shown in FIG. 15B. Overall, 5-10 kDa (74.74±2.50% at 10 mg/mL) fraction had the significantly (P<0.05) higher DPPH % than other fractions, and <3 kDa (25.70±0.48% at 10 mg/mL) fraction was the lowest. The scavenging activity was linearly dose-dependent. This result revealed that the free radical scavenging activity is closely related to the $M_w$ distribution of the substrate hydrolysate. Medium sized kafirin hydrolysates (5-10 kDa) were found to possess higher DPPH scavenging activity which might be due to the substrates in 5-10 kDa contain more efficient electron donors thus were able to stabilize free radicals to less reactive products.

Figure 15C:
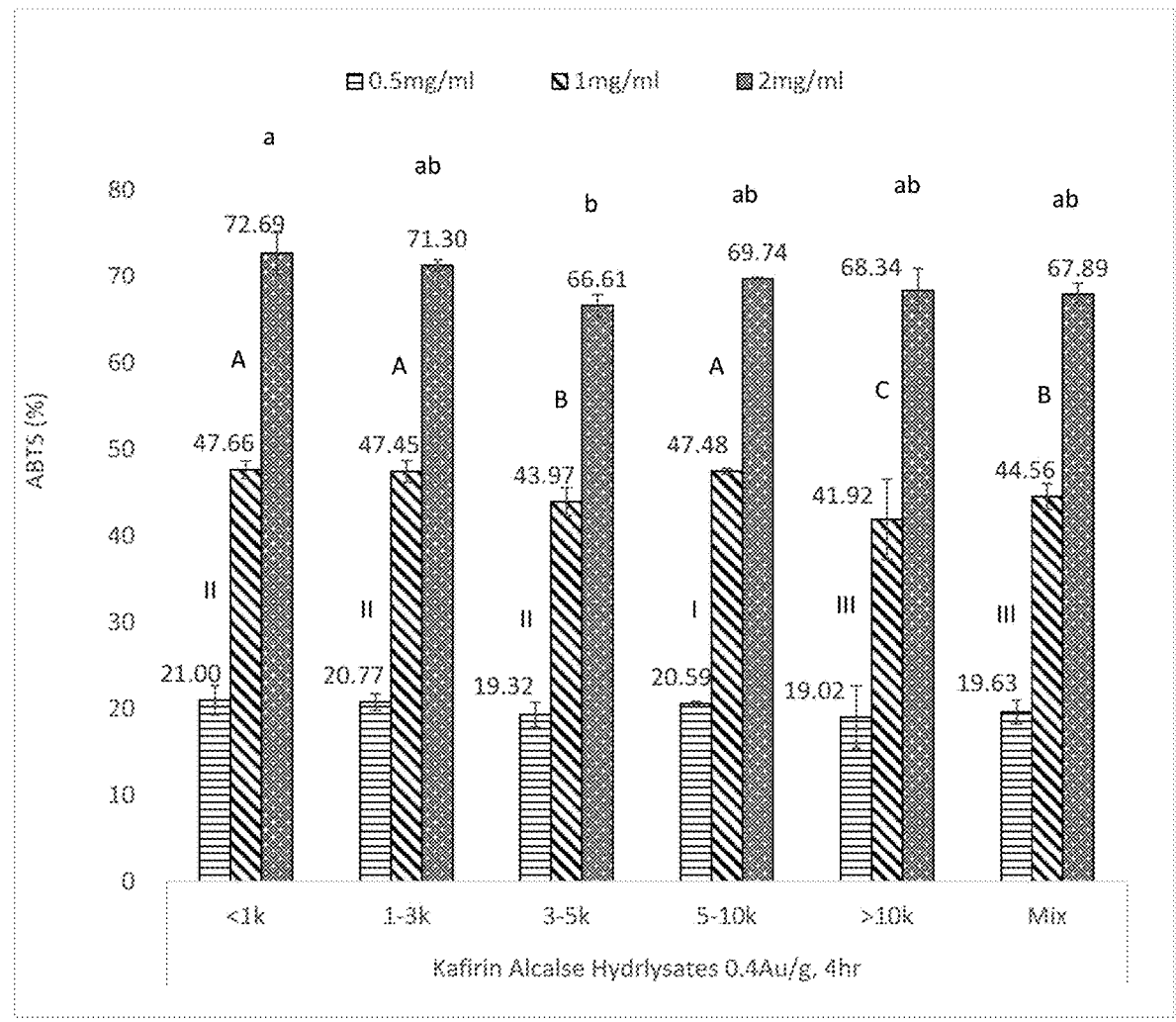

ABTS radical scavenging assay (ABTS %) is widely used to test the hydrogen donating ability of the compounds in evaluation of the antioxidative activity of a substrate. ABTS radical showing a green color can be suppressed through radical scavenging ability of substrates. The discoloration can be monitored at decreases in absorbance at wavelength 700 nm and the inhibition percentage was used as an indicator for ABTS scavenging ability. ABST radical was scavenged by the hydrolysates in an amount-dependent manner. As shown in FIG. 15C, all 6 fractions of hydrolysates displayed excellent ABTS %. The scavenging activity increased accordingly with an increased substrate concentration. There were no significant differences (P<0.05) in ABTS % assay among the medium- and small-sized fractions of kafirin hydrolysates.

Figure 15D:
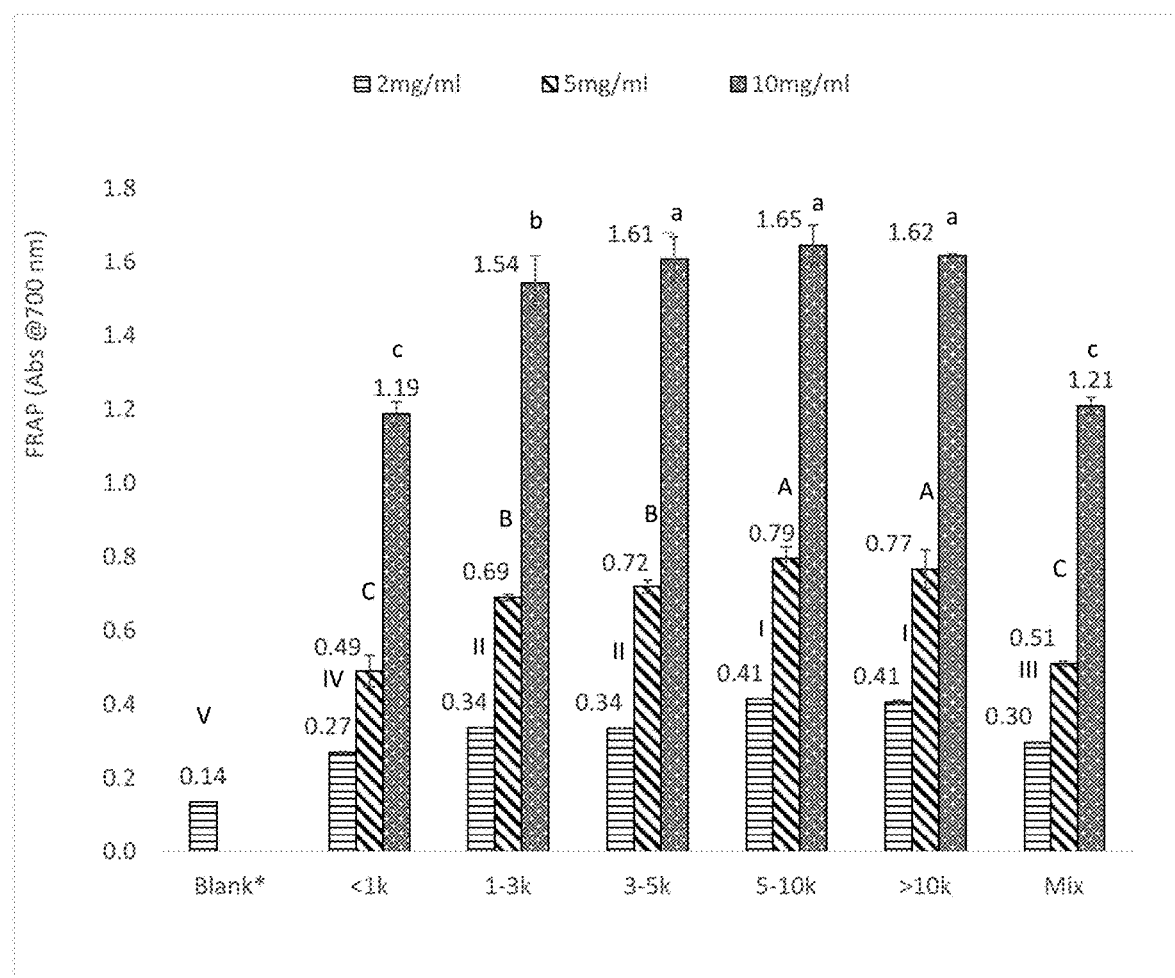

Reducing power assay is a typical electron-transfer method involving one redox reaction showing the presence of the compounds as a hydrogen atom donator to stabilize the free radicals, which is associated with the exposure of electron-dense amino acid side chain groups and with the $M_w$ of the peptides. From FIG. 15D, all fractions of kafirin hydrolysate resulted in significantly (P<0.05) higher absorbance values ($A_{700}$>1.18 at 10 mg/mL) over blank control ($A_{700}$=0.136±0.048), which indicated an excellence reducing power ability of kafirin hydrolysate to reduce $Fe^{3+}$ to $Fe^{2+}$. Among all six fractions, medium—(5-10 kDa) and large-sized (>10 kDa) hydrolysates were found to be stronger reducers.

Figure 15E:
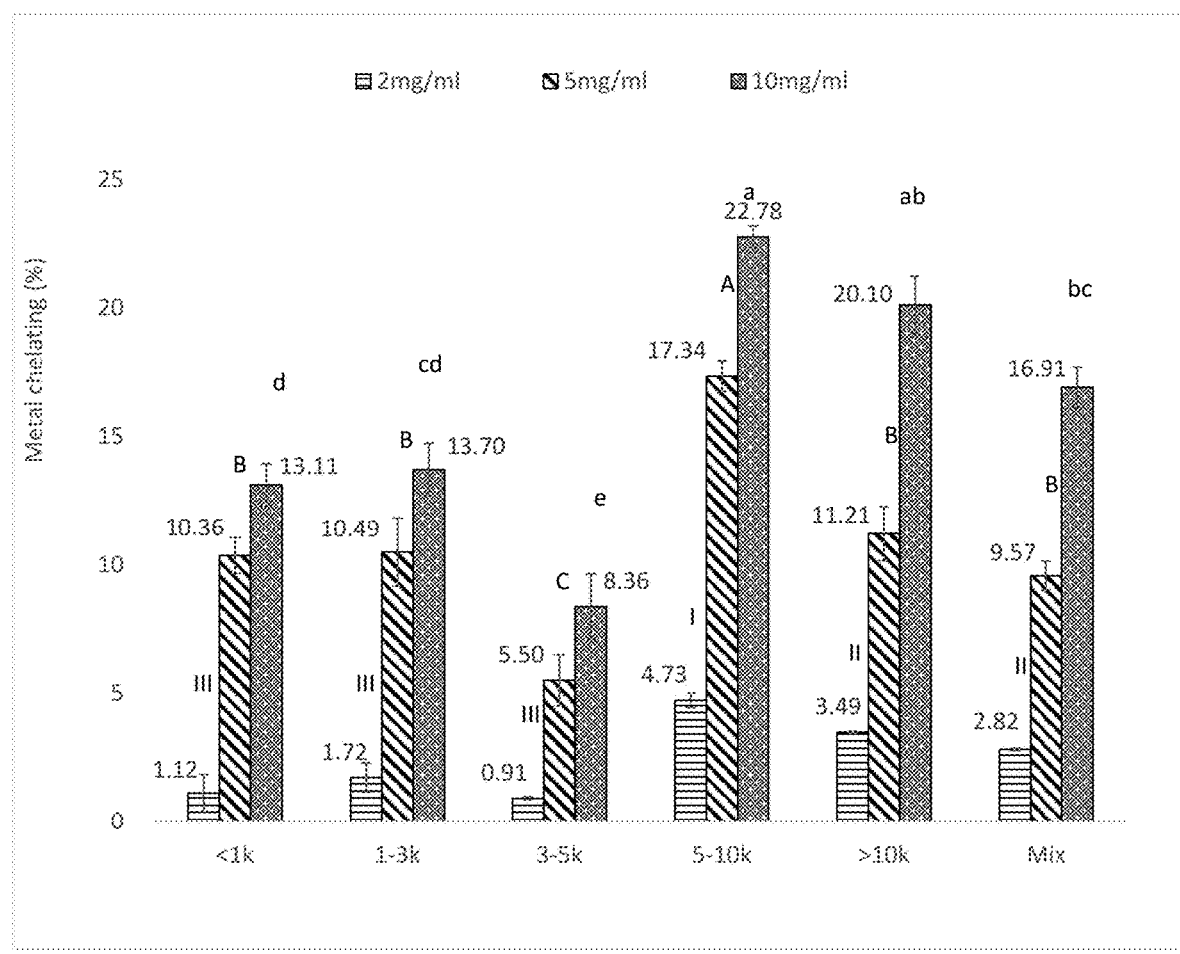

No food system can be considered free of metal ions. Transition metals such as $Fe^{2+}$ and $Cu^{2+}$ are well-known catalyst of lipid peroxidation chain reactions. Thus, chelation of metal ion is an important pathway of antioxidant action. In this assay, after adding antioxidant to ferrous chloride, the un-chelated ferrous iron was determined measuring the formation of ferrous iron ferrozine complex at 562 nm. After reaction, a lower absorbance indicated a higher metal chelating ability. As shown in FIG. 15E, kafirin Alcalase hydrolysates exhibited a metal chelating ability ranging from 8.36% to 22.78% at 10 mg/mL. It appeared that 5-10 kDa fraction had significant (P<0.05) higher chelating activity than other fractions especially at low dosage. This result indicated that kafirin Alcalase hydrolysates demonstrated a remarkable iron binding capacity, which may be related to its action as peroxidation protector.

The ferrous ion chelating ability may also contribute to their hydroxyl radical scavenging effects of antioxidants due to the combined effects.

Overall, medium sized kafirin Alcalase hydrolysate displayed higher antioxidant activities than other fractions with a good recovery.

Lastly, some researchers found a positive correlation between antioxidant activity and TPC, however, such relationship was not observed in this study.

Inhibition of Lipid Oxidation in Model Systems

Oil-in-Water Emulsion System

Oil-in-water emulsions exists in many food products such as soups, sauces, beverages, and so on. Oxidation of emulsions is a common problem that can cause texture alteration, development of rancid odor, and loss of nutrition profiles. Thus, the ability to improve the oxidative stability of food emulsion is an important indicator of peptides antioxidants capacity.

Figure 16A:
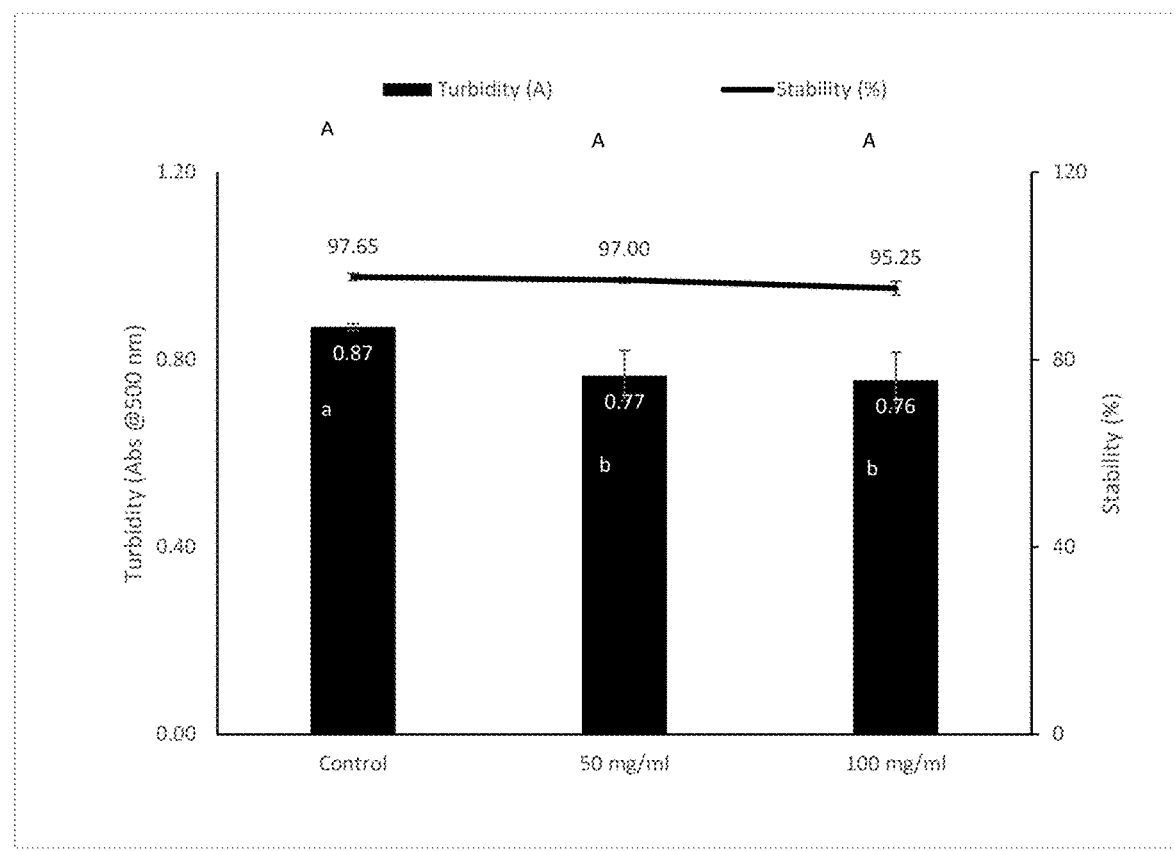
FIGS. 16A, 16B, and 16C are graphs showing inhibition effect of kafirin Alcalase 5-10 kDa hydrolysate prepared at enzyme-to-substrate ratio of 0.4 Au/g and hydrolyzed for 4 hours in an oil-in-water emulsion model system added with 50 and 100 mg/mL oil, with FIG. 16A showing emulsion turbidity (Abs at 500 nm) and stability (%); with FIG. 16B showing POV (mM cumene hydroperoxide equivalent)

Kafirin Alcalase 5-10 kDa hydrolysate was incorporated when preparing soy oil-in-water emulsion samples stabilized with Tween-20. Changes in emulsion physical texture and structure was validated by measuring the emulsion turbidity and stability. As shown in FIG. 16A, the turbidity of emulsion without hydrolysate was $A_{500}=0.87\pm0.007$, and the addition of hydrolysate at 50 mg and 100 mg hydrolysate per mL of soy oil decreased the emulsion turbidity to $A_{500}=0.77\pm0.053$ and $A_{500}=0.76\pm0.059$, respectively. Meanwhile, the emulsion stability did not have a significant difference among the samples (P<0.05).

Figure 16B:
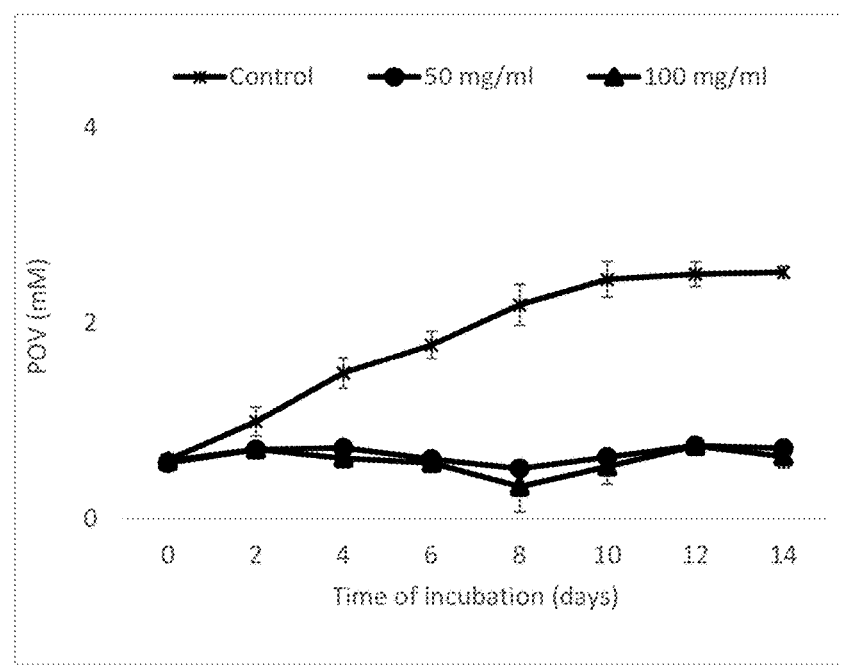
Figure 16C:
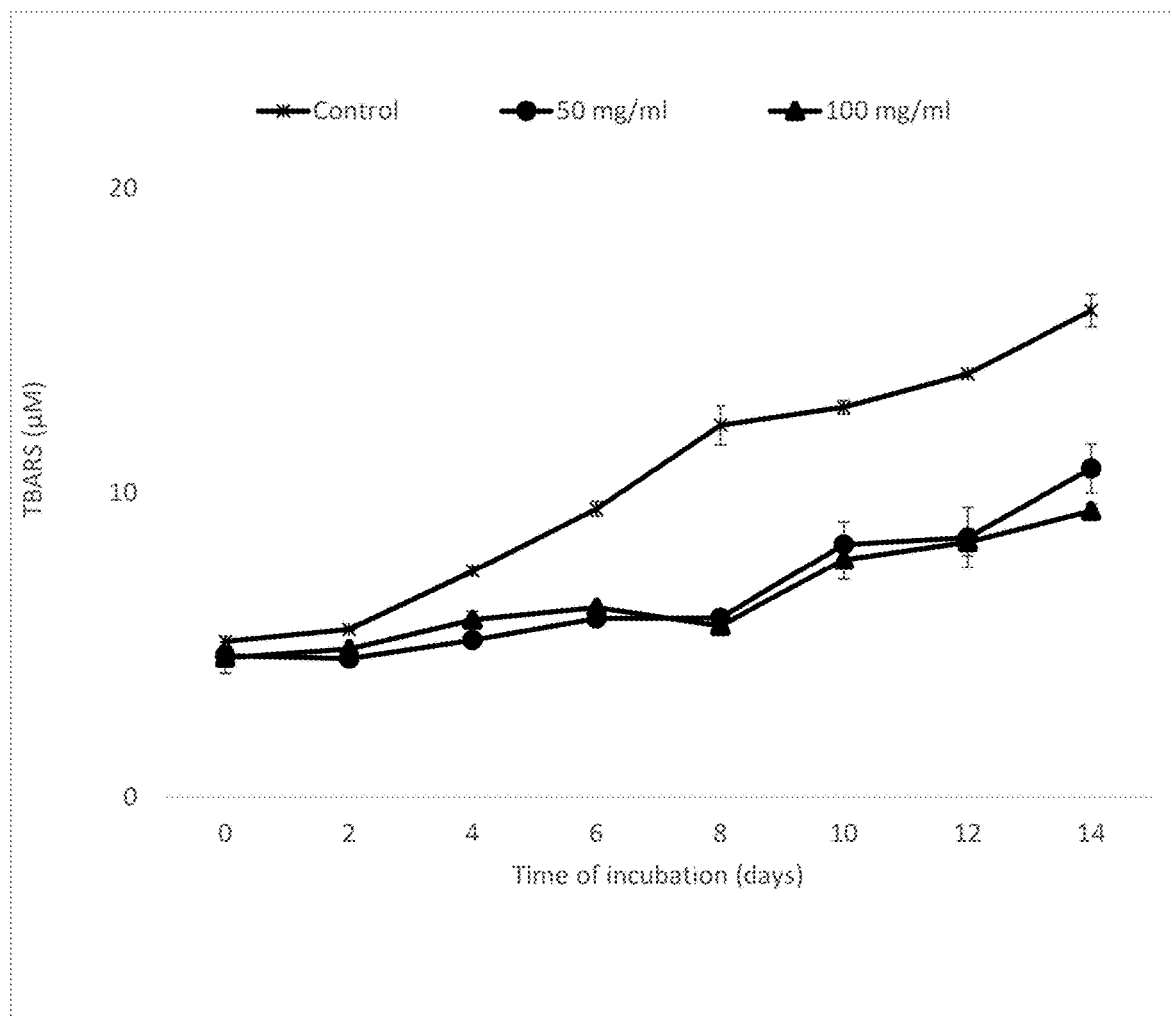

The presence of hydrolysate displayed inhibition effect regarding the formation of both primary and secondary oxidation products, peroxide values (POV) and thiobarbituric acid reactive substances (TBARS), in a continuous phase compared to the control as illustrated in FIGS. 16B and 16C. During 14 days of incubation period at 37° C., the emulsion sample with addition of 50 mg/mL displayed an inhibition rate of POV up to 76.56% (at day 8) and had an average inhibition of 68.26±9.06%. Where the inhibition rate of TBARS was highest to be 51.89% (at day 8) and was averaged to be 37.83±7.56%. Increased concentration of hydrolysate at 100 mg/mL displayed an increase of inhibition effect of oxidation, where, POV inhibition rate up to 85.02% at day 8, and had an average inhibition value of 72.48±9.10%, TBARS was decreased up to 54.03% at day 8, and averaged at 38.34±10.50%.

This experiment results could serve as evidence indicating the antioxidative activities of fractionated kafirin hydrolysate in decreasing lipid hydroperoxide and TBARS formation, therefore, to stabilize the oil-in-water emulsions and retard emulsion oxidation. The activity of the hydrolysates could be due to multiple mechanisms, as previously discussed. Their free radical scavenging activities, chelation of transition metal ions, reducing power, and interrupting the decomposition of hydroperoxide into secondary products thus inhibit TBARS formation all contribute to the overall antioxidant activity. In addition, Alcalase is an endo-protease which could perform both subtilisin and glutamyl activities, thus, the released peptides with Glu at C-terminal and hydrophobic patches in the sequences ultimately increased the overall hydrophobicity of hydrolysates, which assisted the adsorption of peptide molecules with oil droplets in emulsions. Proteins and peptides at oil-water interfaces could form a physical barrier to protect the interior of oil droplet, and also hinder the access of prooxidants in the aqueous phase. This concluded that kafirin hydrolysate could be used as potential antioxidants and/or functional ingredient for formulating emulsion-type foods with enhanced stability against lipid and/or oil oxidation.

Ground Meat System

Reducing hydrogen and lipid peroxides in food products are important reactions because they are able to decompose to carbonyl molecules associated with rancid aroma and form free radicals. The lipid oxidation process in food products is highly dependent on the presence of pro-oxidants such as lipoxygenase, singlet oxygen molecules and transition metals such as Fe and Cu. Kafirin 5-10 kDa Alcalase hydrolysate fraction exhibited strongest antioxidative activities in primary experiments was inferred to be effective in inhibiting and retarding lipid oxidations through pathways as previously discussed.

Figure 17:
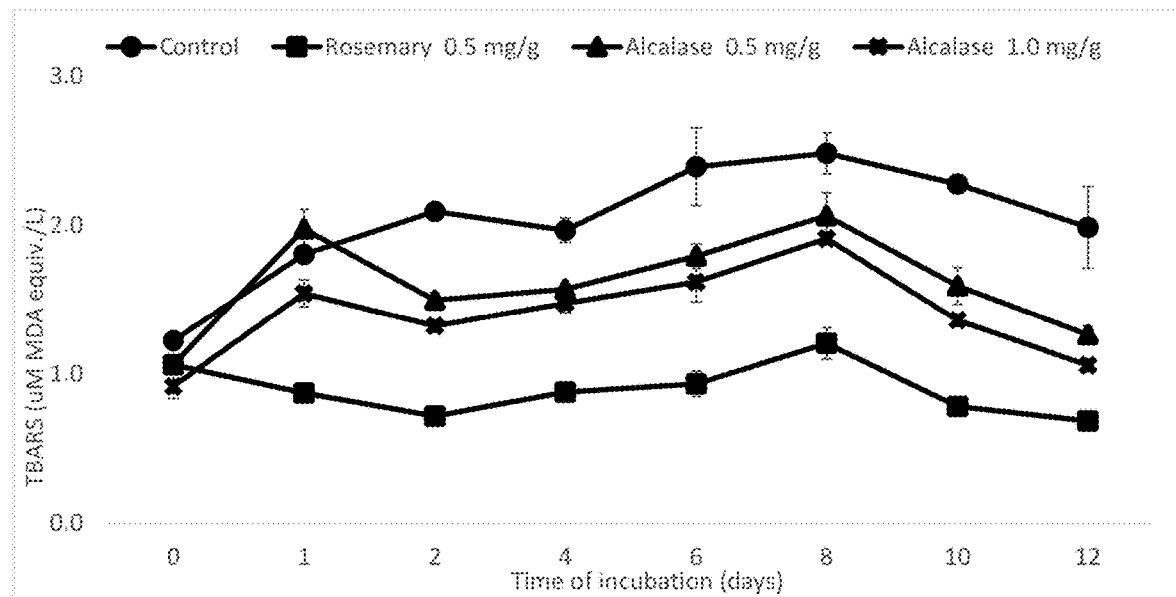
FIG. 17 is a graph showing inhibition effect shown as TBARS of kafirin Alcalase 5-10 kDa hydrolysate prepared at enzyme-to-substrate ratio of 0.4 Au/g and hydrolyzed for 4 hours in a ground meat model system added with 0.5 and 1 Mg/g meat.

Concentration of secondary oxidation product TBARS was measured for meat samples incorporated with hydrolysates and was compared to that prepared with rosemary extract and a blank control (i.e., no antioxidant addition) as shown in FIG. 17. With hydrolysate added at 0.5 mg and 1.0 mg per gram of meat, TBARS was reduced throughout the entire 12-day incubation period compared with the blank control. At day 0, all meat samples contained similar TBARS content and from day 2, the inhibition effect of hydrolysates had begun to be apparent. At the end of the incubation, the TBARS was decreased by 35.34% and 43.17% for 0.5 mg/g and 1.0 mg/g, respectively, which indicated that the oxidation activities of lipid in ground meat were markedly inhibited by the addition of the kafirin hydrolysates. The average inhibition of TBARS during the 12-day incubation was 26.18±7.06%, and 46.92±15.98%. However, the inhibition performed by hydrolysates were not as efficient as rosemary extract did, which was posed an average of inhibition of 59.55±6.56%. This might be due to the impurity of kafirin hydrolysates, which could contain both antioxidative and prooxidative components. Hence, further fractionation of hydrolysates and identification of major peptide sequences responsible for the activities is needed.

Figure 18:
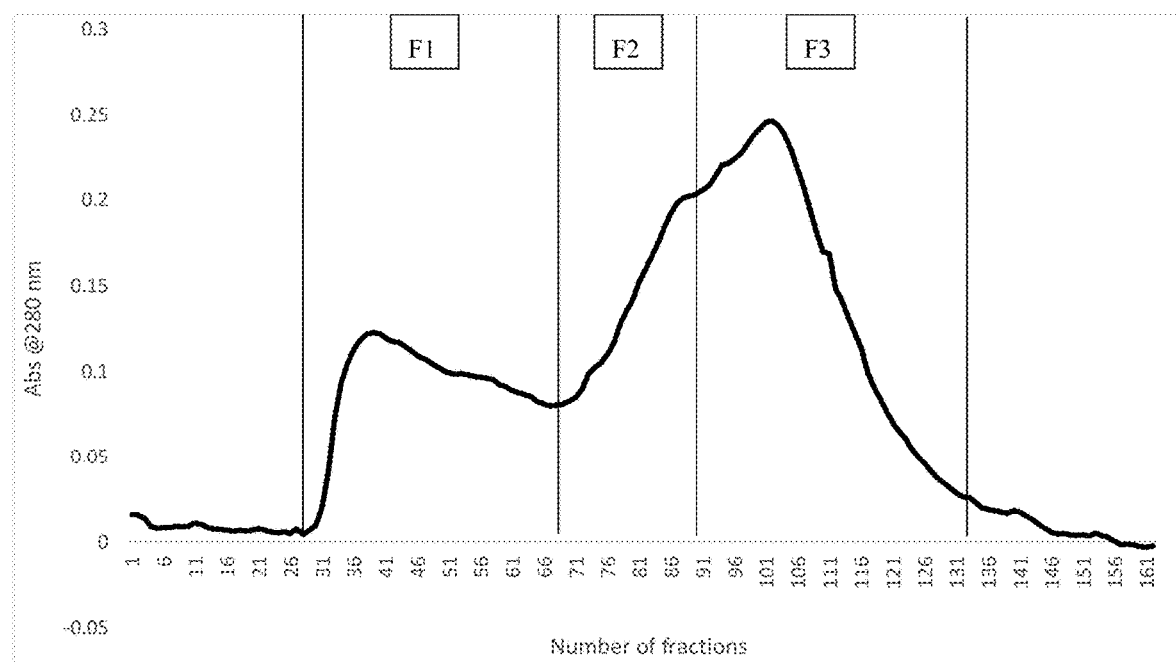
FIG. 18 is a graph showing gel filtration chromatogram of kafirin Alcalase 5-10 kDa hydrolysate prepared at 0.4 Au/g and hydrolyzed for 4 hours in a Sephadex G-25 column (26 mm×850 mm)
Figure 19A:
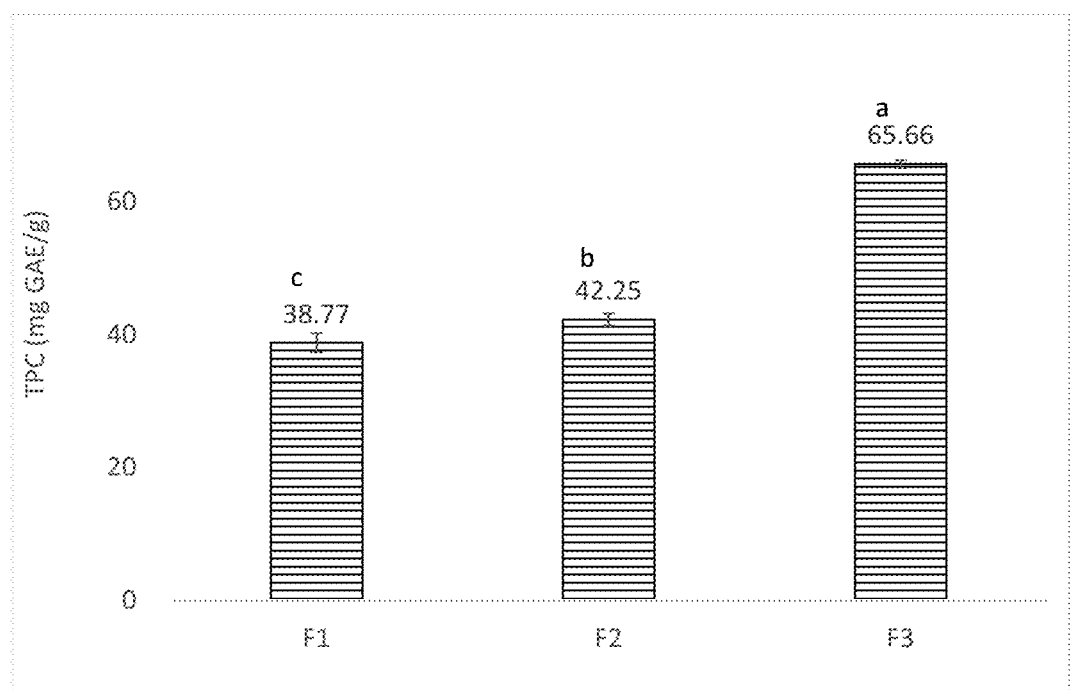
FIGS. 19A, 19B, 19C, and 19D are graphs showing Total phenolic content and antioxidant activities of gel filtration fractions of kafirin Alcalase 5-10 kDa hydrolysate prepared at 0.4 Au/g and hydrolyzed for 4 hours, with FIG. 19A showing total phenolic content (mg GAE/g)
Figure 19B:
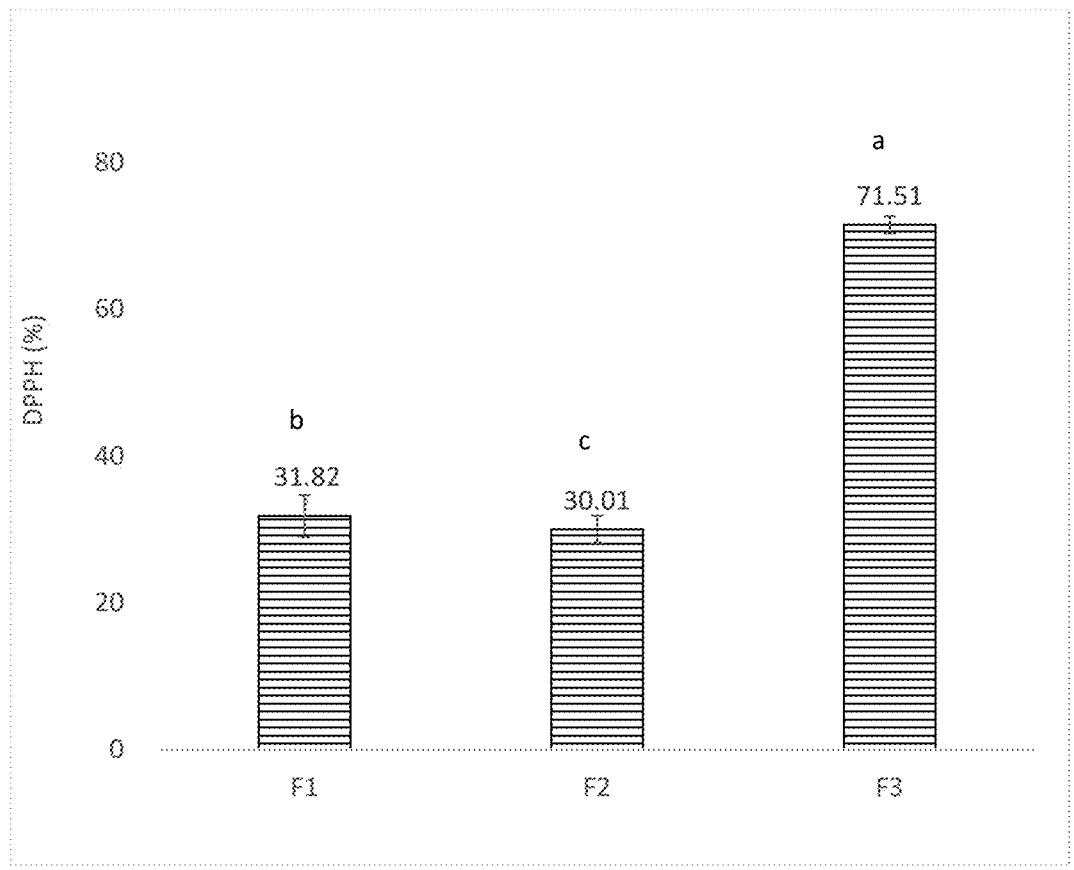
Figure 19C:
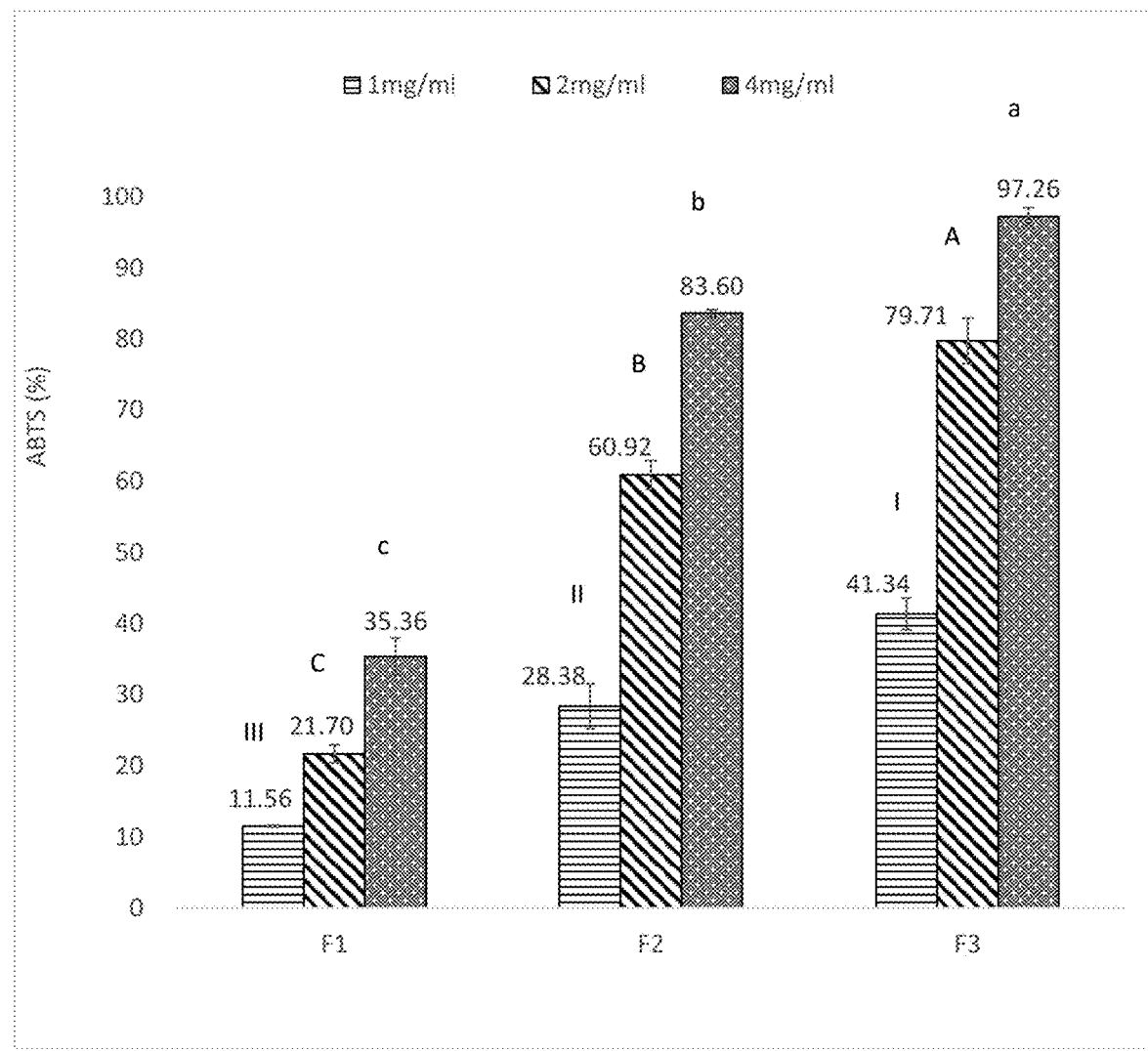
Figure 19D:
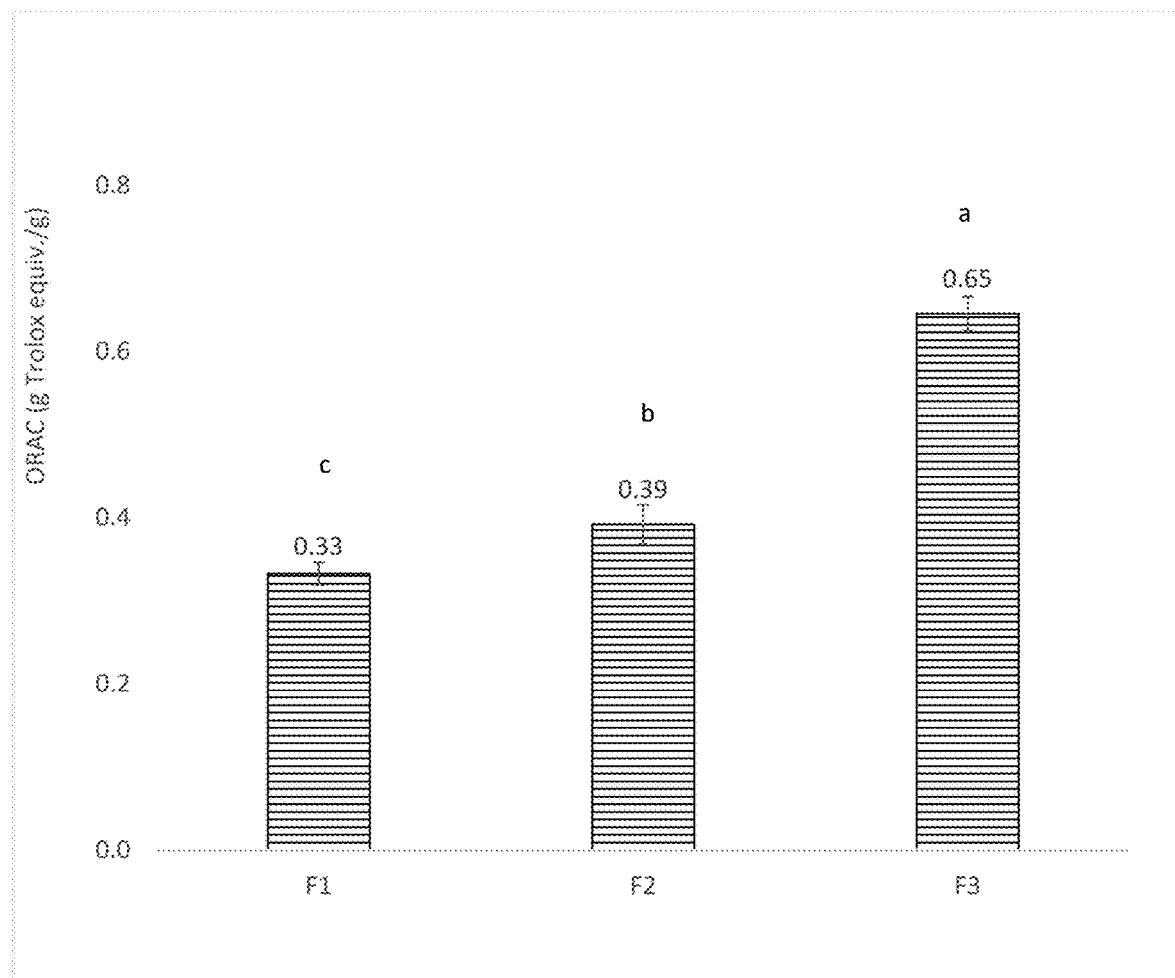

Purification and Identification of Antioxidative Peptides from Kafirin Alcalase 5-10 kDa Hydrolysates Gel Filtration of Kafirin Alcalase 5-10 kDa Hydrolysates Kafirin Alcalase 5-10 kDa fraction exhibited relatively higher antioxidant activity from previous experiments was further fractionated on a Sephadex-G25 gel filtration column (FIG. 18). The elution profile was divided into three fractions (F1-F3), and each fraction was collected and freeze-dried for analysis of total phenolic content and antioxidant activities (FIGS. 19A-19D).

Overall, the smaller sized fraction F3 manifested significantly (P<0.05) higher values in TPC, DPPH %, ABTS %, and ORAC than the other two fractions. F3 also possessed an enhanced antioxidant activity as well as TPC than the hydrolysate mixture without separation by gel filtration. Thus, gel filtration provided an effective tool to fractionate and isolate the most promising portions of peptides within the hydrolysate mixture.

Identification of Representative Peptide Sequences from Gel Filtration

The antioxidant activity of protein hydrolysates was dependent upon the characteristic amino acid sequences of the peptides derived, which was dictated by the protease specificity.

In order to identify the peptide profile present in the fraction of hydrolysates with potent antioxidant activity, F3 from gel filtration was further isolated and analyzed by RP-HPLC followed by MALDI-TOF/TOF MS analysis. After digestion with trypsin, several peaks appeared and represented the major counterparts of peptides present in the sample. Peaks at 1.6-, 3.6-, 35.0-, and 36.0-minutes possessing area percentages of 30.62%, 11.03%, 2.34% and 4.15% were collected and analyzed, separately. After fitting the spectrum to protein patterns of beta kafirin protein, a total of 26 peptides sequences were identified for each peak (Table 4). Three major peptide fragments were detected at m/z 617, m/z 637, and m/z 659.

Conclusions

Alcalase is an effective enzyme to produce antioxidant peptides with a relatively high protein recovery, increased total phenolic content, and enhanced antioxidative activities. The optimal reaction conditions of hydrolyzing kafirin with Alcalase was determined to be protein content of 4%, enzyme-to-substrate ratio of 0.4 Au/g, and hydrolysis time for 4 hours. By using membrane ultrafiltration, the kafirin

TABLE 4

Representative antioxidant peptides in kafirin Alcalase hydrolysates.

| Peak | 1.6 min | 3.6 min | 35.0 min | 36.0 min |
|---|---|---|---|---|
| Area % | 30.62% | 11.03% | 2.34% | 4.15% |
| Coverage % | 36.50% | 82.80% | 54.70% | 27.10% |
| | KMVIV (SEQ ID NO: 30) | QWQQ (SEQ ID NO: 3) | QQWQ (SEQ ID NO: 2) | KMVIV (SEQ ID NO: 30) |
| | LAVCLA (SEQ ID NO: 31) | QQWQ (SEQ ID NO: 2) | QWQQ (SEQ ID NO: 3) | AVCLAL (SEQ ID NO: 32) |
| | AVCLAL (SEQ ID NO: 32) | GVVQSV (SEQ ID NO: 36) | GVVQSV (SEQ ID NO: 36) | LAVCLA (SEQ ID NO: 31) |
| | QQWQ (SEQ ID NO: 2) | | QLQGVA (SEQ ID NO: 37) | QQWQ (SEQ ID NO: 2) |
| | QWQQ (SEQ ID NO: 3) | | VQQLQ (SEQ ID NO: 38) | QWQQ (SEQ ID NO: 3) |
| | RQQCC (SEQ ID NO: 33) | | VAQVAQ (SEQ ID NO: 39) | |
| | MCGWQ (SEQ ID NO: 34) | | RQQCC (SEQ ID NO: 33) | |
| | CATSAAI (SEQ ID NO: 35) | | MCGWVVQ (SEQ ID NO: 40) | |
| | | | CATSAAI (SEQ ID NO: 35) | |
| | | | DMQSR (SEQ ID NO: 41) | |

Alcalase is a serine endopeptidase with broad specificity but a preference for large, uncharged amino acid side-chain groups. It was found that, all four peaks from HPLC contained peptide sequences of QQWQ (SEQ ID NO: 2) and QWQQ (SEQ ID NO: 3), which could be critical peptide sequences responsible for the antioxidant activity of kafirin Alcalase hydrolysate. Valine (Val, V), leucine (Leu, L) and isoleucine (Ile, I) are symbolic hydrophobic amino acids, which were found to be present in almost all of the identified peptide sequences. This might be due to the cleavage nature of Alcalase that released more hydrophobic amino acids during the unfolding of kafirin protein.

The presence of these hydrophobic amino acids increased the solubility of their compositional peptides in lipid phase, thus, enhanced their accessibility to the hydrophobic lipid and/or oil targets. Besides, cysteine (Cys, C) and methionine (Met, M) are typical nucleophilic sulfur-containing amino acids that are widely accepted as antioxidant amino acids or important constituent amino acids in antioxidant peptide sequences despite some prooxidant properties under some circumstances, which were found to be present in 10 and 5 of the identified peptides, respectively. Tryptophan (Trp, W) is an aromatic amino acid that was also reported to be an important antioxidant amino acid due to the hydrogen donating ability of the aromatic ring. 10 of the identified peptides were found to contain Try at terminals or in sequences.

Alcalase hydrolysate was fractionated and the antioxidant activities associated with different $M_w$ ranges were evaluated through several different assays. Medium-sized fraction of hydrolysate (5-10 kDa) was found to possess the highest total phenolic content, DPPH radical scavenging activity, ABTS radical scavenging activity, reducing power, and metal chelating capacity. In two different model systems, the selected fraction of hydrolysate unveiled excellent inhibition effect against oil and/or lipid peroxidation. The hydrolysate was further fractionated by gel filtration chromatography and smaller-sized fraction (F3) showed a significantly stronger antioxidant activity.

By using RP-HPLC followed with MALDI-TOF/TOF MS analysis, 26 representative peptides were identified for sequences, meantime, QWQQ (SEQ ID NO: 3) and QQWQ (SEQ ID NO: 2) were found to be present in all major peaks from HPLC. In addition, the cleavage of peptides by Alcalase yielded significant amount of hydrophobic amino acids, which accounted for its admirable antioxidative activities especially towards hydrophobic targets.

With relatively high antioxidant activity and total protein recovery, the novel kafirin hydrolysates obtained with Alcalase is attractive to be considered as alternatives to synthetic antioxidants in various food and feed products as functional ingredients to deliver multiple functionalities besides its

Example III

Reaction Optimization, Antioxidant Activity Characterization, and Peptides Identification of Sorghum Kafirin Hydrolysates Prepared with Papain Abstract Papain was used to hydrolyze sorghum kafirin in producing hydrolysates and peptides with antioxidant capacity. At combined treatment of enzyme-to-substrate ratio and hydrolysis time, optimal reaction parameters (substrate content at 4%, enzyme-to-substrate ratio at 360 kU/g, and hydrolysis time of 4 hours) were determined through assessing total protein recovery, degree of hydrolysis, total phenolic content, and DPPH radical scavenging activity. Several other assays reflecting different antioxidation mechanisms were also employed to assess the antioxidant capacity of kafirin hydrolysates. After fractionation by ultrafiltration, small-sized hydrolysate (1-3 kDa) had stronger antioxidant activities as well as good yield; therefore, it was subjected for assessment in oil-in-water emulsion and ground pork model system for evaluation of its lipid and oil inhibition effects. The incorporation at 100 mg/mL oil resulted in an inhibition of primary and secondary oxidation products by 43.04% and 66.91%, respectively, without hurting emulsion turbidity or stability. An average of 32.12% inhibition effect towards lipid peroxidation was also detected when incorporated at 1.0 mg/g meat. The selected fraction of hydrolysate was further fractionated by gel filtration, and the most potent fraction (F3) was analyzed by HPLC followed with MALDI-TOF/TOF MS. Peptides LRQQ (SEQ ID NO: 4), QLQGV (SEQ ID NO: 5), and WQPN (SEQ ID NO: 6) were found to appear most frequently within the identified sequences, which might be related to the antioxidant activity of kafirin Papain hydrolysate. An extraordinary popularity of glutamine among identified peptides indicated that it could be an important counterpart accounting for the antioxidative potentials.

Introduction

In biological systems, imbalance between oxidants and antioxidants can cause damage to biological structures such as DNA mutation, membrane phospholipids oxidation, protein damages that could eventually lead to diseases. In food industry, oxidation of lipids and fat in food products causes undesirable quality deterioration such as development of discoloration, off-flavor, and rancid odors, which ultimately reduces the shelf life and decreases the nutritional quality and safety of foods. Antioxidants are a group of substances that can delay or inhibit the oxidation process at low concentrations, which has been commonly used in food industry as additives or functional ingredients to retard the oxidative spoilage of food products and maintain their shelf-stability and/or quality attributes. The antioxidant is a growing market that is projected to reach $3.1 billion in 2020. Synthetic antioxidants such as BHA and BHT was long being used as they are cheap and effective, but in recent years, their use has been limited or prohibited due to the potential toxicity, carcinogenic potentials, and other safety concerns over pathological conditions. Driven by market preference for safe and natural antioxidants, the peptide antioxidants have attracted rising interests. Some literatures have reported the excellent efficacy and multifunctionalities of antioxidants derived from cereal proteins such as those obtained from wheat, rice, and corn. These studies built the foundation of transforming sorghum protein into peptide antioxidants as potential alternatives to synthetic antioxidants. Compared to synthetic antioxidants, peptide antioxidants are considered safe even at high concentrations. They are also able to provide essential amino acid profiles, nutritional values, potential health benefits, and various functional properties such as gelling, emulsifying, foaming, water and/or oil binding capacity.

United States is now leading in global sorghum production and distribution, whereas sorghum is mainly used for animal feed or a starch source for production of bioethanol. Since there is an increasing trend of transforming bioresources into value-added products, the by-products (e.g., sorghum DDGS) of sorghum bioethanol industry, which was often discarded or underutilized, could possibly be modified into novel products for various industrial applications. Producing antioxidative hydrolysates and peptides from these protein-rich by-products or co-products by enzymatic hydrolysis provides a feasible approach for this value-adding conversion.

Proteins are typically large matrix with complex tertiary structures. The antioxidant activities of proteins are limited because functional groups and structural domains associated with antioxidative activities of peptides sequences are buried inside the hydrophobic core and are inaccessible to pro-oxidants. Enzymatic hydrolysis is commonly used to prepare hydrolysates and peptides with improved functionality and enhanced bioactivities, hence, are favorable than intact proteins in a lot of industrial applications. Many studies have reported that Papain was a promising enzyme to obtain antioxidative hydrolysates and peptides from various protein origins including wheat gluten, corn gluten meal, zein, and so on. Results of preliminary experiments also indicated that Papain was an efficient enzyme to release antioxidative peptide sequences from sorghum kafirin with a good yield of protein recovery. However, to the best of our knowledge, no report was yet found about the fractionation and characterization of antioxidative hydrolysates of sorghum protein hydrolyzed by Papain.

The objectives of this study were to: 1) optimize the reaction variables (hydrolysis time, enzyme-to-substrate ratio) of kafirin hydrolysis using Papain in production of antioxidative hydrolysates; 2) evaluate the antioxidative profile of purified peptide antioxidants by comprehensive in vitro assays as well as the antioxidant performances in emulsion and meat model systems; and 3) further purify the antioxidant peptides and identify the critical sequences in the most potent fraction of hydrolysates.

Materials and Methods

The materials and methods used for the study in this chapter were similar to those described in Examples I and II, thus, will not be repeated.

Results and Discussion

Reaction Optimization of Kafirin Enzymatic Hydrolysis

Enzyme (e.g., type of enzyme, enzyme amount), substrate (e.g., type of protein, protein content), and hydrolysis conditions (e.g., hydrolysis time) altogether enforced an integrated impact on the end product of hydrolysate including its yield as well as the antioxidant activity. In order to identify the optimal reaction conditions in of kafirin hydrolysis with Papain for production of antioxidant peptides, a factorial designed experiment using combined treatment of enzyme-to-substrate ratio (90, 180, 360, and 540 kU/g) and hydrolysis times (varied from 0.5 hour to 6 hours) was conducted. The recovery rate of total soluble hydrolysates released from intact protein, degree of hydrolysis (DH), total phenolic content (TPC), and antioxidant activity measured by DPPH radical scavenging activity (DPPH %) were employed as critical indicators and the results were summarized in FIGS. 20A-20D.

Figure 20A:
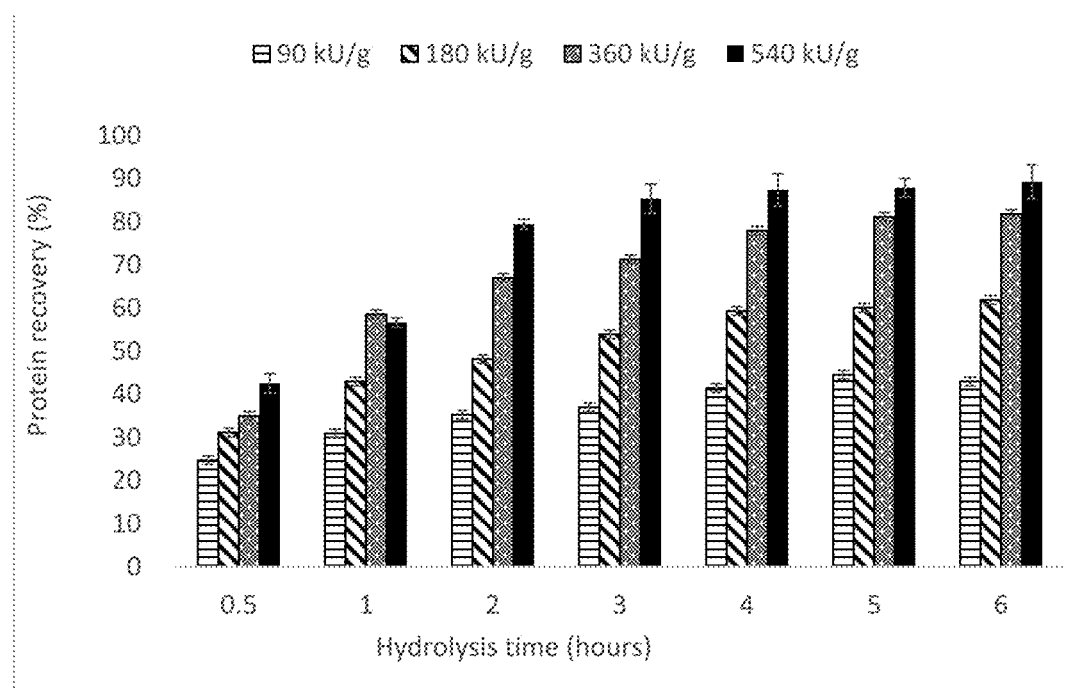
FIGS. 20A, 20B, 20C, and 20D are graphs showing reaction optimization and antioxidant activities of kafirin Papain hydrolysates prepared at combinations of different hydrolysis time and three enzyme-to-substrate ratios (90, 180, 360, and 540 kU/g), with FIG. 20A showing total protein recovery (%)
Figure 20B:
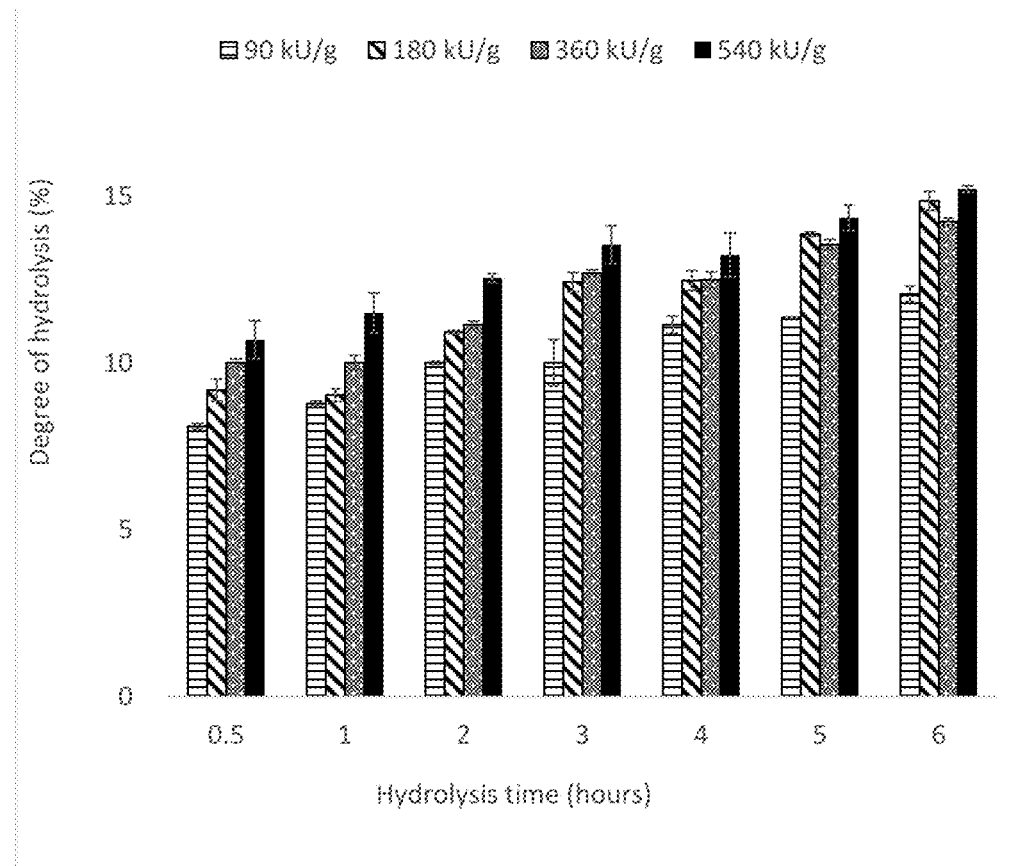
Figure 20C:
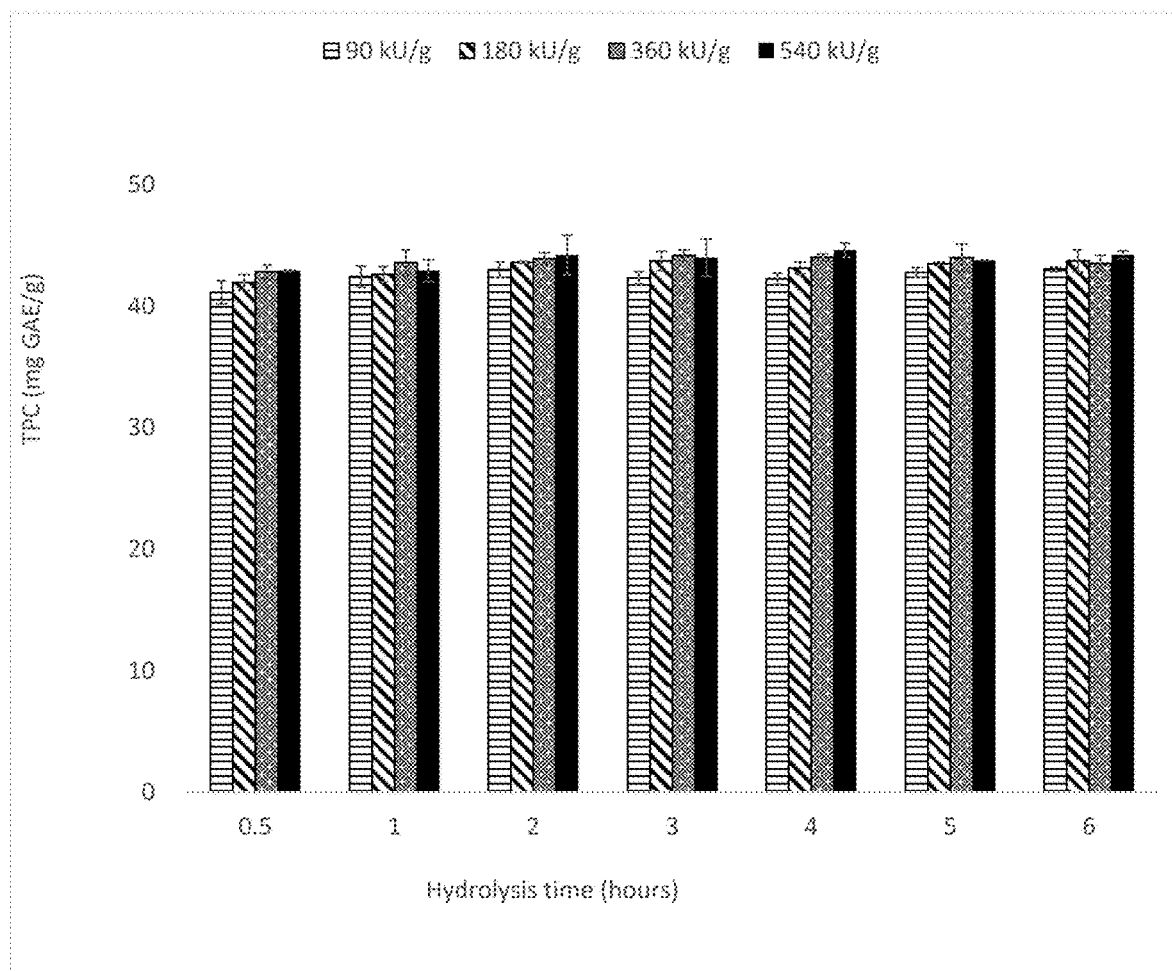

In FIG. 20A, with a prolonged hydrolysis time especially from 0.5 to 4 hours, a huge leap in total protein recovery was observed, despite the specific point of time to reach the reaction plateau varied for different enzyme-to-substrate ratio treatments. At lower levels of enzyme dosage (90 and 180 kU/g), the reactions were close to equilibrium at around 2 hours of hydrolysis and the total protein recovery rates did not increase obviously afterwards with extended hydrolysis time. When elevating the enzyme-to-substrate ratio from 90 to 540 kU/g, total recovery rates greatly increased especially for the hydrolysates obtained with longer time of hydrolysis. The hydrolysis occurred at higher levels of enzyme-to-substrate ratios (360 and 540 kU/g) displayed good recovery rates even with a shorter hydrolysis time, the recovery rates were ended close to 100% given sufficient hydrolysis. Yet, a noteworthy increase did not appear when changing the enzyme-to-substrate ratio from 360 to 540 kU/g. Similarly, in FIG. 20B, DH consistently increased with protracted hydrolysis time for all treatments until it reached steady at around 4 hours of hydrolysis. A remarkable increase in DH was not observed when increasing the enzyme amount from 90 to 540 kU/g. This data implied that in the initial stage of protein hydrolysis, reaction time applied to the system was the first limiting factor; meanwhile, the amount of enzyme applied to the hydrolysis system was the limiting factor in the latter stage of protein hydrolysis.

Hydrolysis of kafirin leads to the structural changes of the intact proteins including the release of phenolic peptides and phenolic compounds, which significantly contributed to the total antioxidant capacity of hydrolysates. The total phenolic content (TPC) is a rough estimate of the quantity of these compounds, thus, was measured for all treatments of kafirin hydrolysates as shown FIG. 20C. All hydrolysates had a similar TPC value that was not impacted by the different treatment of hydrolysis time or enzyme-to-substrate ratios. The TPC was between 41.16 and 44.63 mg GAE/g, which was higher than that prepared with Alcalase or Neutrase.

Figure 20D:
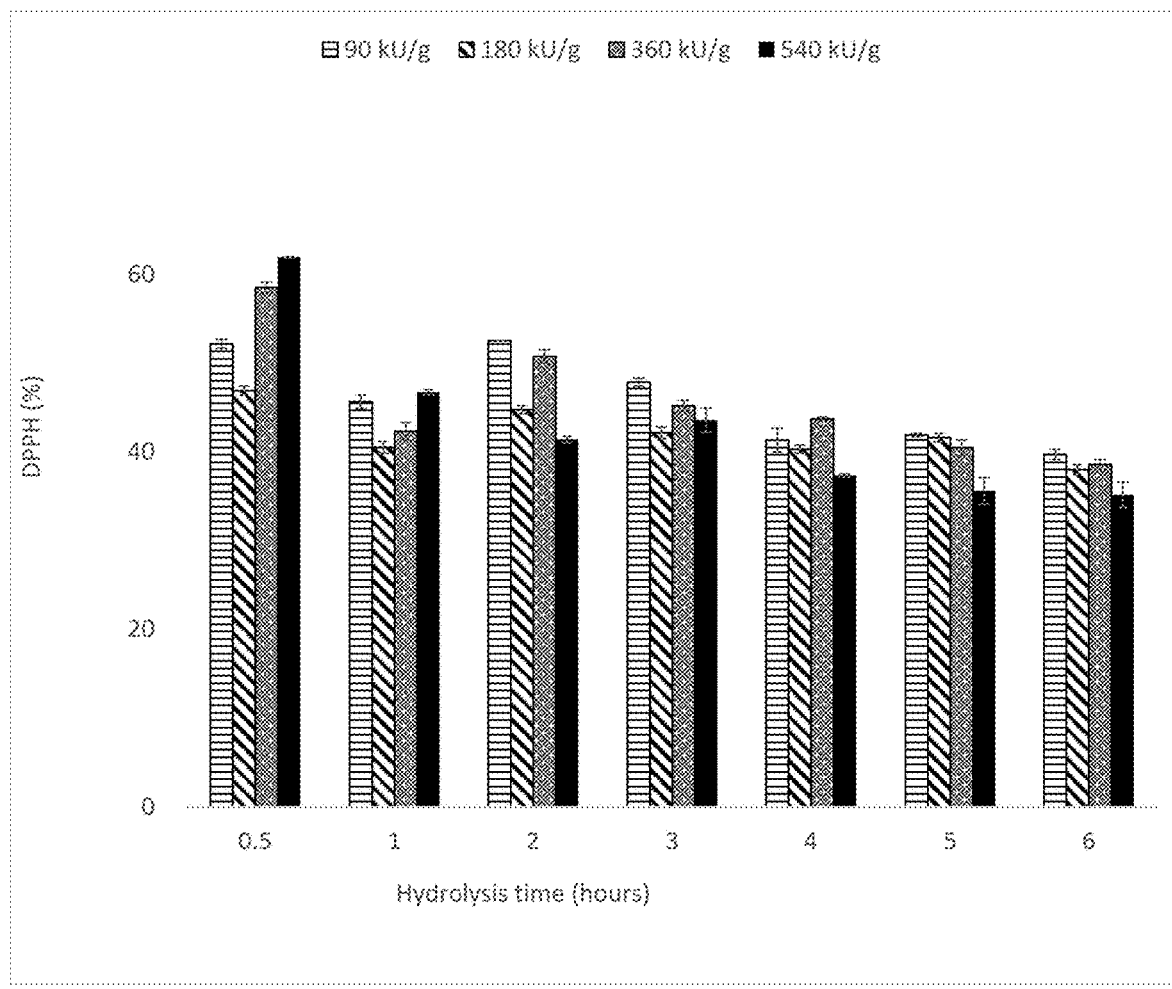

DPPH % is a simple and rapid assay that tests the ability of a compound to act as electron donors, which provide straightforward information antioxidant potentials of kafirin hydrolysates. As shown in FIG. 20D, kafirin Papain hydrolysates prepared with all treatments possessed DPPH scavenging capacities. The DPPH % values of hydrolysates prepared after 3 hours of hydrolysis were very much similar (35.21%-47.88% at 5 mg/mL), and no obvious relationship between DPPH % and hydrolysis time was observed. It worth attention to note that the abnormal high values of hydrolysates prepared with less than 2 hours were detected, which was largely due to the intrinsic activity of enzyme may have conquered the activity of hydrolysates therefore was not taken into consideration. This result revealed that, the kafirin Papain hydrolysates contained substrates that were electron donors, which were able to convert free radicals into more stable products and therefore terminate the radical chain reaction.

As a conclusion, extending hydrolysis time after 4 hours did not result in an improved total protein recovery. The additional amount of enzyme from 360 to 540 kU/g was unnecessary. Since an extensive hydrolysis may lead to the production of free amino acids or short-chained peptides that lost the essential structures accounting for antioxidative capacity, a hydrolysis time longer than 4 hours was not suggested. Considering a good balance of protein recovery, antioxidant activity, and economic efficiency, 4% kafirin protein solution coupled with an enzyme-to-substrate ratio of 360 kU/g for 4 hours was determined to be the optimal reaction parameters for the hydrolysis of kafirin in production of antioxidant hydrolysate.

Ultrafiltration of Kafirin Papain Hydrolysates

It was widely reported that, the molecular mass is one of the most important determining the antioxidant activity of a peptide. Thus, it is necessary to characterize the molecular weight distribution of the antioxidative hydrolysates and study the antioxidant activity associated with each molecular weight range. The kafirin hydrolysate prepared with Papain at optimized conditions (protein content of 4%, enzyme-to-substrate ratio of 360 kU/g, and hydrolysis time of 4 hours) was sequentially ultrafiltrated in a stirred cell coupled with 10 k, 5 k, 3 k, and 1 kDa molecular weight cut-off membranes. Fractions with different molecular weight ranges were collected, lyophilized, and analyzed.

Figure 21:
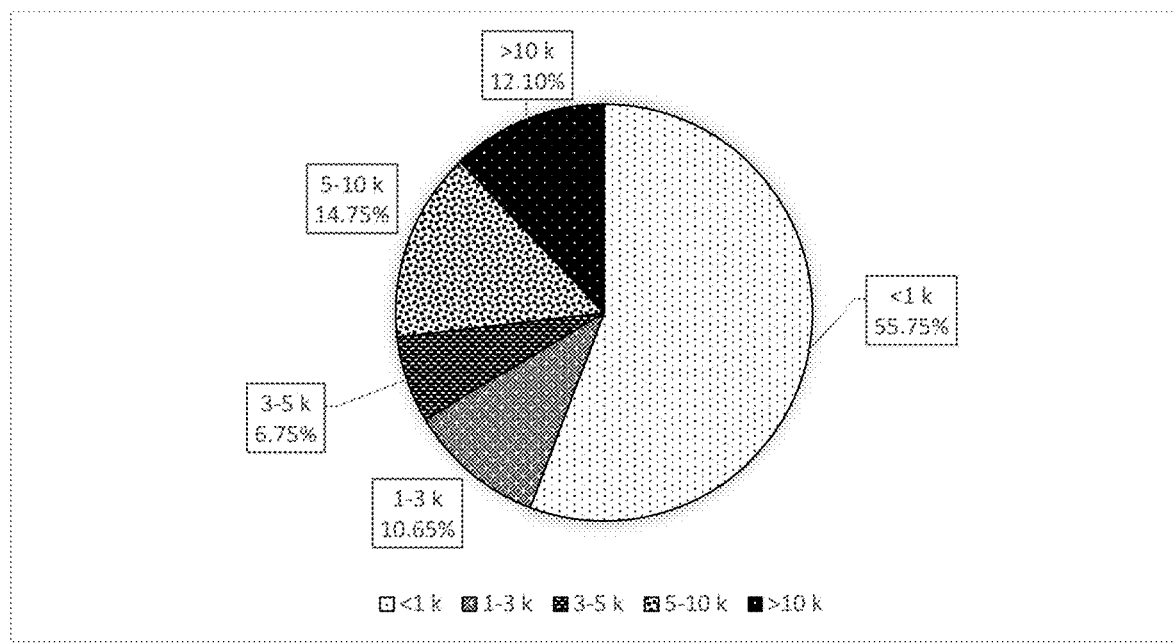
FIG. 21 is a pie chart showing distribution of ultrafiltrated fractions of kafirin Papain hydrolysate prepared at enzyme-to-substrate ratio of 360 kU/g and hydrolyzed for 4 hours followed with membrane filtration using 10 k, 5 k, 3 k, and 1 kDa membranes.

FIG. 21 shows the distribution of fractions of hydrolysates with different molecular weight ranges from ultrafiltration. As it can be seen, the <1 kDa fraction took up most of the hydrolysate (55.75%), the 5-10 kDa fraction was the second largest fraction (14.75%) followed with >10 (12.10%), 1-3 (10.65%), and 3-5 kDa (6.75%) fractions. Since percentage yield of protein hydrolysates was rarely reported, there were not adequate literatures for comparison.

Figure 22A:
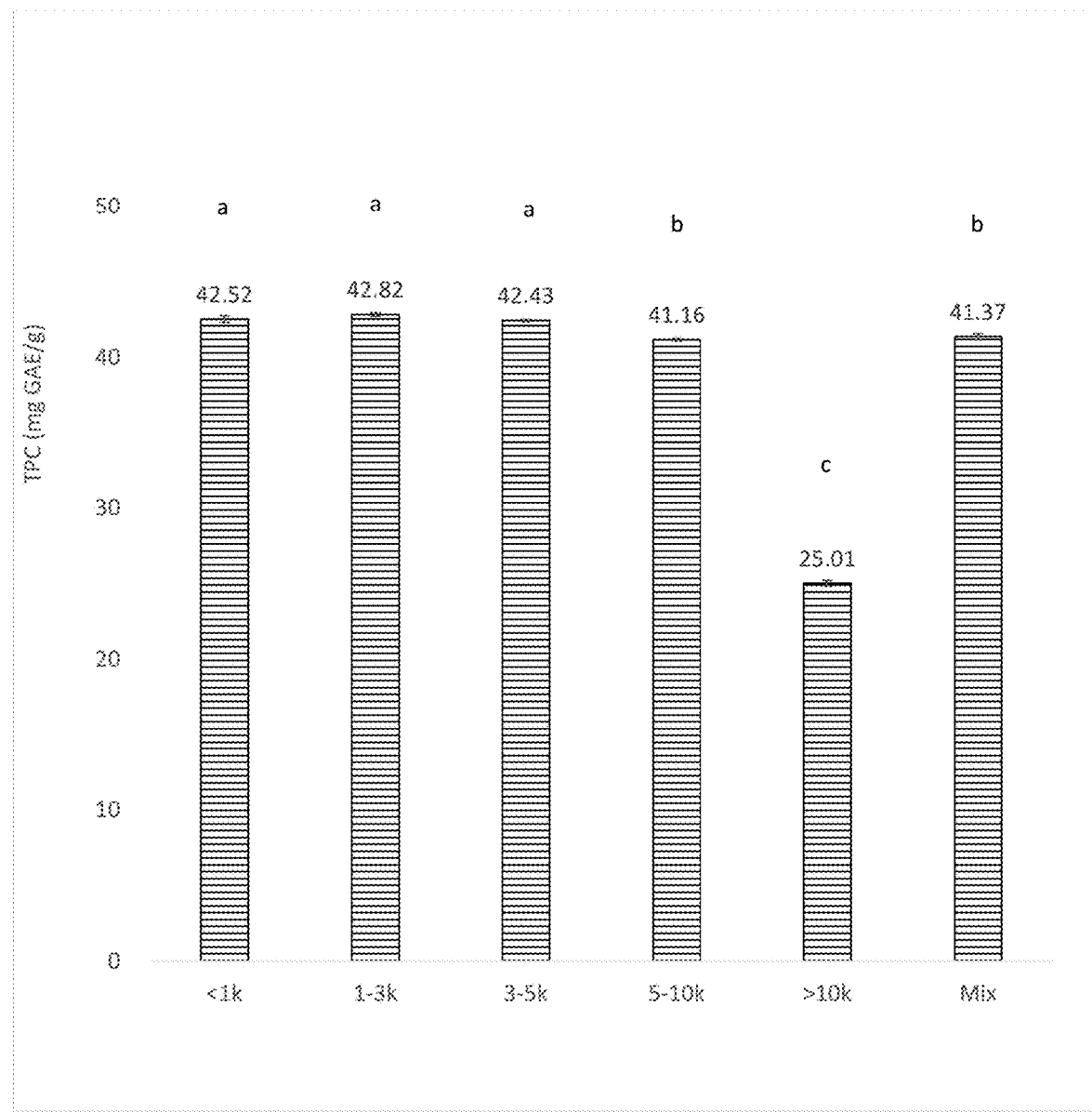
FIGS. 22A, 22B, 22C, 22D, 22E, and 22F are graphs showing total phenolic content and antioxidant activities of kafirin Papain hydrolysate ultrafiltrated fractions prepared at 360 kU/g and hydrolyzed for 4 hours followed with membrane filtration using 10 k, 5 k, 3 k, and 1 kDa membranes, with FIG. 22A showing Total phenolic content (mg GAE/g)

As shown in FIG. 22A, TPC was measured for the hydrolysate mixture and its ultrafiltrated fractions. It was found that, 3-5 kDa (43.48±0.07 mg GAE/g) fraction of hydrolysate possessed highest TPC followed with 1-3 kDa (42.82±0.12) and <1 kDa (42.51±0.22) fractions. Except for >10 kDa fraction (25.01±0.19 mg GAE/g), all the other ultrafiltrated fractions were found to have higher TPC than the hydrolysates without ultrafiltration (41.37±0.20 mg GAE/g).

Figure 22B:
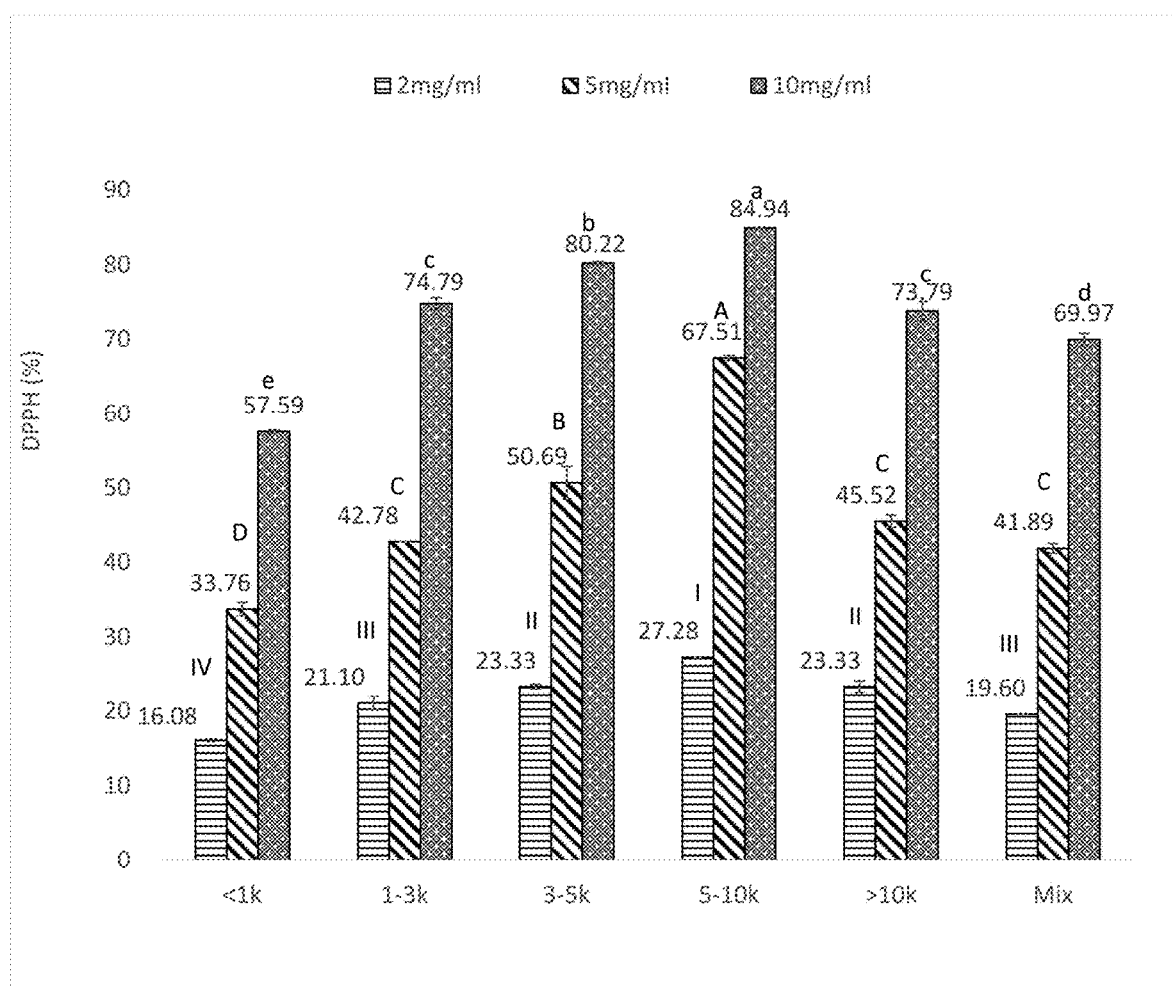

DPPH % assay was used to evaluate the antioxidant activity of ultrafiltrated fractions of hydrolysates regarding their ability in electron donating. In FIG. 22B, all fractions of hydrolysates showed abilities to quench DPPH radicals, the scavenging effects increased along with amplified sample concentrations, undoubtedly. Among all five ultrafiltrated fractions, medium-sized peptides, 5-10 kDa fraction exhibited strongest DPPH % (67.51±0.33% at 5 mg/ml) followed by 3-5 kDa (50.68±2.17% at 5 mg/ml) while the small-sized peptides<1 kDa (33.76±0.89% at 5 mg/ml) fraction had the lowest DPPH % value.

Figure 22C:
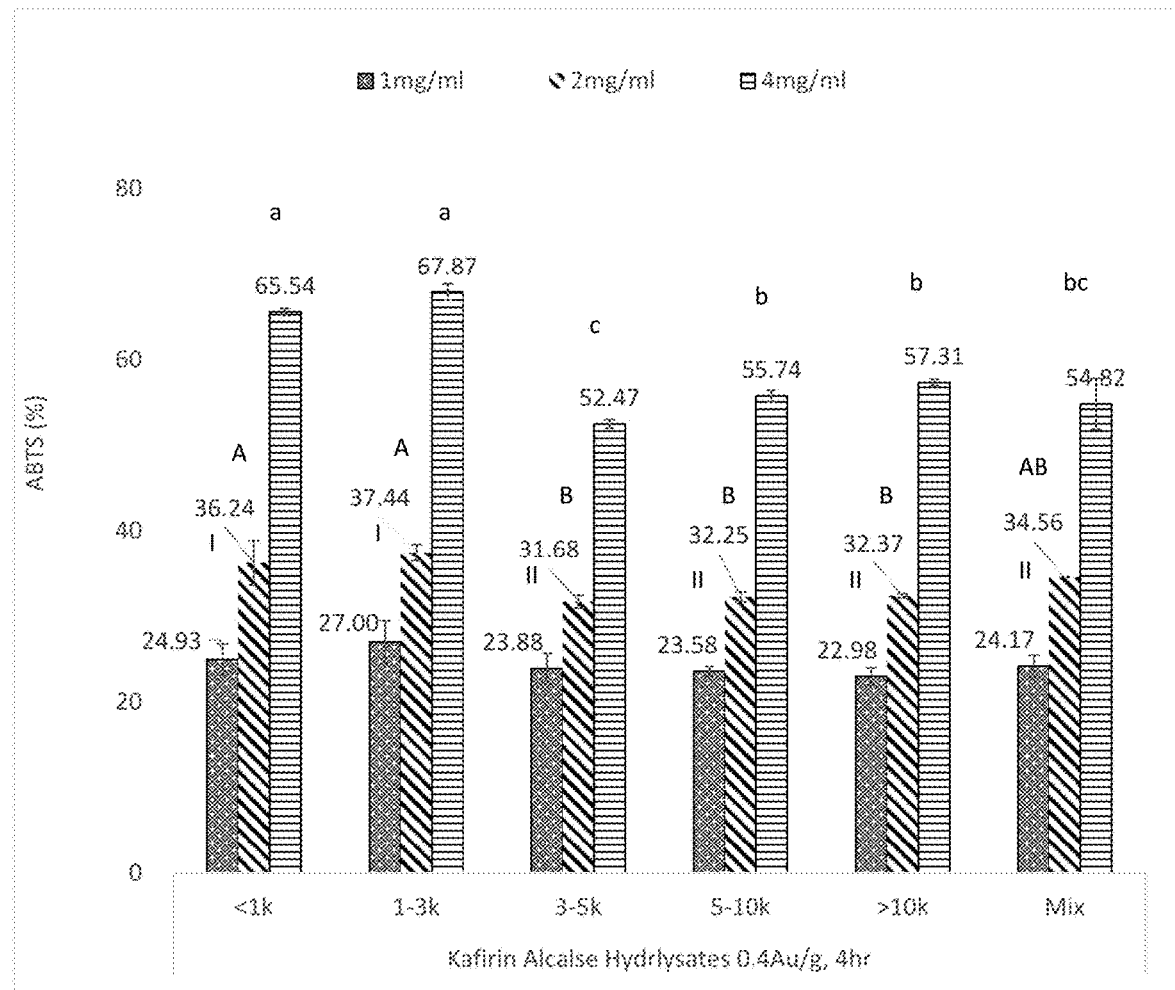
Figure 22D:
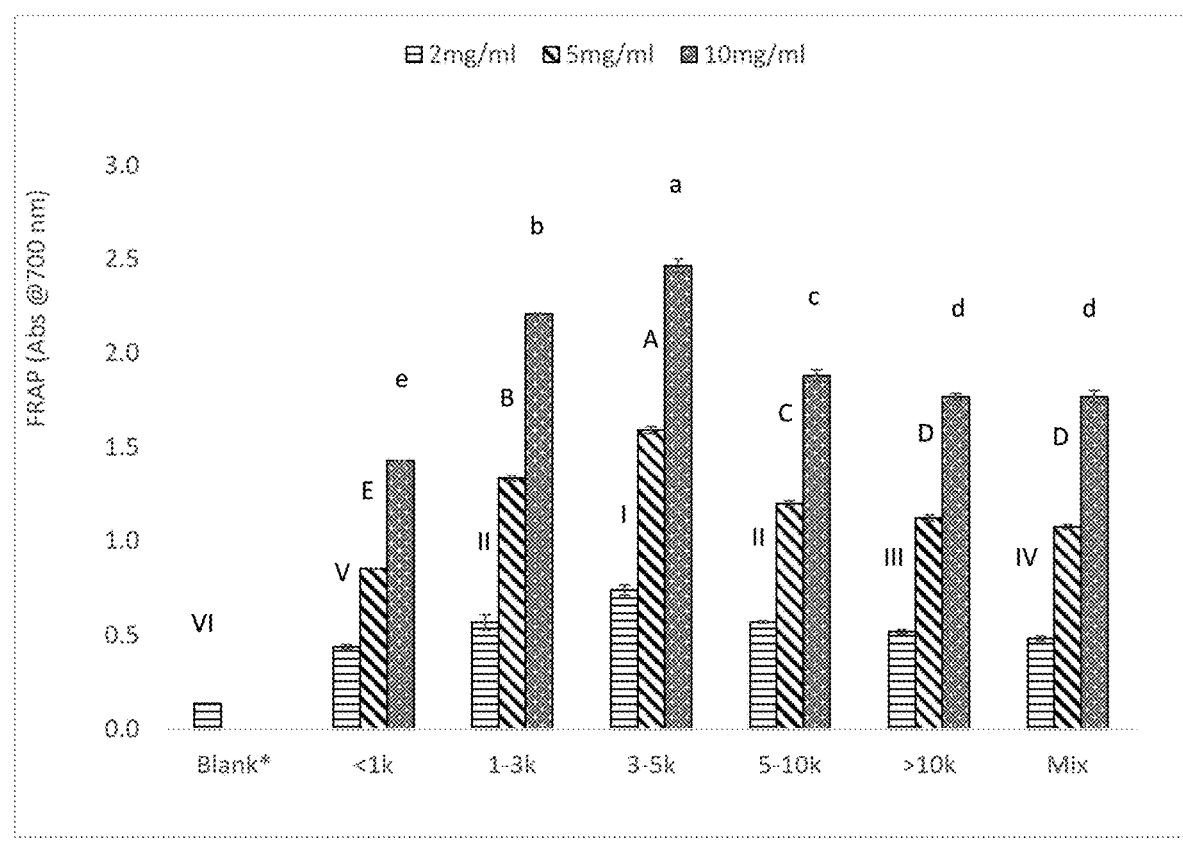

The medium-sized fraction of peptides 3-5 kDa also exhibited the strongest reducing power capacity reflected by the highest absorbance at 700 nm ($A_{700}$=1.59±0.037 at 5 mg/mL) monitored on a spectrophotometer (FIG. 22D). The increased absorbance of sample over a blank control implied the amount of ferrous iron reduced from ferric iron by the of antioxidant effects of hydrolysates. In addition, all fractions of kafirin hydrolysate possessed markedly higher absorbance values ($A_{700}$>1.00 at 5 mg/mL) than the blank control ($A_{700}$=0.136±0.048) may be attributed to the increased availability of hydrogen ions (protons and electrons) due to peptide cleavages.

Figure 22E:
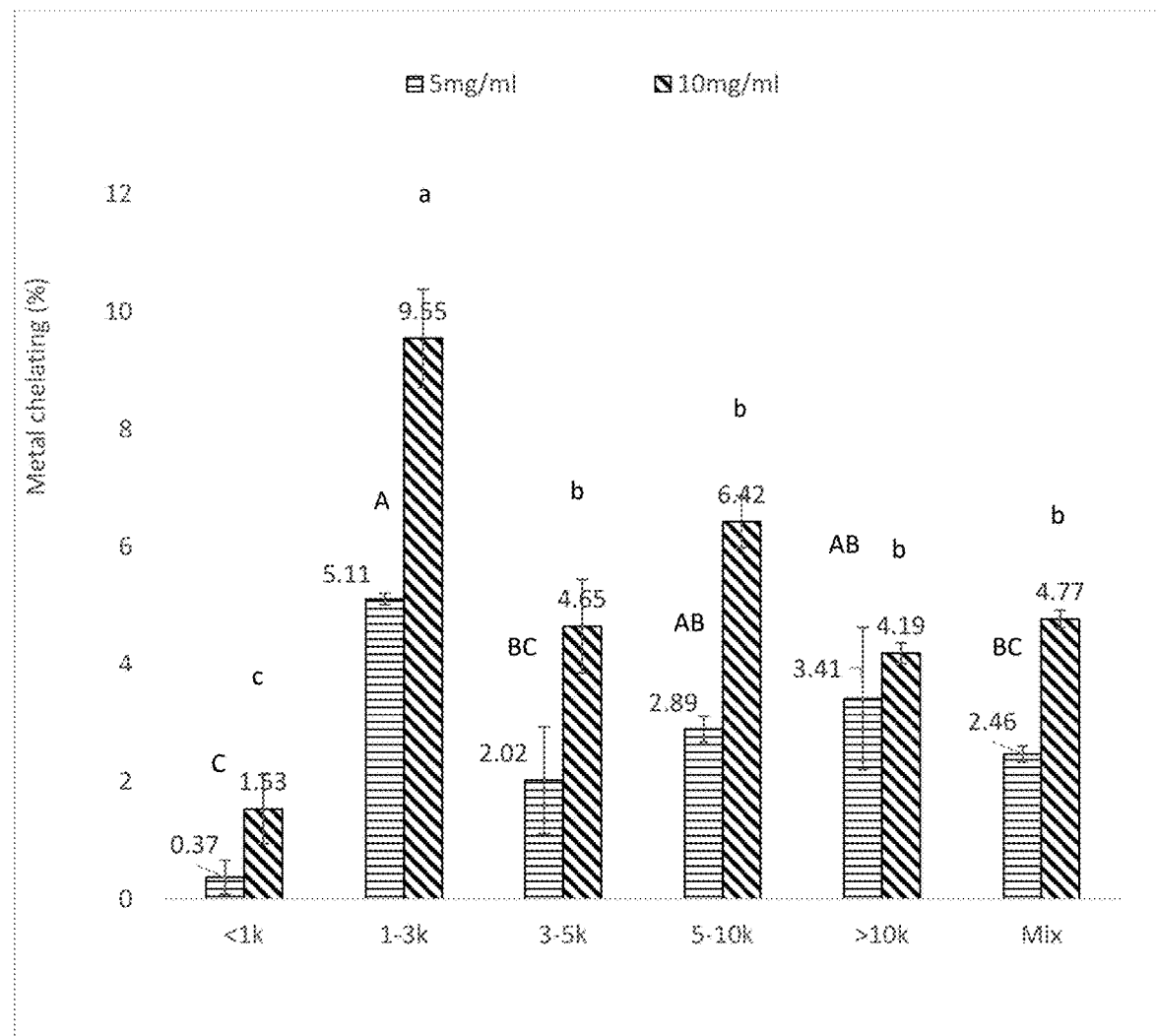
Figure 22F:
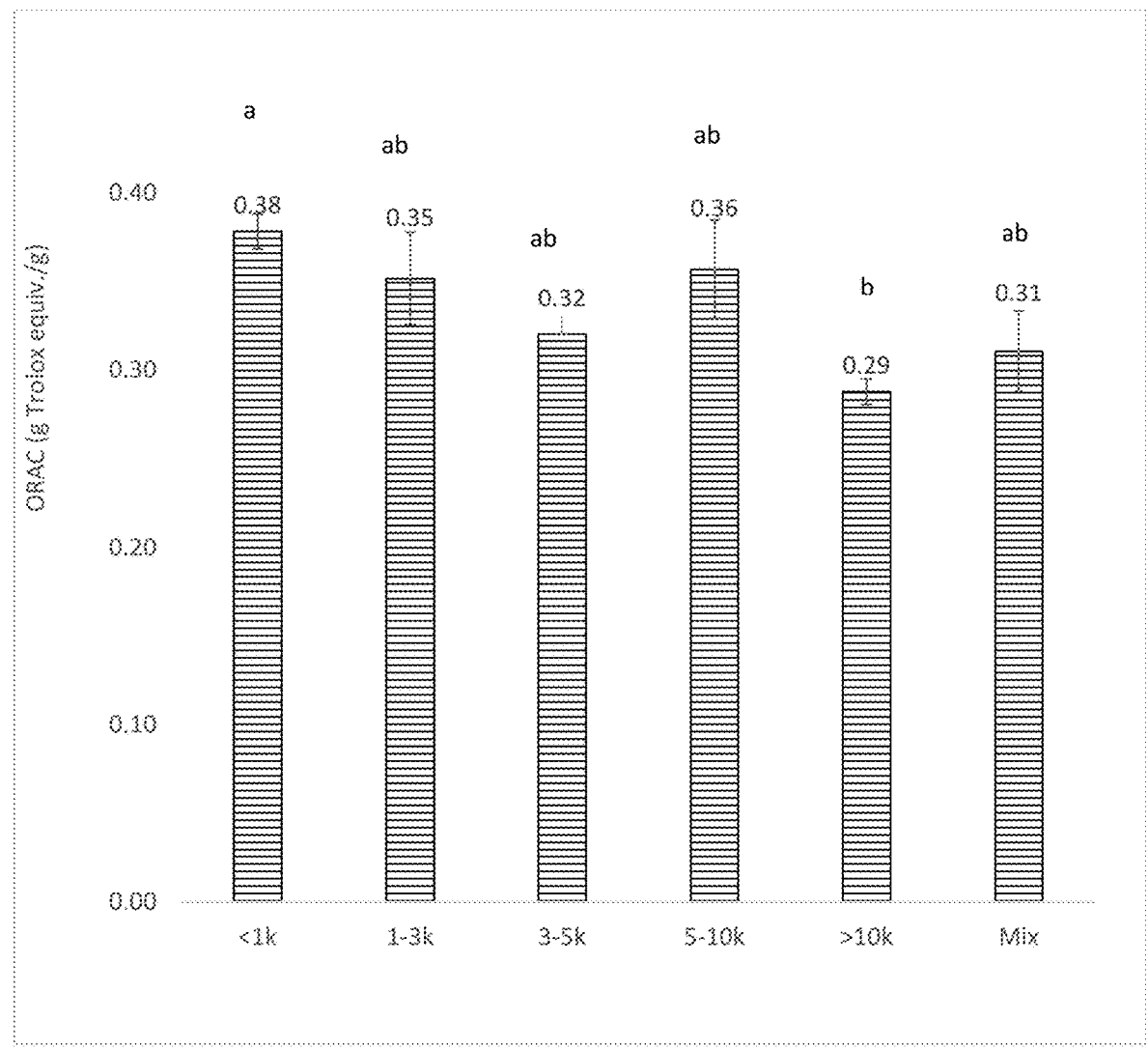

ABTS % assay provided the evaluation of antioxidant capacity in a different aspect, which was calculated by the percentage of ABTS radicals quenched by the antioxidants. As shown in FIG. 22C, small-sized peptide fractions, <1 kDa (36.24±1.82% at 2 mg/ml) and 1-3 kDa (37.44±2.46% at 2 mg/ml) yielded a higher ABTS % than the other larger-sized peptide fractions. The small-sized peptide fractions <1 kDa and 1-3 kDa also exhibited good to excellent activities in metal chelating capacity and ORAC assay as shown in shown in FIG. 22E and FIG. 22F, respectively.

Smaller-sized peptides are commonly preferred for better antioxidative activity in a lot of studies as they are believed to be more accessible and easily adsorbed to the oxidative agents compared to the larger peptides. Based on the combined data, 1-3 kDa fraction exhibiting promising antioxidant activities and acceptable yield was selected for further evaluation in model systems.

Inhibition of Lipid Oxidation in Model Systems

Oil-in-Water Emulsion System

Each in vitro chemical assay such as DPPH, ABTS, ORAC, reducing power, or metal chelating measured antioxidant activity represented by a single mechanism, which could not reflect the multiple mechanisms or the comprehensive outcome of peptide antioxidants. Thus, it is necessary to evaluate the peptides' protective action of oil/lipid oxidation in model food systems, which provides important information to processing strategies for the development of peptide antioxidants.

An oil-in-water emulsion model system was employed to examine the expected inhibition effect of antioxidant peptides against oil/lipid oxidation. 1-3 kDa fraction of kafirin Papain hydrolysates which showed relatively higher activities in chemical assays was incorporated at 50 mg and 100 mg per mL of oil to prepare emulsion samples. Tween-20 was added as a stabilizer to enhance the emulsion stability.

Figure 23A:
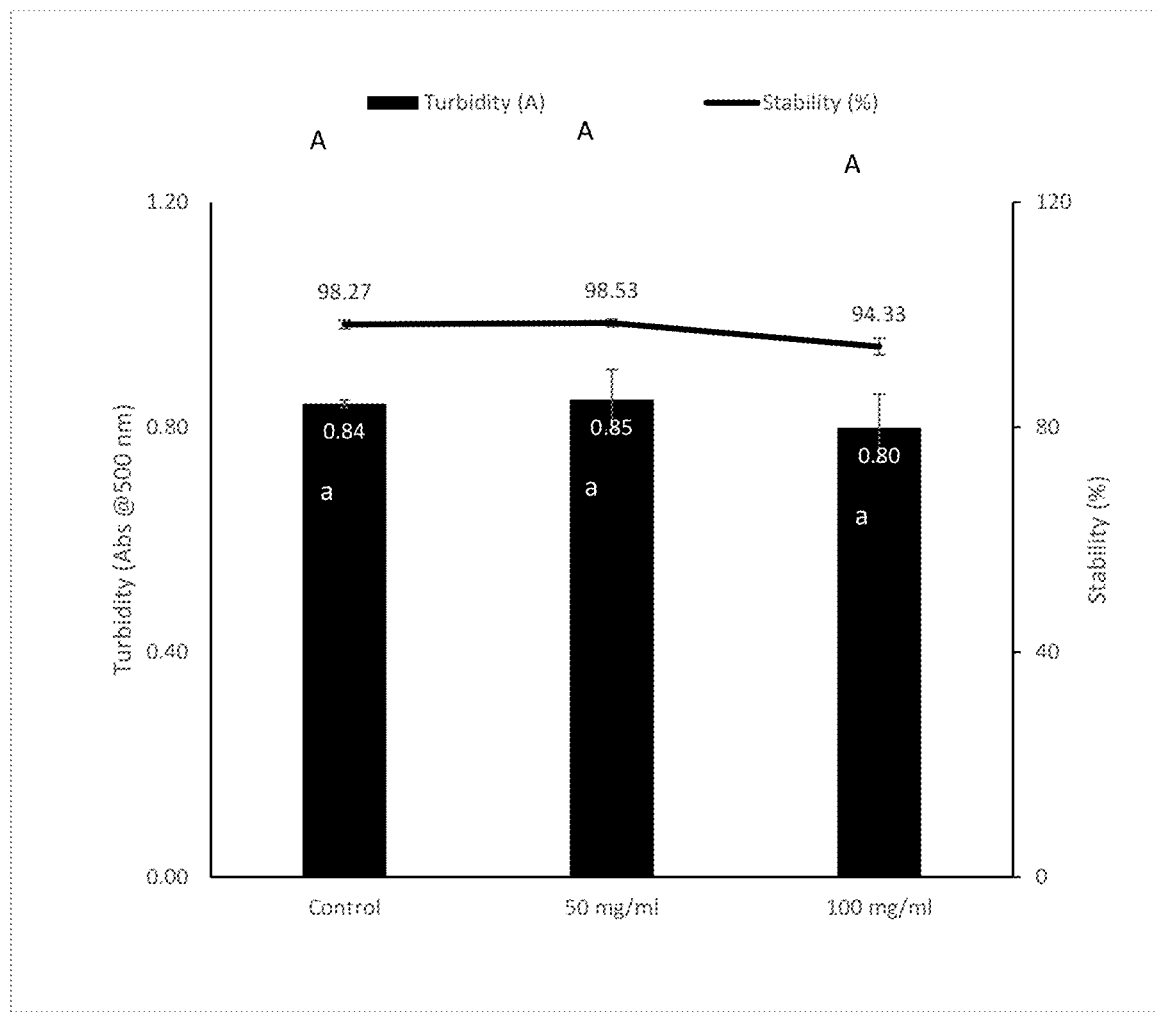
FIGS. 23A, 23B, and 23C are graphs showing inhibition effect of kafirin Papain 1-3 kDa hydrolysate prepared at 360 kU/g and hydrolyzed for 4 hours in an oil-in-water emulsion model system added with 50 and 100 mg/mL oil, with FIG. 23A showing Emulsion turbidity (Abs at 500 nm) and stability (%)

As shown in FIG. 23A, no significant difference in emulsion turbidity and emulsion stability (P<0.05) was observed for the emulsion sample incorporated with kafirin Papain hydrolysates. This indicated that the utilization of hydrolysates did not alter the texture properties of emulsions. High turbidity values ($A_{500}$>0.80) were observed among all emulsion samples, which symbolized that the oil was effectively dispersed in the aqueous solution and fine emulsions were achieved. All emulsions exhibited good stabilities (>94%) and stayed stable during a 14-day incubation period at 37° C.

Figure 23B:
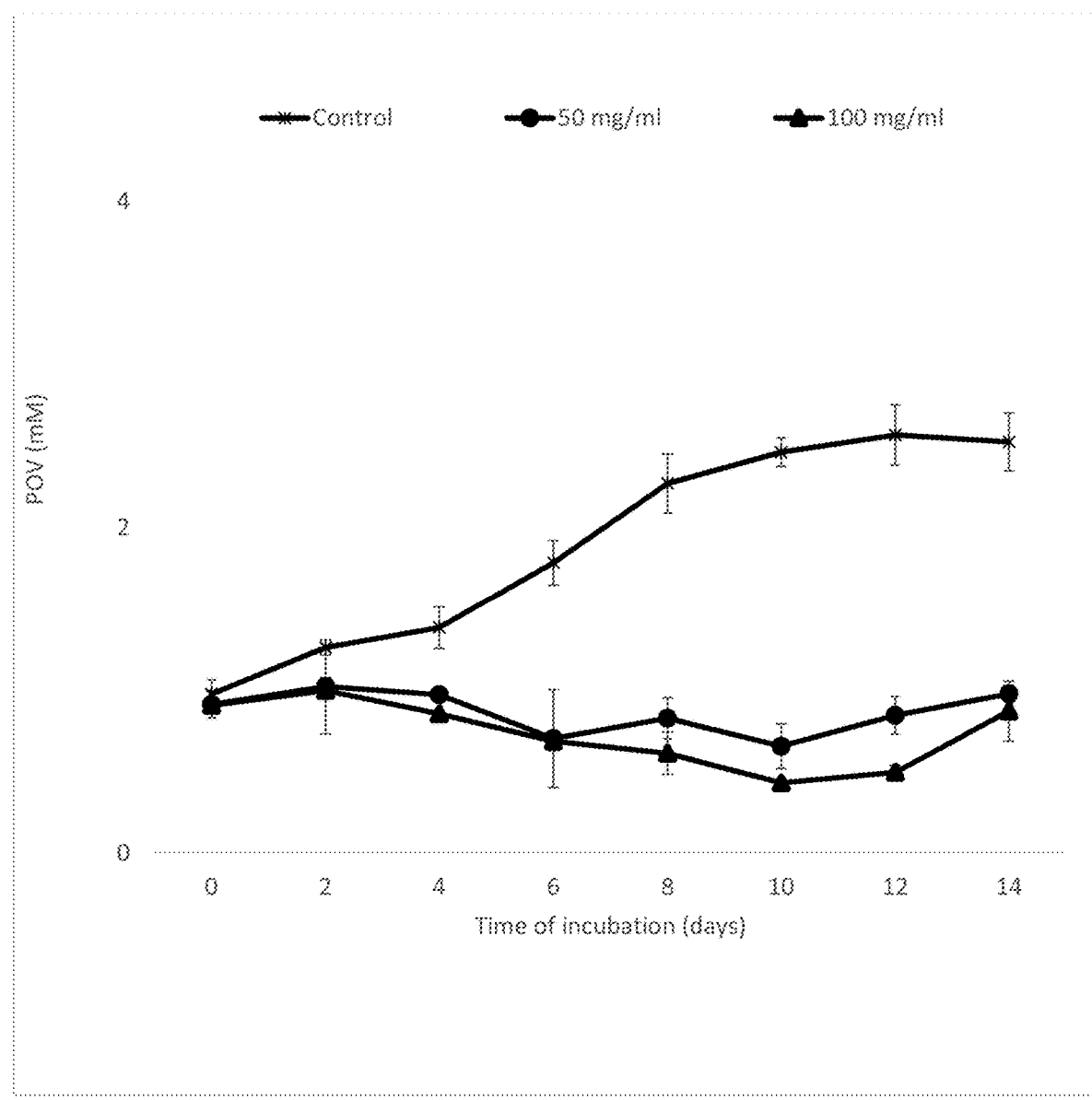
Figure 23C:
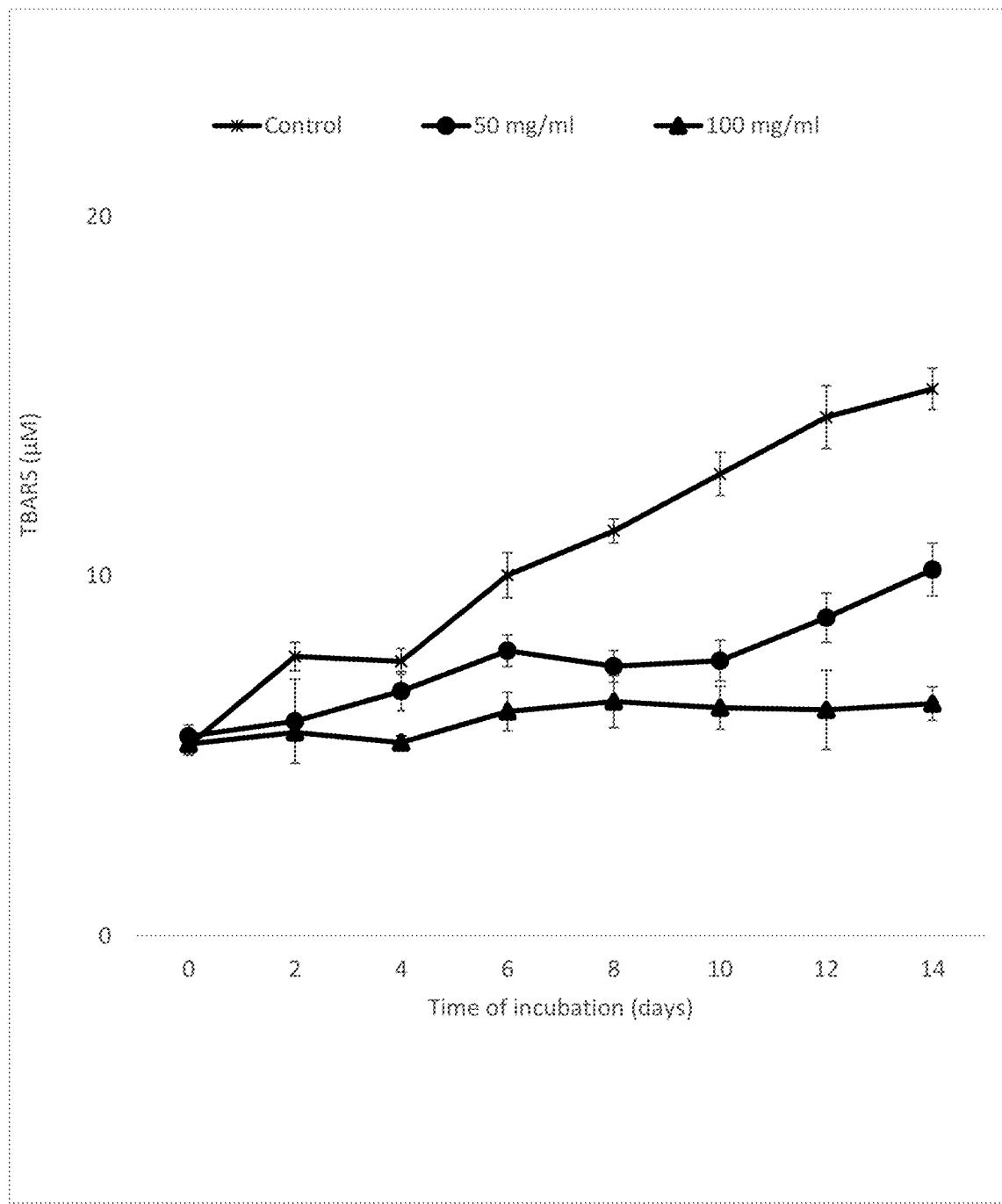

Besides, as shown in FIG. 23B and FIG. 23C, the oxidation activities of emulsion were effectively inhibited by the addition of antioxidant peptides. The concentration peroxide values (POV) was decreased by an average of 59.27±15.19% and 66.91±16.16% by hydrolysates at 50 mg/mL and 100 mg/mL, respectively. The inhibition rate slowly increased with an extended incubation time, and the maximal inhibition was achieved at day 10 with 73.36% and 82.49% for 50 mg/mL and 100 mg/mL, respectively. On day 10, the inhibition rate decreased to around 61.31% and 65.50%, which reflected a loss of efficacy of antioxidant peptides. The concentration of TBARS was also reduced by antioxidant peptides. It has a highest inhibition rate of 40.39% for 50 mg/mL and at day 10, and 56.44% for 100 mg/mL at day 12. The average inhibition was 28.63±10.7% and 43.04±12.29% for 50 mg/mL and 100 mg/mL, respectively.

It can be concluded that kafirin hydrolysate prepared with Papain effectively act as an antioxidant in protecting the emulsion from oxidation.

Ground Meat System

The oxidative damage to meat-based products results in problems like tissue damage, development of undesired color and odor, loss of nutrients, accumulation of toxic products, etc.

The oxidative stability of meat products mainly depends on the balance of antioxidants, oxidative agents, cholesterol, and haeme pigment. Lipid peroxidation is an oxidative chain reaction where lipid molecules were oxidized to the maximum possible extent to form lipid peroxides. It could be slow at the beginning but proceed rapidly once oxidative chain reaction was initiated. Lipid hydroperoxides, which are the primary products of lipid oxidation, have higher polarity than normal fatty acids, thus, they are able to disrupt the integral structure and function of the biological membranes and cause detrimental damages to the biological tissues. The application of antioxidant is considered a pragmatic choice in controlling the lipid oxidation problem of meat and meat products as it can retard the rate of oxidation and reduce the peroxyl radicals to the hydro-peroxide before it participates the radical chain. Antioxidants can further reduce protein oxidation as well as the interaction of lipid-derived carbonyls with proteins, preventing alteration of protein functionalities.

Figure 24:
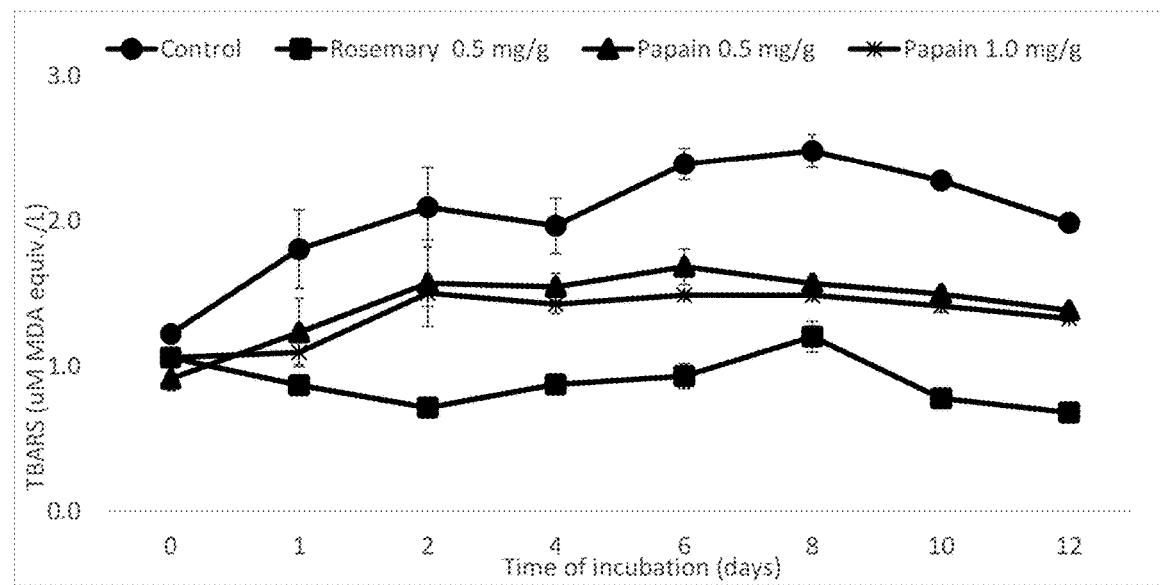
FIG. 24 is a graph showing inhibition effect shown as TBARS of kafirin Papain 1-3 kDa hydrolysate prepared at 360 kU/g and hydrolyzed for 4 hours in a ground meat model system added with 0.5 and 1 mg/g meat.

As shown in FIG. 24, it was observed that over 12 days incubation period, the kafirin Papain hydrolysates was able to inhibit the peroxidation as revealed by the reduced concentration of TBARS compared to blank control. A mean inhibition level was calculated to be 29.26±5.14% and 32.12±9.03% for 0.5 mg/g and 1.0 mg/g, respectively. The inhibition rate was slowly increased in early stage of incubation and reached maximum at day 8, where the inhibition was observed to be 30.76% and 40.03% for 0.5 mg/g and 1.0 mg/g, respectively.

The inhibition of lipid oxidation has been attributed to chelation of prooxidative metal ions, quenching singlet oxygen, scavenging free radicals, and termination of free radical chain reactions which was accomplished through specific amino acid residue side-chain groups or specific peptide structure. The oxidation inhibitive potentials of kafirin hydrolysates revealed in this study was higher than that of soy protein hydrolysates previously reported other studies. However, the TBARS inhibition percentage was lower than that of commercial rosemary extract. More efforts need to be paid to fractionate and purify the hydrolysates to determine the active components responsible for the antioxidant activities.

Figure 25:
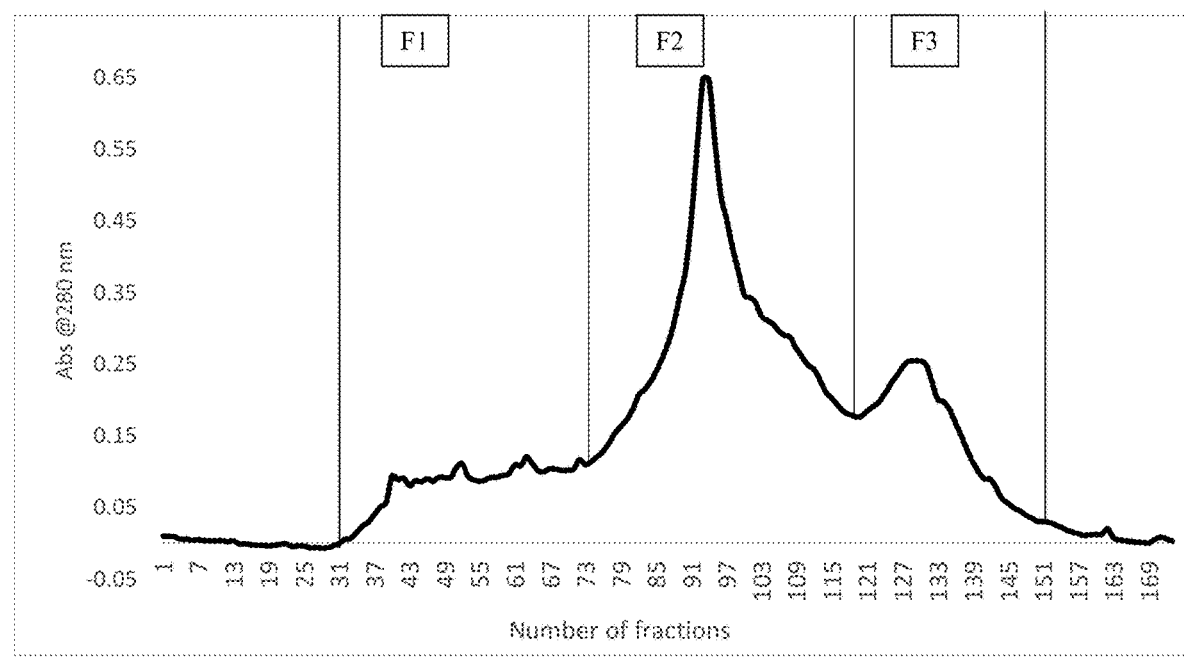
FIG. 25 is a graph showing gel filtration chromatogram of kafirin Papain 1-3 kDa hydrolysate prepared at enzyme-to-substrate ratio of 360 kU/g and hydrolyzed for 4 hours in a Sephadex G-25 column (26 mm×850 mm)
Figure 26A:
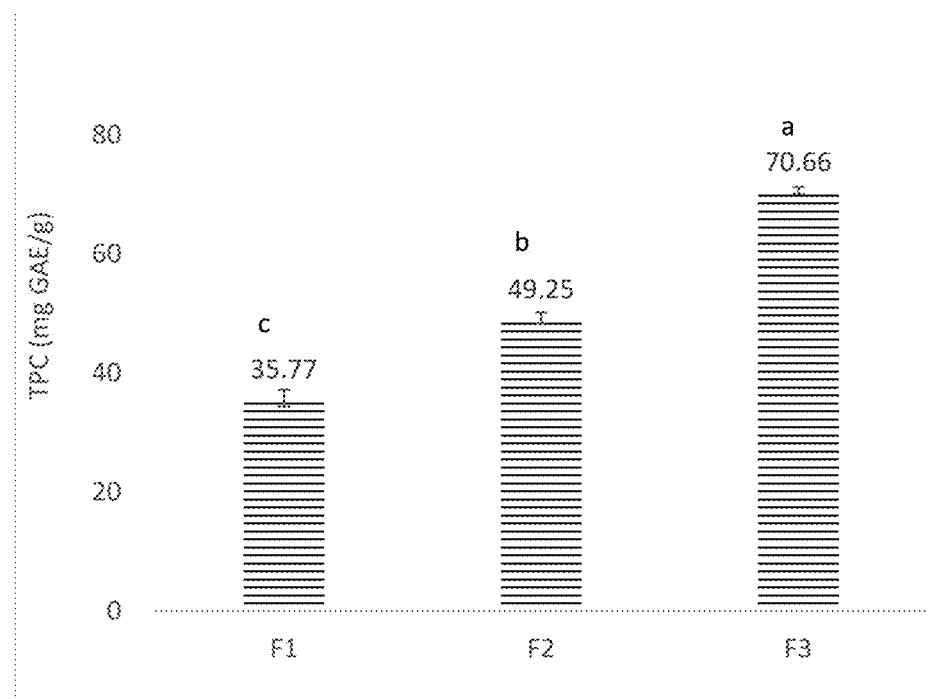
FIGS. 26A, 26B, 26C, and 26D are graphs showing total phenolic content and antioxidant activities of gel filtration fractions of kafirin Papain 1-3 kDa hydrolysate prepared at 360 kU/g and hydrolyzed for 4 hours, with FIG. 26A showing total phenolic content (mg GAE/g)
Figure 26B:
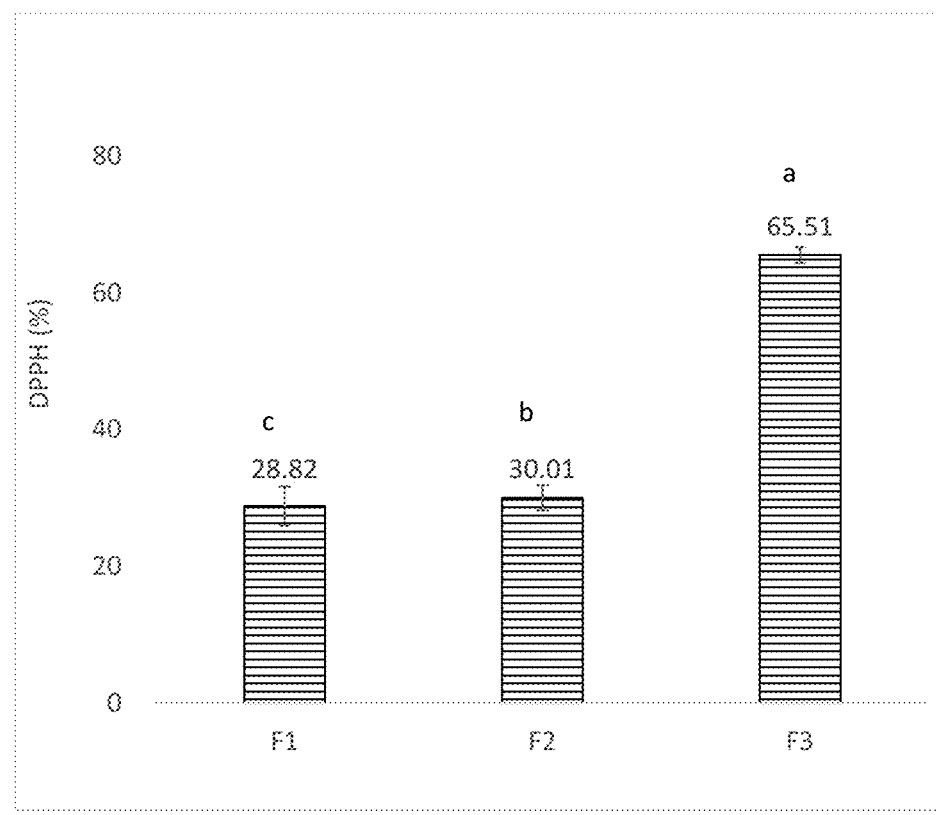
Figure 26C:
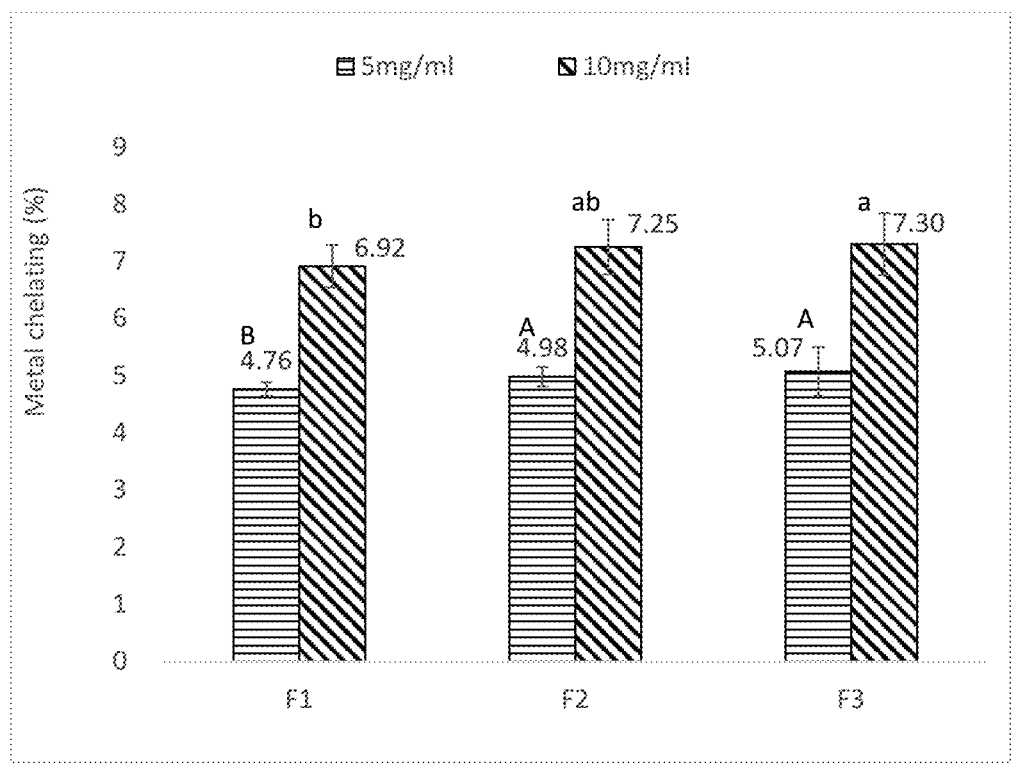
Figure 26D:
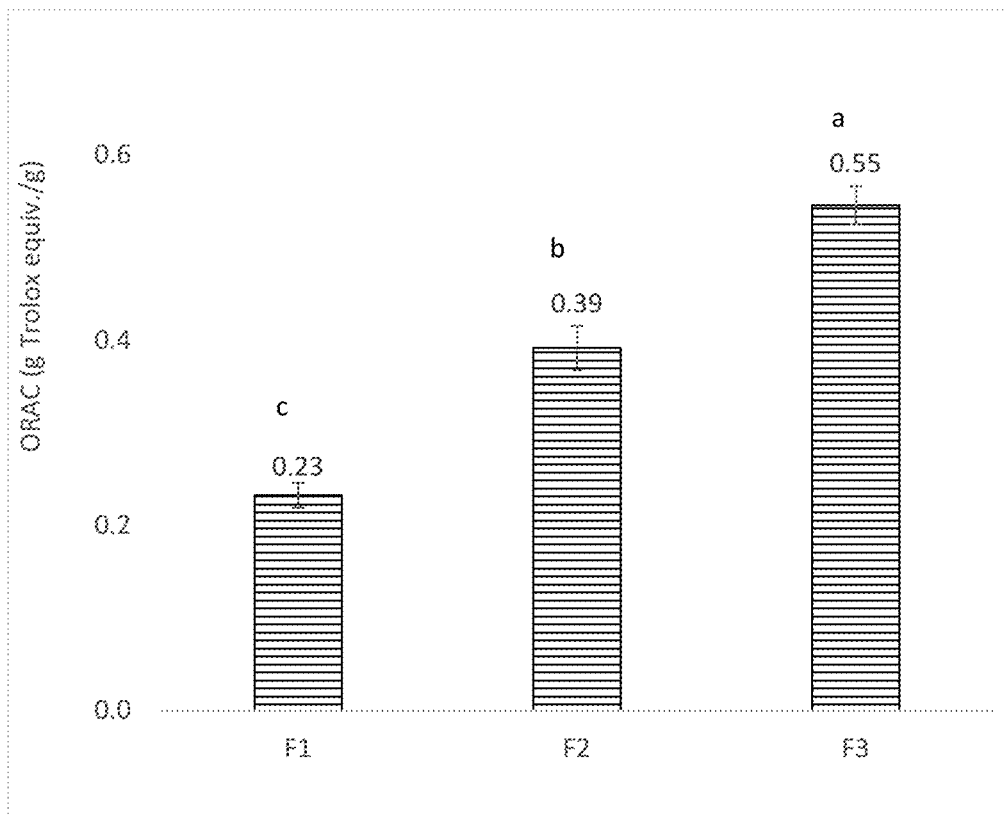

Purification and Identification of Antioxidative Peptides from Kafirin Papain 1-3 kDa Hydrolysates Gel Filtration of Kafirin Papain 1-3 kDa Hydrolysates Kafirin Papain 1-3 kDa fraction of hydrolysate was further separated on a Sephadex-G25 gel filtration column according to its molecular weight differences. Two major peaks appeared in the elution chromatogram (FIG. 25), and the entire elution was divided into three fractions (F1-F3).

After collecting and freeze-drying each fraction, total phenolic content and antioxidant activities of the separated fractions were analyzed. As shown in FIGS. 26A-26D, the second peak in the chromatogram (F3) exhibited higher TPC, DPPH %, ORAC, and metal chelating % than the other fractions which represented that the smaller-sized peptides possessed stronger activities in kaifrin Papain hydrolysates. The antioxidant activity as well as TPC of F3 was also significantly higher (P<0.05) than that fractionated before gel filtration.

Identification of Representative Peptide Sequences from Gel Filtration

The fraction 3 (F3) of gel-filtrated hydrolysate which showed excellent antioxidant activity in previous experiments was analyzed by RP-HPLC. Peaks at 2.6-, 5.8-, 13.6- and 15.9-minute had relatively higher area percentages from HPLC chromatogram, which were 14.9%, 6.24%, 11.67% and 9.63%, respectively. These peaks were eluted and analyzed for identification of amino acid sequence profile with MALDI-TOF/TOF MS. By fitting the MS spectrum to the beta kafirin protein patterns, 13 sequences with 100% relatively intensity were identified and summarized in Table 5.

TABLE 5

Representative antioxidant peptides in kafirin Papain hydrolysates.

| Peak | 2.6 min | 5.8 min | 13.6 min | 15.9 min |
|---|---|---|---|---|
| Area % | 14.90% | 6.24% | 11.67% | 9.63% |
| Coverage % | 66.10% | 28.60% | 72.90% | 29.70% |
| | LRQQ (SEQ ID NO: 4) | GLQDL (SEQ ID NO: 42) | AMCGVV (SEQ ID NO: 43) | QGVAAA (SEQ ID NO: 46) |
| | QLQGV (SEQ ID NO: 5) | LRQQ (SEQ ID NO: 4) | YLRQ (SEQ ID NO: 44) | AQVAQ (SEQ ID NO: 47) |
| | WQPN (SEQ ID NO: 6) | QLQGV (SEQ ID NO: 5) | TPCATS (SEQ ID NO: 45) | QQLQ (SEQ ID NO: 48) |
| | | WQPN (SEQ ID NO: 6) | | |

LRQQ (SEQ ID NO: 4), QLQGV (SEQ ID NO: 5), and WQPN (SEQ ID NO: 6) were present in both 2.6- and 5.8-minute peaks. Glutamine (Gln, Q) is an amino acid with antioxidant and immunomodulatory properties. In this study, 11 out of 13 identified peptides contained Gln at terminals or within the sequences. Thus, the extraordinary high level of glutamine in the identified peptides might play an essential role for the antioxidant activity of kafirin hydrolysate. Besides, leucine (Leu, L) and valine (Val, V) are the second and third abundant amino acids among the identified peptides, which are also important hydrophobic amino acids. Along with proline (Pro, P), they increased the overall hydrophobicity of the fraction of hydrolysate, therefore caused a higher antioxidant activity especially in hydrophobic lipid and oil phase. Tyr at N-terminal position could be responsible for the antioxidant activity capacity of YLRQ (SEQ ID NO: 44) in peak 13.6 minute. Ala at the N-terminal might be responsible for the antioxidant activities of AQVAQ (SEQ ID NO: 47) and AMCGVV (SEQ ID NO: 43).

Conclusions

Kafirin hydrolysates obtained with Papain exhibited notable antioxidant activity as well as high yield. The optimal reaction parameters were determined as protein content of 4%, enzyme-to-substrate ratio 360 kU/g, and hydrolysis time of 4 hours. After fractionation by ultrafiltration, peptides with lower $M_w$ (1-3 kDa) exhibited favorable antioxidant activities evaluated by several different assays. Results from the assays of DPPH %, ABTS %, reducing power, and metal chelating demonstrated that the antioxidant activity of kafirin hydrolysates appeared to involve multiple modes of actions including electron/hydrogen donation, radical quenching, and metal ion chelation. In addition, in the emulsion and meat model systems, the selected fraction of hydrolysates effectively retarded oil and/or lipid peroxidation. The inhibition of lipid oxidation has been attributed to chelation of prooxidative metal ions, quenching singlet oxygen, scavenging free radicals, termination of free radical chain reactions, and the ability to perform as shielding barriers to minimize the contact of prooxidants to susceptible oil droplets. 13 peptide sequences were identified from HPLC analysis followed with MALDI-TOF/TOF MS of the most potent fraction from gel filtration chromatography. Glutamine and hydrophobic amino acids (Pro, Leu, and Val) were found largely present in the identified peptide sequences, which might be accountable for a high antioxidant activity.

These combined data provided important evidences showing that some kafirin peptides hydrolyzed with Papain can be used as potential antioxidants as alternatives to synthetic antioxidants to protect the susceptible ingredients within the food and feed products from peroxidation. The production of peptides from kafirin can also improve the utilization of distillers' grain and accelerate the industrial production cycle with an additional revenue stream.

Example IV

Introduction

About 40% of U.S. corn is used for ethanol production, resulting in over 90 billion pounds of distiller's grains (DDGS) and corn gluten meals (CGM) each year. Novel value-added uses of these high protein byproducts are key to the economic viability of fuel ethanol production. Antioxidants have a multi-billion dollars market with an ever-increasing size. They are commonly added into human foods, animal feeds, and pet foods to inhibit lipid oxidation and extend product shelf-life. Many proteins, such as those in DDGS and CGM, possess antioxidative peptide sequences and structural domains; however, they are mostly buried within the globular protein's hydrophobic core and inaccessible to prooxidants, radical species, and transition metal ions. The objective of this study is to expose antioxidative domains of CGM proteins through enzymatic hydrolysis and study antioxidant activities of these hydrolysates using various assays.

Materials and Methods

Materials

Corn gluten meal (CGM) (61.3% protein, determined using LECO) was provided by Grain Processing Corporation (Muscatine, Iowa). Chemicals, enzymes, solvents, and reagents were from Fisher or Sigma.

Protein Hydrolysate Production

CGM was water-washed, and then defatted with hexane for three times (1:6, w:v), dried, and stored at 4° C. until further uses. Reaction was carried out in a SHELLAB shaking water bath with controlled temperature and mixing. Hydrolysis pH and temperature were varied depending on specific enzymes based on manufacture recommendations. Types of enzymes, enzyme to protein ratios, and hydrolysis times were varied to maximize antioxidant yield and activity. Reactant was centrifuged, and the supernatant containing soluble protein hydrolysates was collected and lyophilized for analysis. Promising hydrolysates were also ultrafiltrated using molecular membranes with different cut-off ranges (i.e., <1 k, 1-3 k, 3-5 k, 5-10 k, >10 k) and then analyzed.

Antioxidant Characterization

Protein recovery (i.e., antioxidant yield), degree of hydrolysis (DH), total phenolic content, antioxidant activity (DPPH, ABTS, metal chelating) and performances of lipid oxidation in model emulsion system were analyzed.

Results

Figure 27A:
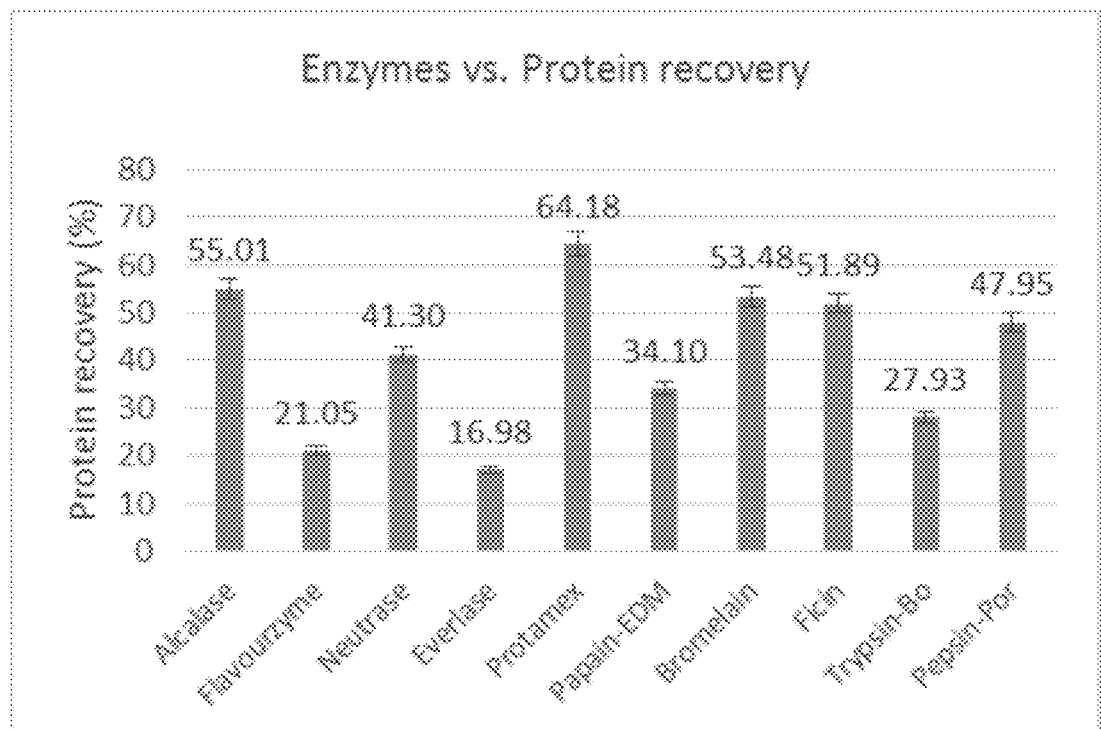
FIGS. 27A and 27B are graphs showing effect of enzyme types on protein recovery and antioxidant activity of corn gluten meal (CGM) hydrolysates.
Figure 27B:
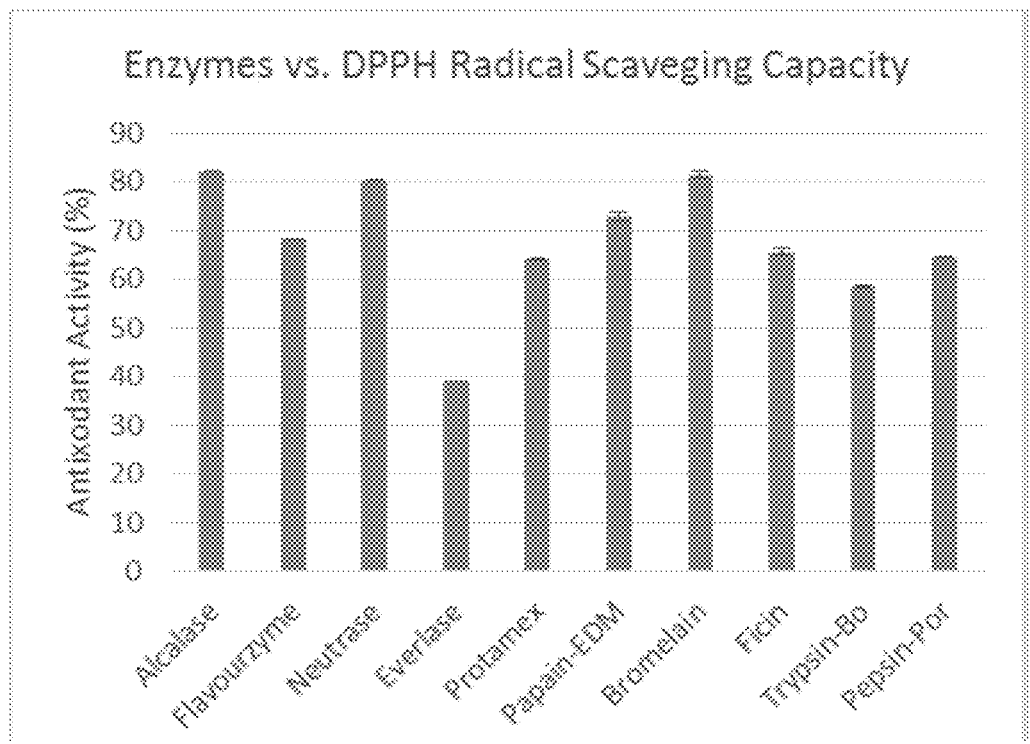
Figure 28A:
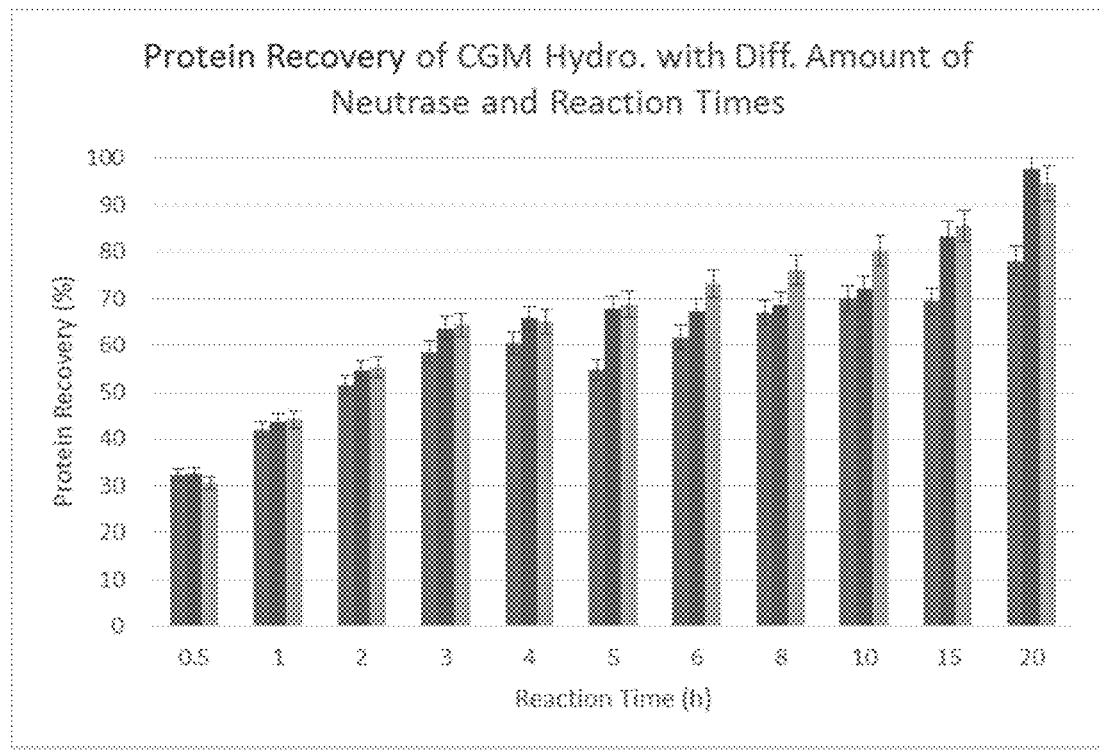
FIGS. 28A, 28B, 28C, 28D are graphs showing effect of Neutrase amount and reaction time on protein recovery, DH, antioxidant activity, and total phenolic content of CGM hydrolysate.
Figure 28B:
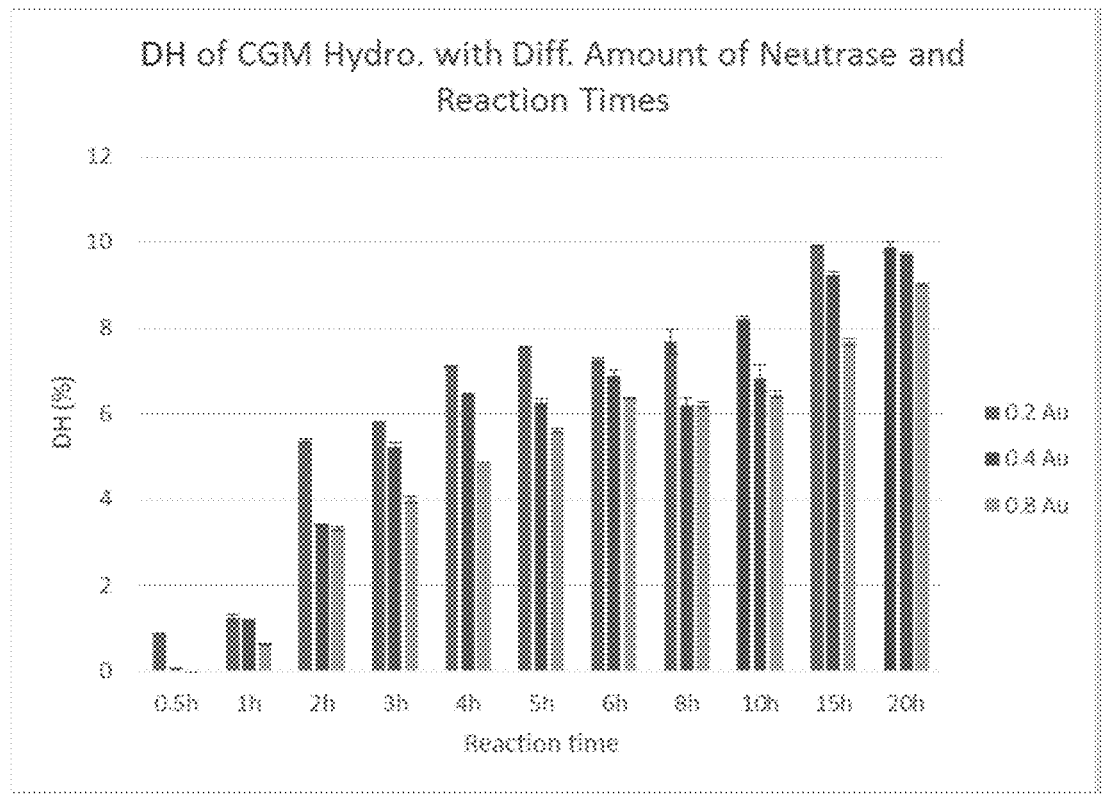
Figure 28C:
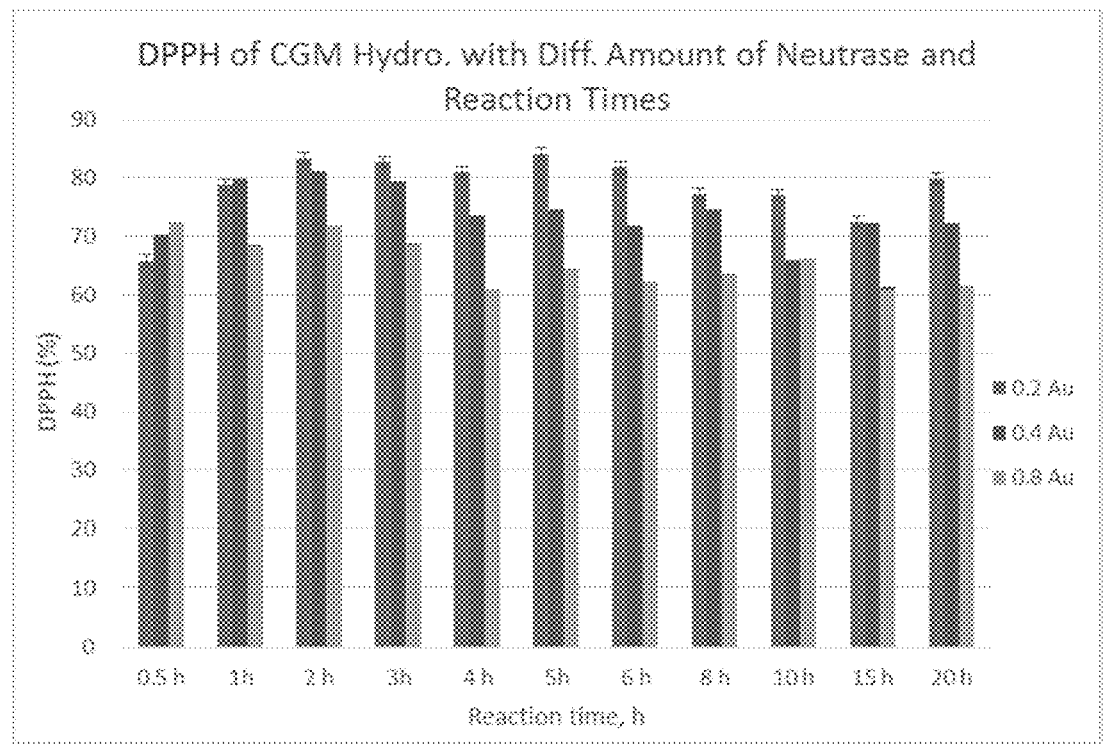
Figure 28D:
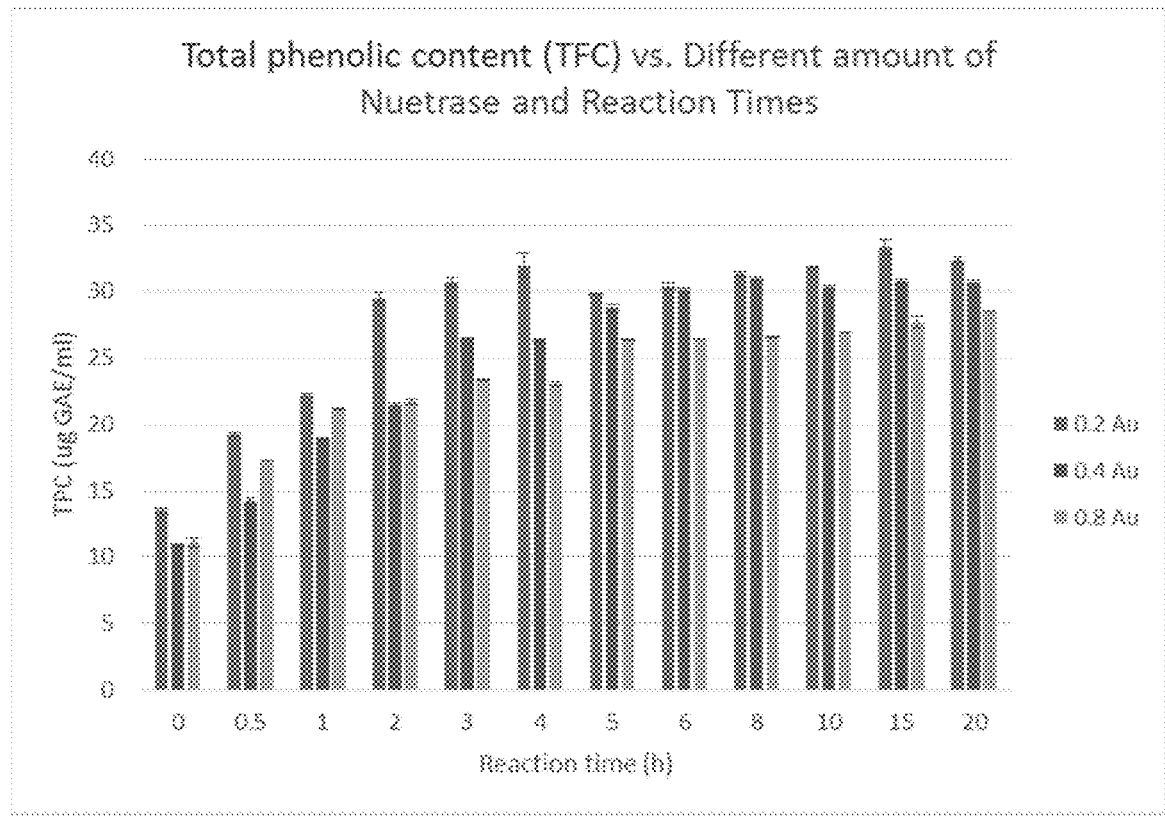

Alcalase, Neutrase, Protamaex, Bromelain, Ficin, and Pepsin are promising enzymes with better antioxidant yield and performances from corn gluten meal. See FIGS. 27A and 27B.

Antioxidant yield, degree of hydrolysis (DH) and total phenolic content (TFC) increased with reaction times. Antioxidant activity (DPPH) was less affected by reaction times. The amount of enzyme added affected the hydrolysis reaction. Neutrase hydrolysis of CGM at 0.4 Au/g protein for 3 hours was considered as an optimal condition with respect to protein recovery, activity, and time needs. See FIGS. 28A-28D.

Figure 29A:
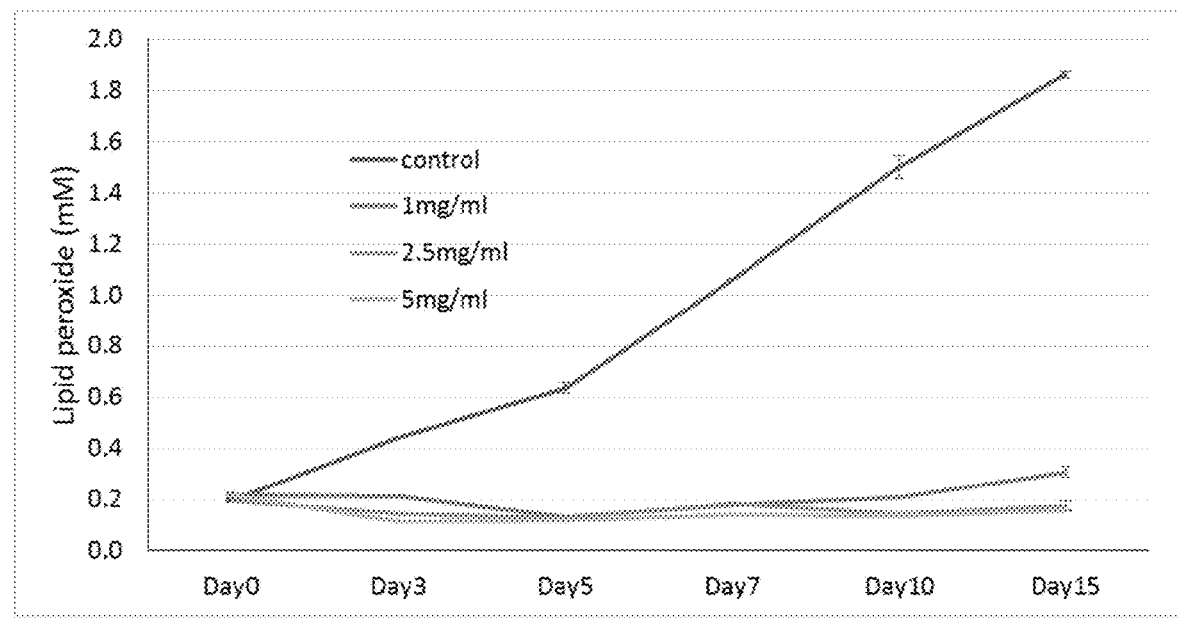
FIGS. 29A and 29B are graphs showing performances of CGM hydrolysate in inhibiting lipid oxidation in soybean oil emulsions.
Figure 29B:
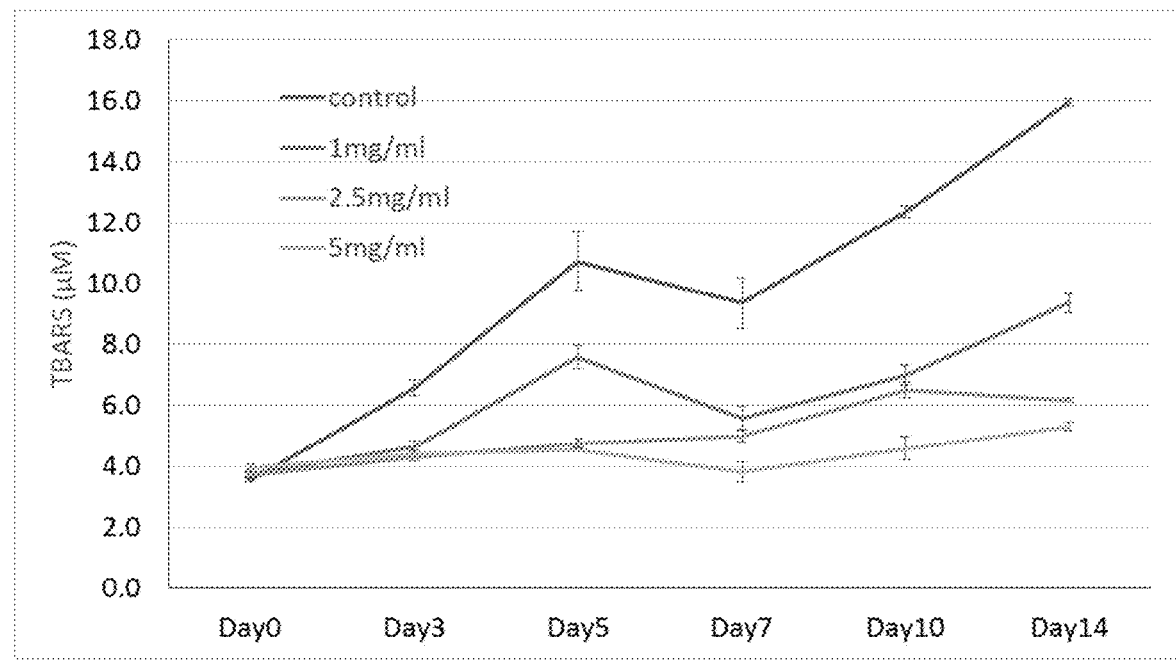
Figure 30A:
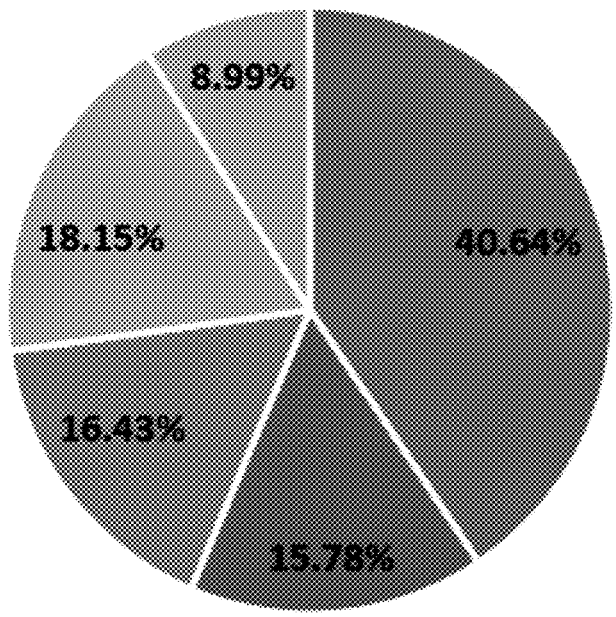
FIGS. 30A, 30B, 30C, and 30D are graphs showing effect of hydrolysate molecular size on antioxidant activity.
Figure 30B:
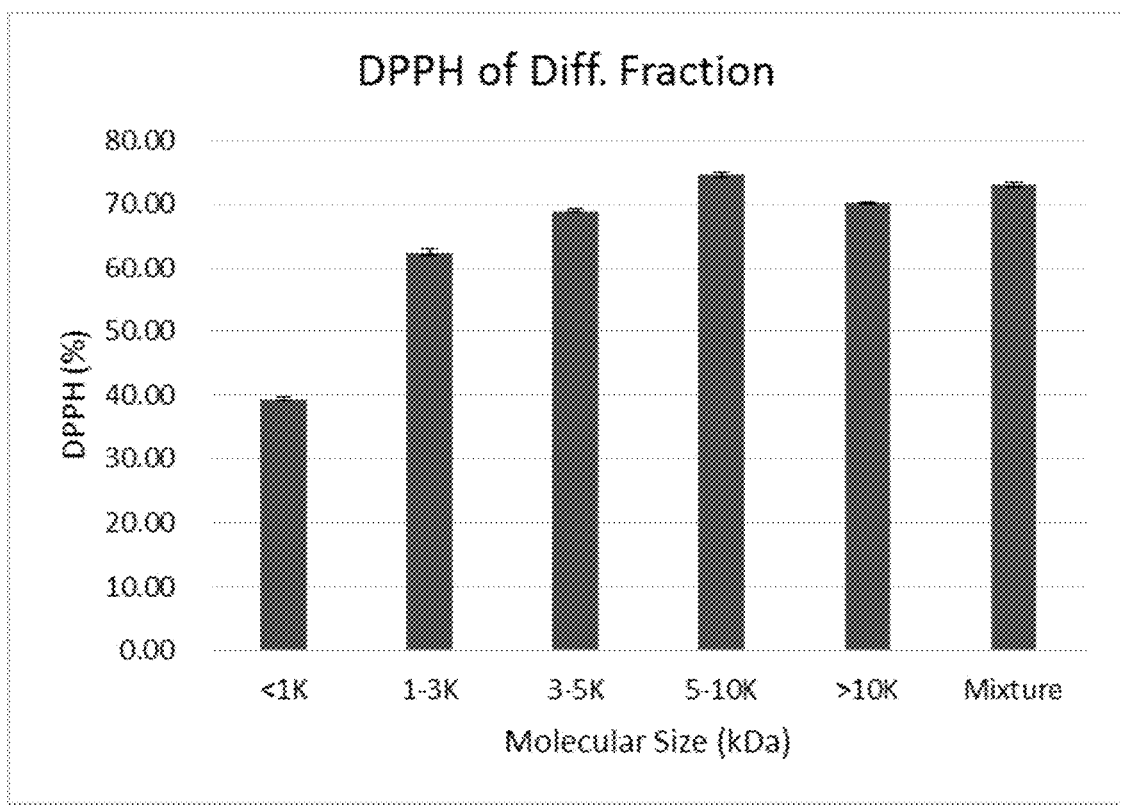
Figure 30C:
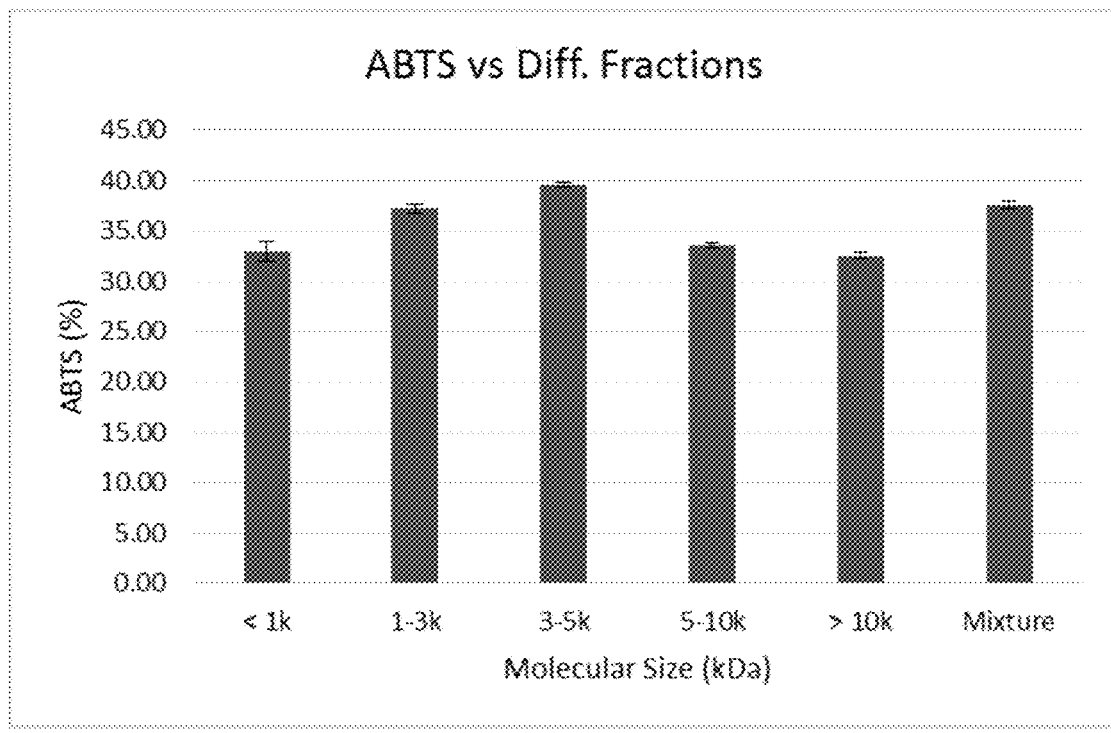
Figure 30D:
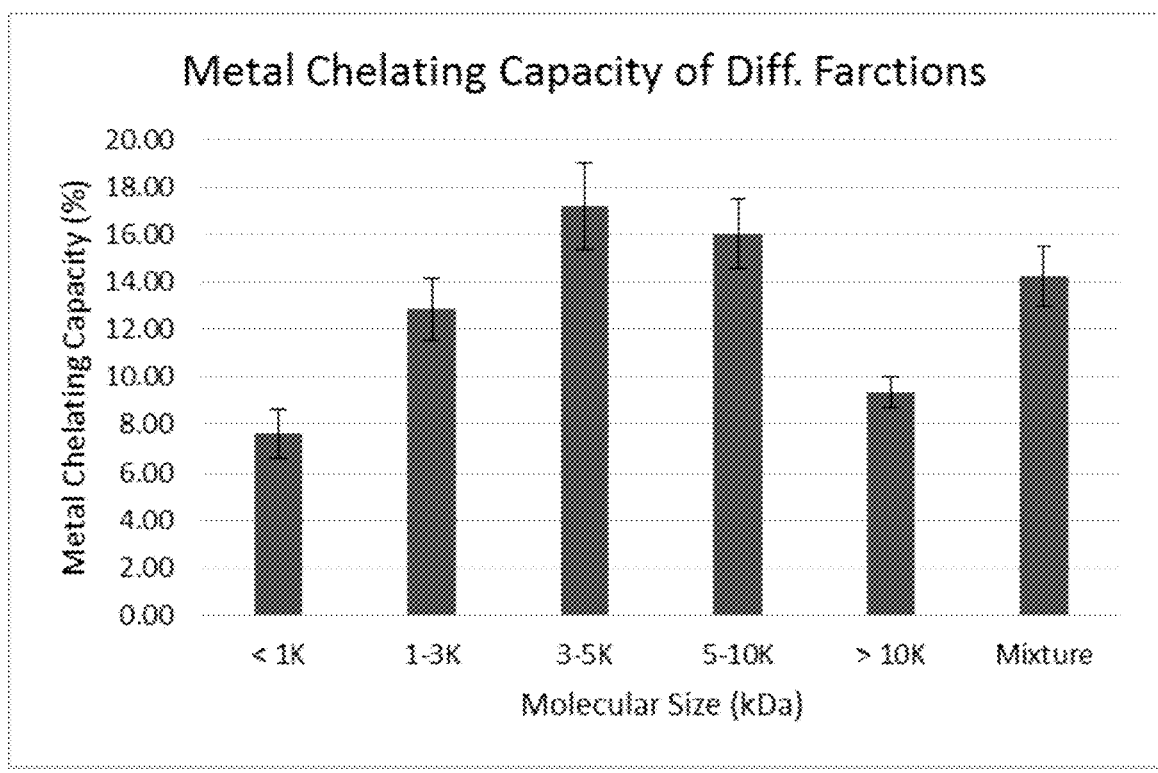

GCM hydrolysates (3 h, 0.4 Au/g protein) were effective antioxidant in preventing lipid oxidation in soybean oil emulsion systems. See FIGS. 29A and 29B.

3-5 k of Neutrase hydrolysates was the most promising antioxidants among different molecular size fractions. See 30A-30D.

CONCLUSIONS

Protein hydrolysates from corn gluten meal exhibited great antioxidant performances. CGM and other corn byproducts could be an excellent source for natural antioxidants with intrinsic nutritional and health benefits.

The invention claimed is:

1. A method of producing an antioxidant peptide product from a cereal crop material comprising:
   reacting the cereal crop material with an enzyme capable of hydrolyzing proteins within the cereal crop material, thereby forming a hydrolysate peptide mixture,
   wherein the enzyme is a microbial-originated protease, a plant-originated protease, or an animal-originated protease, the microbial-originated protease being selected from the group consisting of *Aspergillus* fungi, Neutrase (*Bacillus amyloliquefaciens*), Everlase (*Bacillus* sp.), and Protamex (*Bacillus* sp.); and
   fractionating the hydrolysate peptide mixture and recovering peptides having a molecular weight greater than about 1 kDa, thereby forming the antioxidant peptide product.

2. The method of claim 1, wherein the cereal crop material comprises corn or grain sorghum.

3. The method of claim 2, wherein the cereal crop material comprises grain sorghum.

4. The method of claim 1, wherein the enzyme is a microbial-originated protease or a plant-originated protease.

5. The method of claim 1, wherein the enzyme is a protease produced by an organism selected from the group consisting of Caricaceae plants, *Ficus* plants, Suidae animals, and Bovidae animals.

6. The method of claim 1, wherein at least a portion of the fat or oil content in the cereal crop material is removed from the cereal crop material prior to said reacting.

7. The method of claim 1, wherein the cereal crop material comprises a mixture of proteins that have been extracted from a cereal crop.

8. The method of claim 7, wherein the cereal crop material comprises at least about 25% by weight of the mixture of proteins.

9. The method of claim 1, wherein the reacting step comprises reacting from about 0.1 to about 1 Anson Units of the enzyme per gram of protein in the cereal crop material.

10. The method of claim 1, wherein the cereal crop material is reacted with the enzyme for about 1 to about 24 hours.

11. The method of claim 1, wherein the antioxidant peptide product comprises peptides having a weight-average molecular weight of about 1 kDa to about 10 kDa.

12. The method of claim 1, wherein the antioxidant peptide product comprises peptides having a weight-average molecular weight of about 3 kDa to about 10 kDa.

13. The method of claim 1, wherein the antioxidant peptide product has a total phenolic content of greater than about 30 milligrams of gallic acid equivalent/gram.

14. The method of claim 1, wherein the antioxidant peptide product comprises peptides having amino acid sequences MDMQ (SEQ ID NO: 1), QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and/or VAQ.

15. An antioxidant peptide product formed by the method of claim 1.

16. A food product comprising the antioxidant peptide product of claim 15.

17. A hydrolysate peptide mixture formed by reacting a cereal crop material with an enzyme capable of hydrolyzing proteins within the cereal crop material, the hydrolysate peptide mixture comprising peptide hydrolysate products each having a molecular weight of about 1 kDa to about 10 kDa,
   wherein the enzyme is a microbial-originated protease, a plant-originated protease, or an animal-originated protease, the microbial-originated protease being selected from the group consisting of *Aspergillus* fungi, Neutrase (*Bacillus amyloliquefaciens*), Everlase (*Bacillus* sp.), and Protamex (*Bacillus* sp.).

18. The hydrolysate peptide mixture of claim 17, wherein each peptide hydrolysate product comprises an amino acid sequence selected from the group consisting of MDMQ (SEQ ID NO: 1), QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and VAQ.

19. A method of forming an antioxidant peptide product comprising synthesizing one or more peptides having an amino acid sequence selected from the group consisting of MDMQ (SEQ ID NO: 1), QQWQ (SEQ ID NO: 2), QWQQ (SEQ ID NO: 3), LRQQ (SEQ ID NO: 4), QLQGV (SEQ ID NO: 5), WQPN (SEQ ID NO: 6), and VAQ.

* * * * *